US010099158B2

(12) United States Patent
Ritchie et al.

(10) Patent No.: US 10,099,158 B2
(45) Date of Patent: *Oct. 16, 2018

(54) METHOD AND APPARATUS FOR IMPROVED RESOLUTION CHROMATOGRAPHY

(75) Inventors: Harald Ritchie, Runcorn (GB); Ross Andrew Shalliker, Hornsby (AU)

(73) Assignees: Thermo Electron Manufacturing Limited, Cambridge (GB); University of Western Sydney, Penrith, NSW (AU)

( * ) Notice: Subject to any disclaimer, the term of this patent is extended or adjusted under 35 U.S.C. 154(b) by 536 days.

This patent is subject to a terminal disclaimer.

(21) Appl. No.: 13/480,590

(22) Filed: May 25, 2012

(65) Prior Publication Data

US 2012/0298585 A1    Nov. 29, 2012

Related U.S. Application Data

(60) Provisional application No. 61/519,731, filed on May 26, 2011.

(51) Int. Cl.
*G01N 30/60* (2006.01)
*B01D 15/22* (2006.01)
(Continued)

(52) U.S. Cl.
CPC ............ *B01D 15/22* (2013.01); *B01D 15/24* (2013.01); *G01N 30/60* (2013.01); *G01N 30/603* (2013.01);
(Continued)

(58) Field of Classification Search
None
See application file for complete search history.

(56) References Cited

U.S. PATENT DOCUMENTS

| T959,004 I4 | 6/1977 | Kirkland et al. |
| 4,537,217 A | 8/1985 | Allen, Jr. |
| (Continued) | | |

FOREIGN PATENT DOCUMENTS

| CN | 101206205 A | 6/2008 |
| CN | 101489637 | 7/2009 |
| (Continued) | | |

OTHER PUBLICATIONS

Volumetric flow rate. Wikipedia. Accessed from <http://en.wikipedia.org/wiki/Volumetric_flow_rate> on Jan. 14, 2015.*
(Continued)

*Primary Examiner* — Kara Graber

(57) ABSTRACT

An apparatus and a method are provided for column chromatography which provide improvements in separation resolution and detection sensitivity, comprising a chromatography column, the column having an inlet and an outlet, wherein the outlet is configured to split a flow of eluate as it leaves the column through the outlet into at least two separate portions, wherein the apparatus is configured to separately process the portions, for example to separately detect a portion or separately collect fractions of a portion with improved resolution. A split frit assembly is preferably configured to split the flow of eluate. The portions preferably emanate from different radial regions of the column. An end fitting for the column outlet may be provided having multiple ports to separately convey the portions.

30 Claims, 27 Drawing Sheets

(51) Int. Cl.
  *B01D 15/10* (2006.01)
  *B01D 15/24* (2006.01)
  *G01N 30/22* (2006.01)

(52) U.S. Cl.
  CPC ..... *G01N 30/6004* (2013.01); *G01N 30/6017* (2013.01); *G01N 30/6086* (2013.01); *B01D 15/10* (2013.01)

(56) References Cited

U.S. PATENT DOCUMENTS

| | | | |
|---|---|---|---|
| 4,999,102 | A | 3/1991 | Cox et al. |
| 5,124,133 | A | 6/1992 | Schoenrock |
| 6,905,595 | B2 | 6/2005 | Gebauer |
| 2002/0179513 | A1 | 12/2002 | Willis et al. |
| 2008/0017579 | A1 | 1/2008 | Hermansson et al. |
| 2010/0189602 | A1* | 7/2010 | Baeuerle et al. ............... 422/70 |

FOREIGN PATENT DOCUMENTS

| | | |
|---|---|---|
| DE | 3939854 A1 | 6/1990 |
| EP | 0257582 | 2/1988 |
| EP | 0371648 | 6/1990 |
| EP | 0310867 A2 | 7/1991 |
| JP | 54139596 A2 | 10/1979 |
| JP | 6167560 U | 5/1986 |
| JP | 6253857 A | 3/1987 |
| JP | 62063857 | 3/1987 |
| JP | 62240857 | 10/1987 |
| JP | 01094260 | 4/1989 |
| JP | 02157653 A | 6/1990 |
| JP | 2000088829 A2 | 3/2000 |

OTHER PUBLICATIONS

Abia, J; Mriziq, K., Guiochon, G. Radial heterogeneity of some analytical columns used in high performance liquid chromatography. Journal of Chromatoraphy A, 1216 (2009) 3185-3191. Feb. 2009.*
English machine translation of DE3939854 by Mitsuo. 1990.*
Broyles, et al., Visualization of sample introduction in liquid chromatography columns: the effect of the frit diameter, J. Chromatography A, 855 (1999), 367-382.
Broyles, et al., Visualization of solute migration in chromatographic columns: quantitation of the concentration in a migrating zone, J. Chromatography A, 867 (2000), 71-92.
Knox, et al., Interaction of radial and axial dispersion in liquid chromatrography in relation to the "infinite diameter effect", J. Chromatography, 122 (1976), 129-145.
Shalliker, et al., Visualization of solute migration in liquid chromatography columns, J. Chromatography A., 826 (1998) 1-13.
Shalliker, et al., Visualization of sample introduction in liquid chromatographic columns: contribution of a flos distributor on the sample band shape, J. Chromatography A, 865 (1999) 83-95.
Shalliker, et al., Physical evidence of two wall effects in liquid chromatography, J. Chromatography A. 888 (2000) 1-12.
Broyles, et al., Visualization of solute migration in chromatographic columns: influence of the frit porosity, J. Chromatography A., 917 (2001) 1-22.
Camenzuli, et al., "The design of a new concept chromatography column", Analyst (2011), 136, pp. 5127-5130.
Dardoize, et al., "A new split-flow injector for preparative liquid chromatography columns. Annular injection system", Anal. Bioanal. Chem. (2002), 372, pp. 817-821.

* cited by examiner

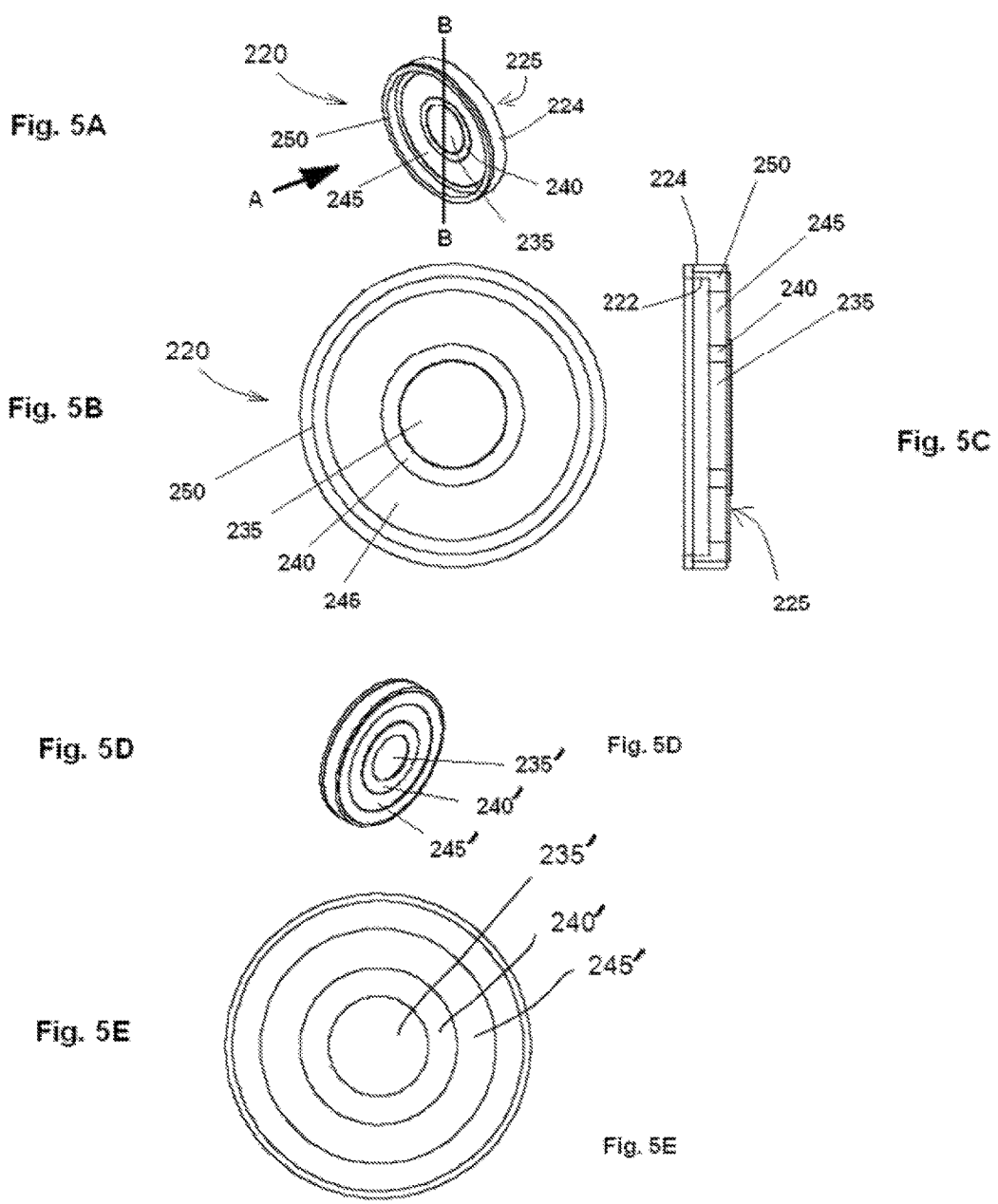

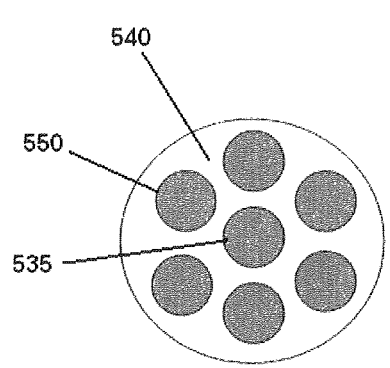 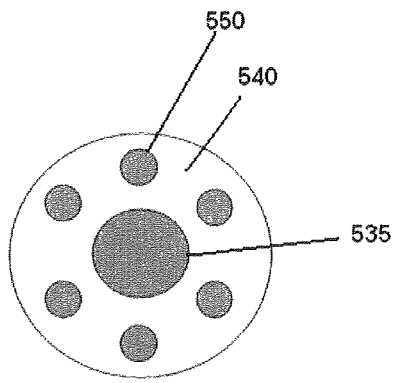
Fig. 5F    Fig. 5G
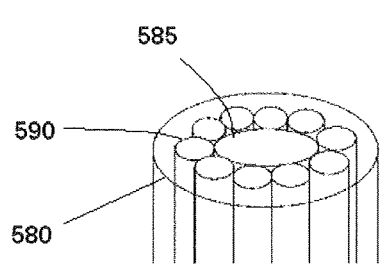 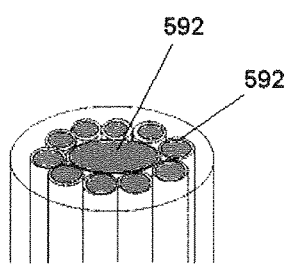
Fig. 5H    Fig. 5I

METHOD AND APPARATUS FOR IMPROVED RESOLUTION CHROMATOGRAPHY

CROSS-REFERENCE TO RELATED APPLICATIONS

This application claims priority to U.S. provisional patent application Ser. No. 61/519,731 filed May 26, 2011, entitled "Improved Resolution Chromatography System," which application is incorporated herein by reference in its entirety.

FIELD OF THE INVENTION

This invention relates to the field of column chromatography.

BACKGROUND OF THE INVENTION

Chromatography columns have been extensively developed and are used routinely in both analytical and preparative chromatography. As is well known, the separation in a chromatography column of a sample (also termed an analyte or solute) comprising a mixture of components is achieved by dissolving the sample in an eluant to form a fluid mobile phase and passing the mobile phase through a stationary phase typically packed within a tubular column, thereby causing the sample to separate into its components due to the differences in the partitioning between the mobile and stationary phases of the different components (i.e. the components have different partition coefficients). The eluant fluid is most commonly a liquid but may be another fluid such as a supercritical fluid (SCF) and the invention relates to columns used with liquid or SCF mobile phases. The invention, however, does not relate to gas chromatography (i.e. the fluid is not a gas). In column chromatography the stationary phase is typically in the form of a bed of packed particles or a porous monolithic block within a column. This invention relates especially to packed columns but it is not limited to only packed columns. Often the columns comprise reusable columns with disposable cartridges, both of which are usually cylindrical. This invention may be used with cylindrical columns (most preferably circular cylindrical columns) or columns having other cross-sectional profiles. That is, the wall of the column may have numerous cross-sectional profiles but most preferably has a circular profile in its transverse cross section.

As described, the mobile phase is passed through the column and the eluate leaving the column is detected as a function of time. The detected signal variation with time, the chromatogram, indicates the presence of different components within the mixture. The degree of separation of the different components depends upon the separation efficiency or resolution of the column. The resolution of the column depends upon many factors. Such factors include the nature of the mobile and stationary phases, which have been extensively studied and developed.

It is also known that the shape of the injected sample is a factor affecting the resolution of the column. The sample is usually introduced into the column substantially across the diameter of the column. Head fittings such as frits are usually used at the inlet of the column. Distributors may be used to aid in distributing the sample to try and obtain a uniform layer of sample across the whole diameter of the column. U.S. Pat. No. 4,999,102 describes a manifold system for evenly distributing liquid to, and/or evenly collecting a liquid from, a cell of a large scale separator system. Where used as an inlet, the manifold distributes a single stream into a plurality of streams through a tier of branches and the final multiplicity of fluid passage devices is arranged in a pattern which assures approximately even distribution of liquid across the entire cell at the interface between the manifold and the cell. Where used as an outlet the manifold is arranged in reverse to collect from an even distribution across the cell and, via a tier of branches, join the streams into a single conduit. In a similar manner, U.S. Pat. No. 5,124,133 describes a system for a uniform flow profile of a liquid through a packed bed that involves distributing the liquid evenly across the top surface of the packed bed.

Other types of inlet system are known, often for different purposes. For example, EP 371 648 A discloses an apparatus designed for displacement chromatography in which an inlet distribution manifold is present. Each liquid in the displacement chromatography sequence flows through the same radial regions of the column. On the other hand, JP 62-063857 A describes a plate-shaped column having a plurality of inlets for possible multiple samples in which an electric field may be applied in an orthogonal direction to the inlet flow to provide a two dimensional separation across the column plate, which also has a plurality of outlets.

In JP 62-240857 A is described a chromatography column for preparative chromatography in which there is provided annular separation of flow exiting the column such that central flow streams can be isolated from peripheral flow streams. The peak shape of the eluting bands from the central rings were better compared to those of the eluting bands from the outer rings, which showed significant band distortion.

EP 257 582 describes a preparative scale chromatography column in which sample is loaded into the column through a tube inserted into the bed from the column outlet. This tube is centered in the bed approximately 20% below the column inlet. That is, there is packing material above the tube. Once the sample is loaded onto the column a mobile phase elutes the sample through the column (outside of the sample introduction tube). Sample then exits the outlet of the column through a series of holes or slots at the outlet. The outlet has slots at concentric locations, but is without a central exit slot since the introduction tube is in the central section of the column.

More recently, in relation to high performance liquid chromatography (HPLC), Shalliker et al. in the late 1990s enabled fluid flow in a column to be visualised. In glass columns, using a stationary phase and a mobile phase with the same refractive index, they were able to visualise fluid flow with the aid of dye markers. Their results showed that the manner in which sample is introduced to the bed of a chromatography column is important. Ideally the injection plug should be a cylindrical-square plug, but various factors ultimately lead to a parabolic sample band, for example, as the frit porosity decreased plug flow becomes more parabolic. Broyles, Shalliker and Guiochon, ('*Visualization of Solute Migration in Chromatographic Columns. Influence of the Frit Porosity*'. *J. Chromatography A.*, 917 (2001) 1-22) illustrated that as the inlet frit porosity decreased plug flow became more parabolic. Use of a distributor improved the uniformity of the flow velocity across the radial cross section of the bed, however, at the cost increasing the axial dispersion, which ultimately led to a substantial decrease in separation performance. Irrespective of the frit porosity or whether or not a distributor was employed, sample distribution was not uniform across the column radial cross section. Shalliker et. al. (J. Chromatography A, 865 (1999) 83-95) showed that neither frits nor distributors serve to distribute sample uniformly across the column, and there is a higher tendency for the sample to be more concentrated in the central region of the bed (conversely, more dilute in the perimeter region of the bed). Furthermore, the frit diameter should match that of the column internal diameter (Broyles, Shalliker and Guiochon, J. Chromatography A, 855 (1999), 367-382). If not, with a frit having a narrower diameter than that of the column, very serious parabolic flow results. It may be intuitive to the chromatographer that the frit diameter must equal that of the column internal diameter, but it is not always possible to achieve, particularly in the case of columns prepared by axial compression where the head fitting is inside the column itself. For these types of columns the diameter of frit must be less than the column as the frit must be contained within a housing unit in order to prevent leakage and damage to the column wall.

In another study, Shalliker et al ('Physical Evidence of two Wall Effects in Liquid Chromatography'. J. Chromatography A. 888 (2000) 1-12 and 'Visualization of Solute Migration in Liquid Chromatography Columns'. J. Chromatography A., 826 (1998) 1-13) demonstrated that when sample was introduced into the bed at a depth approximately 1 cm below the frit, via a central point injection (CPI), migration of the sample was coincident within the central radial section of the bed. While excellent separation efficiency was observed by Shalliker et. al. when utilising the CPI technique, it should be pointed out that such a sample introduction method is tedious, and prone to be destructive to the column bed. Hence the technique is not suited to routine applications. Furthermore, whilst central point injections allow for the most efficient means of solute transport along the column since such injections allow the sample to be concentrated in a local, central zone within the most efficiently packed region of the column, modern columns have effectively prevented the use of such injection techniques, since valve injection disperses sample across the column as it enters by a frit and distributor at the top of the column. As such, central point injection processes have been largely abandoned.

The effect of the presence of the column wall and the packing of the column near to the walls on the flow of sample has been discussed. Knox, Laird and Raven, (J. Chromatography, 122 (1976), 129-145), showed that flow velocity very close to the wall was somewhat higher than in the centre of the column. They also showed that a disturbed region of column packing extends into the column causing serious band broadening and peak distortion. The wall region in an otherwise well packed LC column may extend about 30 particle diameters into the column. Shalliker, Broyles and Guiochon, (J. Chromatography A, 888 (2000) 1-12) described the presence of two wall effects. Both wall effects are caused by heterogeneity in the column packing. A particle packed chromatography column has a lower bed density in the central (radial) section of the column, the central section being relatively uniform, but beyond this zone packing density gradually increases towards the wall. Hence flow velocity is highest in the central section of the column and lowest near the wall, and this contributes to a parabolic plug flow. However, in the immediate vicinity of the wall the packing density rapidly decreases. This factor is a result of the geometrical nature of the column and the particles. Both the particles and the column are rigid; neither can distort to accommodate the other. Hence the void space increases at the wall, and it is here that the column permeability is at its highest. Hence the flow velocity is greatest in the region immediately adjacent to the column wall. Both these wall effects contribute greatly to decreasing the efficiency of migration.

Broyles, Shalliker and Guiochon, (J. Chromatography A, 867 (2000), 71-92), demonstrated that, amongst other things, the migration distance after a given time varies markedly with radial position and that the exit fitting affects the peak shape detected post-column.

It is therefore known that sample migration through a particle packed chromatography column is not described by a cylindrical plug flow model. Numerous factors, including the nature of the frit, the presence of a distributor, the injection process itself, the wall effect and the heterogeneity of the packing density, lead to a sample plug or band that is parabolic or bowl-like in shape, generally having a higher concentration central region that is moving at a higher velocity than a more dilute region nearer the wall. There is also a region of low concentration fast flow very close to the wall. The generally parabolic shape of the band places greater demand on the efficiency of the column. More plates are needed to separate parabolically broadened zones than cylindrically broadened zones. Hence, longer columns are necessary to effect separation, which results in an increase in time, possibly resulting also in a decrease in the potential flow velocity in order to accommodate a longer column. Monolithic stationary phases in columns may also suffer from wall effects and plug flow through such columns is again not cylindrical.

Against this background the present invention has been made.

SUMMARY OF THE INVENTION

According to an aspect of the present invention there is provided an apparatus for column chromatography comprising a chromatography column, the column having an inlet and an outlet, wherein the outlet is configured to split a flow of eluate as it leaves the column through the outlet into at least two separate portions, wherein the apparatus is configured to separately process the separate portions.

According to another aspect of the present invention there is provided a method of column chromatography comprising: providing a mobile phase comprising a sample to be separated into components; flowing the mobile phase longitudinally through a liquid chromatography column from an inlet of the column to an outlet of the column, the mobile phase leaving the column through the outlet as an eluate; splitting the flow of eluate as it leaves the column through the outlet into at least two separate portions; and processing the at least two separate portions separately.

According to a further aspect of the present invention there is provided an apparatus for column chromatography comprising a chromatography column, the column having an inlet and an outlet, wherein the outlet is configured to direct a portion of a flow of eluate as it leaves the column to be processed separately from a remainder of the eluate, wherein the portion emanates from a restricted radial region of the column.

The present invention may provide numerous advantages. At least one of the separate processing types preferably comprises detection of the eluate. The present invention, for example, can enable enhanced detection of samples and improved assay performance from a chromatography column. In various embodiments the invention can enable, for example, a lower limit of detection for species being chromatographed due to improved detection sensitivity and/or improved peak capacity and peak resolution within a chromatographic assay. It has been found that the number of theoretical plates can be significantly increased and, in some embodiments for HPLC, the invention has been found to increase the number of theoretical plates compared to a conventional column by over 50%, i.e. in some cases the gain in separation efficiency has been found to be higher than 50% compared to an analogous conventional system without the split flow of eluate and accompanying separate processing. In the case of other types of column, gains of over 100% in the column efficiency (plate count) have been found. In general, where the column efficiency increases by a factor ×2 the resolution increases by a factor ×1.44.

It will be appreciated that, as an alternative to improving peak resolution for a given column length, the invention may enable the use of shorter columns to attain a given peak resolution compared to an analogous conventional system. A shorter column will enable faster chromatographic separations to be performed. A further advantage, for example, is that the use of only a portion of the eluate for detection can mean that a reduced solvent load is introduced into the detector, which can be very beneficial for certain detectors such as mass spectrometers and other detectors operating in a vacuum environment or bio-type reaction detectors, such as anti-oxidant detectors used in the discovery of medicinal compounds. The invention may therefore better enable the use of conventional size columns with MS detection. With regard to preparative chromatography, the invention may enable the collection of purer fractions of samples due to the improved separation efficiency. These and other advantages will be described in more detail and become more apparent from the following description of the invention.

The apparatus comprises a chromatography column, which is typically a liquid chromatography column but may be a supercritical fluid chromatography column, the column having an inlet and an outlet, whereby a mobile phase containing a solvent and sample to be separated may be introduced to the column through the inlet and flowed longitudinally (i.e. axially) along the column to the outlet. The outlet is configured to split a flow of eluate (i.e. mobile phase leaving the column) as it leaves the column. The outlet is configured such that the flow is split into at least two separate portions and each portion is processed separately, e.g. directed to its own processing means separate to processing means which the other portion (or portions) is (or are) directed to. The configuration of the column outlet in this way enables separation of the eluate flow to be performed on-column, not post-column. Thus, a portion of the eluate flow leaving the column is separated from another portion and processed separately to the other portion. In certain preferred embodiments, a portion of the eluate flow leaving the column is separated from another portion and detected separately to the other portion. In certain preferred embodiments, a portion of the eluate flow leaving the column is separated from another portion and fractions of the portion are collected separately from the other portion.

Preferably, the outlet is configured to split a flow of eluate as it leaves the column through the outlet into at least two separate portions: at least a first portion of the flow and a second portion of the flow. Preferably, a first portion of the flow of eluate is directed to a first processing means and a second portion of the flow of eluate is directed to a second processing means separate from and preferably different to the first processing means. For example, preferably the first processing means comprises a detector for detecting a sample present in the eluate, and the second processing means may comprise a waste receiver, or be the inlet of the same or another chromatography column so that the second portion is subjected to at least a further round of chromatography. However, the second processing means may also comprise a detector for detecting a sample present in the eluate. Many other processing means, and combinations thereof, could be employed and these are discussed in more detail herein below. In this way, for example, the invention provides a column with an outlet configured to selectively direct a portion of the eluate flow to a first processing means, e.g. a detector, while it directs another portion to another processing means separate to the first processing means.

Preferably, at least two separate portions of eluate emanate from different regions of the column, e.g. the first portion may emanate from a first region and the second portion may emanate from a second region of the column, more particularly the packed column bed. More preferably, the at least two separate portions emanate from different radial regions of the column, e.g. the first portion may emanate from a first radial region and the second portion may emanate from a second radial region of the column, different from the first radial region. The term radial region herein means a region in the transverse cross-section or plane of the column, i.e. the cross-section or plane perpendicular to the central or longitudinal axis of the column. The terms radial or radially herein thus refer to a direction perpendicular to the central or longitudinal axis of the column. Preferably, the first region of the column is a radial region located substantially away from the walls of the column. Preferably, the column is a packed column having a column bed therein and a first region of the packed column is a radial region from which eluate leaves the column having passed through the most homogeneously packed portion of the column bed. Still more preferably, the first portion emanates from a central radial region of the column and the second portion emanates from a radial region located radially outward of the central radial region. Most preferably, the central radial region of the column is a region located substantially on a central axis running longitudinally through the column from the inlet to the outlet. In this way, a central core of the eluate flow, which contains a relatively higher sample concentration and better resolved components, can be directed as one portion to a detector, or other processing means, while a remainder of the eluate flow, e.g. as one or more other portions, is directed elsewhere, e.g. to one or more different processing means. Thus, preferably the first portion of eluate flow is processed differently and separately to the remainder of the eluate flow. Without being in any way limiting on the scope of the invention, this is believed to be due to the fact that a portion of eluate taken from a restricted radial region has a smaller axial spread of the sample than eluate taken from across the full width of the column due to the parabolic shape of the moving sample band.

In some embodiments, the outlet is arranged to split the flow of eluate as it leaves the column into more than two portions, For example, the outlet in such embodiments may be arranged to split the flow of eluate as it leaves the column into three or more separate portions, each portion being directed to a separate processing means than the other portions, i.e. so there are three or more separate processing means in that case.

As noted above, the concentration in a moving sample band within a packed LC column decreases as the distance from the column central axis is increased, due partly to uneven flow within and across the column diameter and partly due to diffusion and related mass transfer effects associated with transport within and around a packed bed whose own density and homogeneity can vary with the effectiveness with which the column is filled. The moving sample band also tends to have a parabolic shape. These phenomena can lead to drawbacks with sample separation efficiency, detection and resolution since a conventional column outlet gathers eluate from across the whole diameter of the column. The present invention, however, enables the flow of eluate exiting the column to be split or segmented so that a portion of the eluate flow is separated from at least another portion and the portions can be processed separately. For example, a portion of eluate containing a relatively higher concentration of a sample which, moreover, is better separated, can be selectively directed to a detector, so that an enhanced detection is provided, wherein peaks are also better resolved. That is, the component bands in a chromatographed sample become less axially spread in the central core of the column so that peaks in the chromatogram due to detection of adjacent components in a sample become better separated, or resolved. In the more preferred embodiments, the detection is thereby focused on only the portion of flow eluting from the centre core of the column, i.e. the central radial region, since that has a relatively higher concentration of a sample than the radially outer region closer to the column walls. In other words, detrimental edge effects present in the eluate flow can be reduced or eliminated by use of the present invention. In the case of preparative chromatography, the portion of eluate containing a relatively higher concentration of sample which is better separated can be selected for fractionation to give purer fractions of the sample.

From the foregoing, it is seen that the apparatus, in particular embodiments, preferably comprises a detector arranged to detect at least one portion of the eluate separately from the other portion or portions. More preferably, the detector is arranged to separately detect a portion of the eluate which has emanated from a central radial region of the column. In further particular embodiments, the apparatus comprises a fraction collector arranged to collect fractions of at least one portion of the eluate separately from the other portion or portions. In such embodiments, the apparatus may be configured to send the other portion or portions to a waste receiver. In some embodiments, the apparatus may be configured to send the other portion or portions to the inlet of a column for further chromatography of the other portion or portions. The other portion or portions preferably emanate from an outer radial region of the column, relative to the central radial region.

Although the amount of fluid available for entering, for example, a detector may be reduced as only a portion of eluate flow is selected for detection, the concentration of the sample in the detector flow path is increased compared to a conventional case. For certain detector types such as, for example, a mass spectrometer, where the amount of eluant admitted to the spectrometer should ideally be low, and in the case of certain detectors such as, for example, UV detectors, where flow effects are relevant, this is a positive benefit. In the case of a mass spectrometry (MS) detection system, since only a portion of the eluate is taken for detection with the invention, it may mean that the invention better enables the use of conventional size columns with MS detection. For example, a conventional 4.6 mm HPLC column may typically have a flow rate of around 1.5 ml/min, whereas the split flow arrangement of the invention in some embodiments may provide a portion of eluate for detection which has a flow rate of only around 0.2 ml/min, which the MS system can handle more easily, because greater vacuum power is required to evaporate greater loads of solvent. Some biodetectors, such as the DPPH antioxidant detector, require post column reagents to enter the flow stream. Maximum sensitivity is dictated by the ratio of mobile phase to DPPH reagent. Being able to split the flow exiting the column beneficially reduces the consumption of DPPH reagent, without loss in sensitivity. Multiple detection devices can also be employed, simultaneously, with minimal dead volume. These detectors can be sample destructive since a portion of the sample can still be collected in fractions for further analysis.

The ratio of the respective volumes of the different portions of eluate flow may vary, thus the flow segmentation may be tunable. The optimum flow ratio is typically dependent upon the particular experiment being conducted. Efficiency of separation systematically increases as the proportion collected from the central section decreases. This is a positive benefit since the separation can be tuned depending upon the difficulty associated in obtaining the separation, or even how much sample must flow into a sample load dependent detector, such as a mass spectrometer. Furthermore, the amount of flow from a peripheral region e.g. to waste versus that collected from a central region of the column may be varied to take into consideration the environmental burden of the process. This invention beneficially provides a tunable system that can balance economical as well as environmental benefits.

The ratio of eluate flows may be varied by various means as described in more detail below. Preferably, one portion of eluate which is processed separately is 70% or less, or 50% or less (by volume) of the total eluate, more preferably 30% or less. For example, the one portion may be 50% or less, 45% or less, 40% or less, 35% or less, 30% or less, 25% or less, 20% or less, 15% or less, 10% or less, or 5% or less of the total eluate. This one portion is preferably a portion which emanates from a central radial region of the column. This one portion is preferably a portion which is detected separately or collected separately from the other portion(s).

The ratio of the respective volumes of the different portions of eluate flow may be varied by selecting the ratio of the areas of different frit sections and/or by selecting the number and/or size of the outlet ports as described in more detail below.

The ratio of the respective volumes of the portions of eluate flow from the outlet (degree of segmentation) may be varied by adjusting the pressures and/or flow rates in one or more of the channels connected to and downstream of the exit ports (e.g. the differential outlet pressure). The differential outlet pressure may be varied, e.g., by means of a pressure or flow regulator in at least one downstream channel carrying one of the portions and/or the differential outlet pressure may be varied, e.g., by varying the lengths of tubing following the exit ports or by varying the diameter of tubing following the exit ports.

The outlet is preferably provided with a frit, wherein the frit is located such that the eluate leaving the column flows through the frit. Preferably, the frit is located within the internal diameter of the column at the outlet.

The outlet frit preferably is in a frit assembly configured to split the flow of eluate as it leaves the column into at least two separate portions. The configuration of the frit in this way enables separation of the eluate flow to be performed on-column, not post-column. In order to split the flow, preferably the outlet frit assembly is a split frit assembly (also termed herein segmented frit assembly) which comprises at least two separate frit sections, that are separated from one another by one or more flow barriers, e.g. a non-porous body may provide a flow barrier, or a non-porous coating may provide a flow barrier, e.g. wherein such coating is provided on one or more surfaces of at least one of the separate frit sections, which one or more coated surfaces abut the other frit section or sections. Thus, the eluate flowing through one or more first frit sections may provide the first portion of flow and the eluate flowing through one or more second frit sections may provide the second portion of flow since the eluate flowing through the first frit section(s) is separate from the eluate flowing through the second frit section(s) by virtue of the fluid barrier in the form of the non-porous body. The flow barrier prevents lateral, i.e. radial, flow of eluate between the frit sections as the eluate passes through the frit assembly thereby enabling flow segregation into separate portions. Since the sections of the split frit occupy different regions, especially different radial regions, of the column, the split frit determines that at least two separate portions of eluate emanate from different regions of the column, preferably different radial regions as described. On the other hand a conventional, single frit piece is less efficient because the flow of eluate through the frit is less ordered and therefore eluate which has flowed through different regions of the column bed may become mixed to an undesirable degree as it flows through the frit. The use of a split frit enables the eluate that has flowed through different regions of the column bed to exit the frit in different portions which correspond to the different regions of the column.

A preferred configuration of split frit assembly comprises at least one centre frit section, a non-porous body surrounding the at least one centre frit section and at least one outer frit section surrounding the at least one centre frit section but being separated therefrom by the non-porous body. More preferably, the split frit comprises a radially central centre frit section, a non-porous body annularly surrounding the centre frit section and an outer frit section annularly surrounding the non-porous body. Most preferably, the radially central centre frit section is located substantially on the central axis running longitudinally through the column from the inlet to the outlet. Such split frit configurations at the outlet permit the central frit section(s) to produce a portion of flow emanating from a central radial region of the column and the outer frit section(s) to produce a portion of flow emanating from a radial region located radially outward (peripherally) of the central radial region.

The centre frit section and outer frit section may be of various relative areas thereby splitting the eluate flow into portions from central and peripheral regions of different relative area. The ratio of the areas of the frit sections may thereby be a means to vary the ratio of the respective volumes of the split portions of eluate flow. For example, the ratio of the area of the outer frit section to the area of the central frit section may vary, e.g. from 90%:10% to 50%:50%, more typically from 80%:20% to 50%:50% but ratios outside these ranges may also be used. A preferred ratio of the area of the outer frit section to the area of the central frit section is from about 6:1 to about 1:1, more preferably from about 3:1 to about 1:1, still more preferably from about 2.5:1 to about 1.5:1, and most preferably is about 2:1.

The frit sections may have the same or a different density. For example, the central frit section may have a different density to the outer frit section. In one type of embodiment, the central frit section may have a lower density than the outer frit section. Thus, eluate may be controlled to flow preferentially through a frit section of lower density relative to a frit section of higher density.

The outlet frit assembly typically comprises an outer non-porous fitting, preferably made of polymer, which e.g. fits to the outlet end of the column so that the frit assembly forms a frit cap. Such an outer fitting is preferred because for example a steel frit will not seal well against a steel column wall. The polymer fitting may be made of various polymers, e.g. PTFE, ETFE, PEEK or KEL-F® polymer, more preferably PEEK. In general, any non-porous parts of the frit assembly may be made of plastics or polymer, e.g. PTFE, ETFE, PEEK or KEL-F® polymer, more preferably PEEK.

The outlet frit assembly in some other embodiments may comprise a single piece of porous frit, i.e. rather than sections of frit. The single piece of porous frit may, as in the other described embodiments, be held in an outer non-porous, preferably polymer, fitting, which e.g. fits to the outlet of the column so that the frit assembly forms a frit cap.

The outer non-porous fitting of the outlet frit assembly may have apertures to separate the flow of eluate. For example, the outer non-porous fitting may have a radially central aperture to allow through flow of a portion of eluate from the frit that emanates from a radially central region of the column, and may have one or more peripheral apertures radially outward of the central aperture to allow through flow of a portion of eluate from the frit which emanates from a peripheral radial region of the column (surrounding the radially central region). The portion of flow that emanates from the peripheral region of the column may be gathered from the outer sides of the frit, e.g. by having one or more peripheral apertures in the side walls of the outer non-porous fitting.

The outlet frit assembly is preferably of circular outer shape to fit a circular cross section column, although frit assemblies of other shapes may be used depending on the column shape for example.

The material of the outlet frit may be conventional frit material as used in LC, e.g. steel. Thus, the frit may simply be configured in the split manner described herein to split the eluate flow that flows through it. For example, the frit material, thickness (depth), and porosity may be conventional as used in LC systems. For example, a frit of typical thickness of 0.25 to 2 mm may be used. For example, a frit with nominal 2 µm porosity may be used. However, frits of other porosities can be used, e.g. in the range nominally of 0.1-20 µm. The non-porous body of the split frit embodiments is preferably made of a plastics or polymer, e.g. PTFE, ETFE, PEEK or KEL-F® polymer, more preferably PEEK but may be made of metal, e.g. stainless steel. Such non-porous materials may also be provided as a thin layer or coating on one or more surfaces of one or more frit sections that abut another frit section to provide a flow barrier. The non-porous flow barrier alternatively could be made of a metal. Such a metal barrier could be formed by sputtering as a thin layer or coating on one or more surfaces of one or more frit sections that abut another frit section. Such thin layer or coating flow barriers may have an advantage of low drag on the eluate flow.

The width (i.e. measured in the radial direction) of the flow barrier or non-porous body is preferably small compared to the width of the frit sections, i.e. is preferably lower than the width of each of the frit sections. It is preferably as small as possible, ideally micron sized. Thus, any possible drag on the flow of separated components that may be caused by the presence of the flow barrier in the eluate flow, or any dead zone effects behind the flow barrier, which may thereby be minimised. It will be appreciated, however, that the barrier should not be so thin that segregation of the flow into separate portions is not effectively achieved.

In certain embodiments, the outlet may be provided with a plurality of capillaries (exit capillaries) to channel the eluate flow, wherein one or more capillaries are arranged to channel the first portion of the flow and one or more other capillaries are arranged to channel the second portion of the flow. Thus, the first and second portions are channeled in separate capillaries and thus are split from each other. The exit capillaries are preferably separated from one another by a non-porous material, e.g. plastics. In this way, the flow is directed only along the separate capillaries. Preferably, frits are provided in the exit capillaries. In a preferred arrangement of such exit capillaries, a radially central first capillary may be surrounded, preferably annularly surrounded, by a plurality of second capillaries (e.g. bundled capillaries, which may be bundled capillaries in an annular arrangement), wherein the radially central first capillary channels the first portion of eluate flow and the plurality of second capillaries channel the second portion of eluate flow separately from the first portion.

Preferably, the column inlet and outlet are each located at an end of the column, i.e. at opposite ends of the column. The column in use preferably has a flow distributor at its outlet end (outlet flow distributor). The outlet flow distributor is preferably configured to convey in separate channels therein the at least first and second portions of the eluate flow, i.e. the first portion being conveyed in one or more separate channels from the second portion etc. The flow distributor is thus effectively a distributor for the eluate flow. The outlet flow distributor may be provided as a column end fitting, i.e. a detachable end fitting which is releasably fitted to the column outlet end in use. Alternatively, the outlet flow distributor may be made integral with the end of the column. A preferred arrangement is to have the outlet flow distributor as a separate end fitting part that is fitted to the end of the column in use. However, it will be appreciated that in other embodiments it is possible that the flow distributor be made integrally with the column with a plurality of separate channels to convey the at least first and second portions of the eluate flow. In such integral embodiments, the flow distributor is not a separate part. Herein, although the preferred embodiment of a separate end fitting will be primarily used to illustrate the flow distributor, the features of such an end fitting generally also apply to the case where the flow distributor is made integrally with the column end.

The flow distributor at the outlet is configured to have a plurality of separate channels therein to separately convey the at least first and second portions of the eluate flow, e.g. which may have been split upstream at the outlet, such as by the split frit assembly described, or the flow distributor alone may be configured to split the eluate flow into the separate portions, e.g. where a standard (non-split) frit is used at the outlet. The flow distributor thus has a plurality of separate channels for the at least first and second portions of the eluate to flow in. The eluate may thereby be split into separate portions which are distributed to different processing means. As described above, the flow distributor is preferably provided as an end fitting, wherein the end fitting includes the plurality of separate channels.

The separate channels of the outlet flow distributor, e.g. end fitting, preferably are arranged to convey portions of eluate flow which emanate from different regions of the column, more preferably different radial regions of the column as described. The separate channels of the flow distributor may comprise a first set of at least one channel (preferably one first channel) which is located in the distributor so that in use it lies in a first region, preferably first radial region, of the column. For example, in the case of a flow distributor which is in the form of an end fitting, the first set of at least one channel of the end fitting is located in the fitting such that when it is fitted to the outlet end of the column the first set lies in a first region, preferably first radial region, of the column. The first radial region is preferably the central radial region of the column, more preferably located substantially on a central axis running longitudinally through the column, and a first set of at least one channel is herein termed a central channel set in that case. The first or central channel set conveys a first portion of the eluate flow. The first set of at least one channel (e.g. central channel set) is preferably radially aligned with a central frit section of a split frit assembly, where a split frit assembly is employed. The separate channels of the outlet flow distributor may comprise a second set of at least one channel (preferably a plurality of channels) which is located in the distributor so that in use it lies in a second region, preferably second radial region, of the column. For example, in the case of an end which is in the form of an end fitting, the second set of at least one channel (preferably a plurality of channels) of the end fitting is located in the fitting such that when it is fitted to the outlet end of the column the second set of at least one channel lies in a second region, preferably second radial region, of the column. The second radial region is preferably a radial region located radially outward or peripherally of the central radial region and a second set of at least one channel is herein termed an outer or peripheral channel set in that case. The second or outer or peripheral channel set conveys a second portion of the eluate flow. The second set of at least one channel (e.g. outer or peripheral channel set) is preferably radially aligned with an outer or peripheral frit section of a split frit assembly, where a split frit assembly is employed. A third set and optionally further sets of channel(s) may be included in the flow distributor in other embodiments, e.g. where third and optionally further portions of eluate are separated for processing. In preferred embodiments, the first channel set for directing a first portion of the eluate comprises a radially central channel and the second set comprises a plurality of outer channels radially outward of the central channel. However, it will be appreciated that in embodiments the first set may comprise a plurality of central channels, i.e. in a central radial region, and a plurality of outer channels radially outward of the first set of channels. The flow from the plurality of central channels in such cases may be gathered together and processed as a first portion separately from the flow from the plurality of outer channels which may be gathered together and processed as a second portion.

Preferably, the flow distributor is arranged very close to or, most preferably, in contact with the frit assembly such that the portions of eluate which have passed through the frit assembly (especially the split frit) having emanated from different radial regions of the column bed pass to the respective sets of channels in the distributor, e.g. first and second portions of eluate which have passed through the frit assembly pass respectively into first and second sets of channels in the flow distributor. By arranging the flow distributor in direct contact with the frit assembly it is less likely to introduce voids. The flow distributor in use may sit flush against the frit surface. The flow distributor in use may sit in contact with one or more of the non-porous parts of the frit assembly so that the one or more non-porous parts provide a seal between the frit (e.g. frit sections) and flow distributor thereby sealing adjacent portions of eluate flow from each other. For example, the non-porous outer frit fitting and/or non-porous flow barrier (which separates the porous frit sections), may seal against the flow distributor to thereby keep the portions of eluate separate.

The channels through the outlet flow distributor, preferably end fitting, preferably each have an exit or outlet port at their downstream end, to which can be connected exit plumbing to carry eluate, e.g. to the processing means. The number of channels may or may not equal the number of exit ports, for example in some embodiments any two or more channels could merge within the flow distributor to share an exit port. Preferably, however, the number of channels is equal to the number of exit ports.

Preferably, the outer or peripheral channels and their ports are arranged symmetrically about the central axis of the column. For example, the outer or peripheral channels and their ports may be equally spaced apart and/or equidistant from the central channel and port. However, the outer or peripheral channels and their ports could be arranged un-symmetrically.

Preferably, the outlet flow distributor comprises one central channel and from 2 to 12 outer channels, i.e. 2, 3, 4, 5, 6, 7, 8, 9, 10, 11, or 12 outer channels, more preferably one central channel and from 3 to 6 outer channels. An outlet flow distributor having 3, 4, 5 or 6 outer channels is a good example. However, these numbers are not limiting on the invention.

As preferred examples, in a first preferred embodiment, the outlet flow distributor, preferably end fitting, comprises one central channel and three outer channels (i.e. a four channel or port configuration). In a second preferred embodiment, the flow distributor comprises one central channel and six outer channels (i.e. a seven channel or port configuration). The number of channels and the number of ports can be varied, e.g. four port, five port, six port, seven port, eight port, nine port, ten port, eleven port, or twelve port configurations may be used, or indeed configurations with even higher numbers of ports may be used.

With regard to the number of central exit ports versus the number of peripheral exit ports, the outlet flow distributor, preferably end fitting, in the above-mentioned first preferred embodiment may have one central exit port at the centre and three peripheral exit ports surrounding it but it should be understood that the present invention contemplates any number of peripheral exit ports, e.g. one or more peripheral exit ports. Preferred examples may have from 3 to 12, more preferably 3 to 10, peripheral exit ports, particularly 3, 4, 5, 6, 7 or 8 peripheral exit ports. A flow distributor, preferably end fitting, with 3, 4, 5 or 6 peripheral exit ports is a good example. Furthermore, the present invention contemplates any number of central exit ports (i.e. those ports which transmit a flow of eluate from a central radial region), e.g. one or more central exit ports. Preferably, there is one central exit port. The exit ports in general may be located in the end or sides of the body of the flow distributor, preferably the end. The outer exit port or ports may be located in the end or sides of the flow distributor. The central exit port or ports may be located in the end or sides of the flow distributor but preferably the end. In some embodiments, the portion of flow that emanates from the peripheral region of the column may be gathered from the outer sides of the frit and e.g. directed through the outer exit port or ports located in the sides of the flow distributor. The portion of flow that emanates from the central region of the column may be gathered from the centre of the frit and e.g. directed through a central exit port or ports located in the end of the flow distributor.

Selecting the number and the size of the exit port(s) channeling each portion of the eluate may be a means to vary the ratio of the respective volumes of the portions of eluate flow (i.e. the degree of segmentation). The ratio of the respective volumes of the portions of eluate flow from the outlet (degree of segmentation) may alternatively or also be varied by adjusting the pressures in the downstream channels following the exit ports (i.e. the differential outlet pressure). The differential outlet pressure may be varied, e.g., by varying the lengths of tubing or diameter of tubing following the exit ports.

In use, one or more of the exit ports may be closed, i.e. blocked off, so that eluate does not flow therethrough but instead is caused to flow through the remaining open ports.

A portion of the flow of eluate comprises all the eluate which is gathered from the outlet and sent to a particular processing means by a particular route. A portion of eluate may thus comprise eluate that has been gathered from one or more ports, e.g. a plurality of peripheral ports, of the flow distributor and collectively sent to a particular processing means.

The outlet end fitting may be of similar external dimensions to a conventional end fitting. The end fitting may be either hand tightened or tightened with the aid of a tool if necessary to the end of the column at the column outlet. The outlet end fitting is preferably fitted to the outlet end of the column by a screw connection, or may be push fitted, or may connect using another type of connection. As with many conventional types of end fittings for analytical columns, e.g. for HPLC, a typical connection for the end fitting on the column comprises an external screw thread on the outlet end of the column and an internal screw thread inside the end fitting. In such arrangements, the end fitting thus screws onto the end of the column and covers the outlet. In other embodiments, the outlet end fitting may be fitted internally in the column end, e.g. with certain types of self-packed columns and axial compression columns. In such embodiments, the end fitting may be push (friction) fitted into the column end and optionally may carry a sealing means, such as one or more sealing rings or o-rings, on its outer surface to seal against the internal surface of the column wall. The outlet end fitting may be made of any suitable material. The end fitting may be made of metal, preferably stainless steel, especially where it is fitted to a metal column, e.g. stainless steel column, preferably by a screw thread or by using a SWAGELOK® type fitting. In other cases, e.g. where the column is glass, the end fitting may be made from other suitable materials, e.g. plastics, for instance PEEK.

It will be appreciated that a key feature of the invention is that separation of the eluate flow is performed on-column, and not post-column as is the conventional method. This is achieved by the features of the invention described herein, such as the split frit assembly and flow distributor.

The column outlet may split the eluate flow leaving the column into more than two portions, e.g. three, four or more portions. Preferably, the outlet splits the eluate flow into two portions, which provides a low cost, elegant and advantageous embodiment of the invention as illustrated in more detail herein.

The split portions of eluate leaving the outlet may be further directed, i.e. downstream of the flow distributor, by eluate directing means to the processing means. Preferably, the eluate directing means for directing the portions of the eluate to the processing means receives the flow of eluate after it is split at the outlet, e.g. after the flow distributor, and typically comprises a plurality of conduits, e.g. tubing. Each outlet port of the flow distributor through which eluate is flowed in use preferably has a conduit attached thereto. Preferably, the at least two separate portions of eluate are directed in separate channels or conduits to their respective separate processing means. Suitable tubing for this purpose may comprise any standard or conventional tubing for use in liquid chromatography, e.g. plastics tubing (preferably PEEK tubing), or metal tubing (preferably steel tubing). Each portion of eluate flow is preferably directed through its own set of one or more conduits to a respective processing means.

Preferably, the inlet and outlet are each located at an end of the column, i.e. the inlet and outlet are located at opposite ends of the column. The inlet is configured to introduce a flow of mobile phase into the column carrying a sample, whereby the sample separates into components as it advances longitudinally through the column from the inlet to the outlet carried by the mobile phase. The inlet may be a conventional inlet for column chromatography. In other words, the invention may be implemented by making modifications as described herein only at the outlet end of the column. The sample may, for example, be introduced into the column at the inlet across the width of the column, either via single inlet port or via multiple inlet ports (such as an inlet or head flow distributor having multiple inlet ports spaced across the width of the column to more evenly distribute flow across the column width) or at a restricted radial region of the column, e.g. by central point injection (CPI), or at a restricted radial region of the column using a curtain flow process that is achieved by employing a split flow or segmented flow fitting (similar to the outlet end fitting), at the column inlet. In such cases, the sample may thereby be introduced preferentially (i.e. in relatively larger amount) via one or more of the ports, with other ports introducing less or no sample in the mobile phase. The portion of mobile phase introduced with sample preferentially contained therein may thus flow through the column in a radially restricted manner bounded by the portion of mobile phase introduced containing less or no sample.

A frit may be used in the column at the inlet as for many types of conventional LC.

In certain preferred embodiments, the inlet is configured to introduce the flow of mobile phase into the column in at least two separate portions which are independently controllable, and to introduce the portions into different radial regions of the column, such that the portions flow longitudinally through the column in different radial regions. Preferably, the sample concentrations in each portion or the flow velocity of each portion or both are independently controllable. The composition of the mobile phase portions may be controllable. Thereby, the mobile phase portions may be of the same or different composition, e.g. the same or different solvents. One portion, e.g. a radially peripheral portion, may even be a non-solvent or at least a solvent having lower solubility for the sample to be separated (e.g. water), thereby promoting the containment of sample in the other, e.g. radially central, portion.

Preferably, the sample concentrations in each portion are independently controllable whereby the sample to be separated is contained in one of the portions in a higher concentration than in the other portion(s).

The outlet is preferably configured such that the portions of mobile phase that have been flowed through the column in different regions by means of the segmented inlet are split from each other at the outlet to provide the separate portions of eluate. The eluate at the outlet which is separated into two or more portions thus may include an eluate portion which comprises at least some, or all, of the portion of mobile phase which has flowed through the column containing the relatively higher amount of sample (or substantially all the sample). The eluate at the outlet which is separated into two or more portions thus may include an eluate portion which comprises at least some, or all, of the portion of mobile phase which has flowed through the column containing the relatively lower amount of sample (or substantially no sample). Such portion may be recycled for example.

Preferably, the inlet is configured to introduce a flow of mobile phase into the column in at least two separate portions: at least a first portion of the flow and a second portion of the flow. Preferably, a first mobile phase portion contains sample at a higher concentration than the second portion. Thus, in such cases, the sample concentration in each portion is independently controllable. This may be achieved in a simple case by arranging a sample injection valve to inject sample into one of the portions (a first portion) in a controllable amount but not into the other portion(s), for example by arranging the sample valve on a line which only one of the portions flows through before the column inlet. The other portion(s) each may have no sample injection valve on their line which the portion flows through before the column inlet, such that the other portion contains only solvent, or may have a separate sample injection valve on their line for introducing a different amount of sample (including the case of no sample) to that injected into the first portion.

The method provided by the invention accordingly may comprise providing to an inlet of a chromatography column at least two separate portions of mobile phase, at least one of which contains a sample to be separated into components in a higher concentration than in the other portion(s); introducing the at least two separate portions of mobile phase into different radial regions of the column; flowing the portions of mobile phase longitudinally through the column in the different radial regions from the inlet of the column to an outlet of the column to separate the sample into components. Preferably, the method comprises controlling the transverse diffusion of sample from the portion having higher sample concentration by the flow of the other portion(s).

The sample to be separated is preferably contained in one of the portions in a higher concentration than in the other portion(s) at least at the inlet where the portions are introduced into the column. The sample being contained in one of the mobile phase portions in a higher concentration than in the other portion(s) includes the preferred case wherein all, i.e. substantially all, of the sample is contained in one of the mobile phase portions and the other portion(s) does not contain, i.e. substantially does not contain, any sample (i.e. the other portion(s) is/are solvent only), preferably at least at the inlet where the portions are introduced into the column and more preferably also at the outlet. The transverse diffusion of sample from the portion having higher sample concentration may be constrained by the flow of the other portion(s).

The invention in such preferred embodiments thus allows sample to be introduced to the inlet of the column preferentially contained within one of the portions of mobile phase and that portion to be introduced to and flow through a restricted radial region, preferably the central region, of the column. Such a portion containing a higher sample concentration is herein also termed the sample flow. A so-called curtain flow may then be provided by one or more of the other portions of mobile phase, preferably flowing through the wall or peripheral region of the column (annularly surrounding the central region), which restricts the transverse migration (i.e. diffusion) of the sample, e.g. migration to the wall. In certain preferred embodiments, the curtain flow is in the form of an annular band of mobile phase which flows around the sample flow that is in the form of a central band of mobile phase. When utilised in conjunction with the split or segmented flow at the outlet, the sample exiting the column thereby exits concentrated in a particular radial region, preferably the central region. The detection of a sample can thereby be enhanced by containing and concentrating the sample within a restricted region of the column, preferably the central region since that is typically the most homogeneously packed region in a packed column and where sample separation efficiency is also typically highest. In essence therefore, such embodiments function to contain the sample flowing through the chromatography column within a defined region, preferably central, cylindrical region, of the column bed, to enhance detection of components eluting from the column. These embodiments thus function to reduce the transverse diffusion of sample within the column as it advances longitudinally through the column. Improvements in the signal-to-noise ratio (S/N) of chromatographic peaks may thus be achieved through the containment of sample in a smaller volume of eluate. A flow of mobile phase in a wall or peripheral radial region of the column advantageously acts to prevent sample in a flow of mobile phase in a central radial region of the column from migrating to the column wall. In this way, collection and/or detection of the central portion of mobile phase eluate alone, in which the sample may be substantially constrained by the function of the present invention, may lead to up to 100% effective use of the sample (i.e. as little as 0% of the sample being wasted in the peripheral portion). In such embodiments, effectively a narrower diameter column is being employed for the separation and analysis, but with the pressure drop of a wider bore column, at the higher flow velocities of the wider bore bed and with the extra dead volume advantages of a larger volume bed.

In a further advantage of such embodiments, the linear flow velocities of the different mobile phase portions can be controlled. The flow velocities can be controlled either by using separate pumps for the portions (a separate pump for each portion), or by other means, for example by placing flow restrictors in the tubing carrying each portion (i.e. to provide differential pressure between the tubing carrying each portion, for example between peripheral fluid lines and a central fluid line).

The flow velocities may be arranged to be substantially the same. In a conventional column with a single inlet port, the sample flow is focused on the central region of the column bed, in which flow speeds are naturally higher anyway. This leads to a bowl shaped sample band, with faster moving sample in the central region and slower moving sample in the peripheral or wall region. The described embodiments of the invention can overcome or reduce this deficiency by arranging for separate flows of different mobile phase portions, such as a central flowing portion and an additional peripheral flowing portion, in which their flow velocities can be arranged to be substantially the same, thereby providing a flow velocity profile in the transverse cross section which is substantially flat or at least significantly flatter than in the conventional case. Flat flow profiles can deliver peaks to the outlet in a narrower band of time (i.e. narrower peak widths in the chromatogram) and thus improve resolution.

It has been found that when such curtain flow is applied which is solvent only the sample may not touch the wall at all. It has been found that up to 100% of the sample can be arranged to elute from the central region of the column, and down to 0% elute peripheral to this region. Thus, with the curtain flow, there may be down to substantially no sample loss from the central region and there may be up to substantially 100% recovery of solvent used in the peripheral curtain flow. Accordingly, sample can be arranged to elute as a plug through the centre of the column. This provides one of the main advantages of the curtain flow, which is the gain in sample concentration, which can be made use of by channeling the concentrated sample from the central region via a central outlet of lower volume flow to a separate processing means, preferably a sample collection device or detector. The up to 100% recovery of solvent used in the curtain flow portion of mobile phase may be recycled leading to numerous environmental benefits.

In embodiments wherein the mobile phase is introduced into the column as two or more separate portions into different radial regions of the column, the inlet is preferably configured to introduce a flow of mobile phase into the column such that the mobile phase is provided in at least two separate portions wherein each portion is preferably introduced separately, e.g. via its own set of one or more introduction channels (such inlet being herein termed a segmented inlet). In certain preferred embodiments, a portion of the mobile phase flows into and through the column in a different region of the column from another portion and more preferably is detected or collected separately to the other portion.

Preferably, the segmented inlet is configured to introduce a flow of mobile phase into the column in at least two separate portions: at least a first portion of the flow and a second portion of the flow. Preferably, a first mobile phase portion contains sample at a higher concentration than the second portion. The first and second portions of the eluate flow are preferably the outflow of the first and second portions respectively of the mobile phase which has flowed through the column. Similarly, the first and second regions from which the first and second portions of the eluate flow emanate are preferably respectively the first and second regions of the column through which the first and second portions of mobile phase have flowed.

Preferably, using the segmented inlet at least two separate portions of mobile phase are introduced to different regions of the column, e.g. the first portion may be introduced to a first region and the second portion may be introduced to a second region of the column, more particularly the column bed. More preferably, the at least two separate portions may be introduced to different radial regions of the column, e.g. the first portion may be introduced to a first radial region and the second portion may be introduced to a second radial region of the column, different from the first radial region. Preferably, the first region of the column is a radial region located substantially away from the walls of the column. Preferably, the column is a packed column having a column bed therein and a first region of the packed column is a radial region through which mobile phase passes longitudinally through the most homogeneously packed portion of the column bed. Still more preferably, the first portion of mobile phase is introduced to and flows through a central radial region of the column and the second portion is introduced to and flows through a radial region located radially outward of the central radial region, i.e. a peripheral region. Most preferably, the central radial region of the column is a region located substantially on a central axis running longitudinally through the column from the inlet to the outlet. In this way, a central core of the mobile phase flow, which preferably contains a higher sample concentration and better resolved components, can be directed via the outlet as one portion to a detector, or other processing means, while a remainder of the flow, e.g. as one or more other portions, is directed via the outlet elsewhere, e.g. to one or more different processing means. Thus, preferably the first portion of flow is processed differently and separately to the remainder of the flow. In some embodiments, the inlet is arranged to introduce the flow of mobile phase into the column in more than two portions, For example, the inlet in such embodiments may be arranged to introduce the flow to the column in three or more separate portions.

As noted above, the concentration in a moving sample band within a packed LC column decreases as the distance from the column central axis is increased, due partly to uneven flow within and across the column diameter and partly due to diffusion and related mass transfer effects associated with transport within and around a packed bed whose own density and homogeneity can vary with the effectiveness with which the column is filled. The moving sample band also tends to have a parabolic shape. These phenomena can lead to drawbacks with sample separation efficiency, detection and resolution since a conventional column outlet gathers eluate from across the whole diameter of the column. The segmented inlet, however, enables the flow of mobile phase entering the column to be segmented so that a portion of the flow is separated from at least another portion and the portions can flow substantially in parallel fashion along the column. For example, a portion of mobile phase containing a relatively higher concentration of a sample can be selectively flowed through the central region of the column and advantageously separately directed at a detector, so that an enhanced detection is provided, wherein peaks are also better resolved. That is, the component bands in a chromatographed sample become less axially spread in the central core of the column so that peaks in the chromatogram due to detection of adjacent components in a sample become better separated, or resolved. In the more preferred embodiments, the detection is thereby focused on only the portion of flow eluting from the centre core of the column, i.e. the central radial region, since that has a relatively higher concentration of a sample than the radially outer region closer to the column walls. The outlet of the column is thus preferably configured to split the flow of eluate leaving the column into different portions which emanate from different regions of the column, the different portions being processed separately.

The segmented inlet thereby preferably provides a flow of mobile phase (more preferably of solvent only), referred to herein as a curtain flow, which is provided by one of the portions of mobile phase, preferably introduced in a radially outer region of the column to thereby flow through the column in a radially outer region of the column. This curtain flow preferably moves at a comparable, more preferably substantially the same, linear velocity as the central portion of mobile phase e.g. containing a relatively higher concentration of a sample (more preferably containing all the sample), referred to herein as a sample flow, preferably introduced in a radially central region of the column to thereby flow through the column in a radially central region of the column. This matching of velocities thereby provides a resistance to the transverse diffusion of the sample from the sample flow within the column. In this way, a central flowing mobile phase portion is maintained separated from a peripheral flowing mobile phase portion.

The apparatus in such embodiments thus preferably is arranged for separate flows of different mobile phase portions, such as a central flowing portion and an additional peripheral flowing portion, in which their flow velocities can be arranged to be substantially the same, thereby providing a flow velocity profile in the transverse cross section which is substantially flat or much flatter than in the conventional case. Flat flow profiles also deliver peaks to the outlet in a narrower band of time (i.e. narrower peak widths in the chromatogram). In certain embodiments, there may be a lesser flow velocity in the central region relative to the peripheral region.

As the mobile phase flow reaches the outlet of the column the eluate is preferably separated in such a way that substantial mixing of the portions of mobile phase flow is avoided. At the outlet of the column the eluate is preferably split such that the curtain flow is kept separate from the sample flow. In this way, for example, a central flow containing relatively higher sample concentration can be directed to a detector while a peripheral flow (curtain flow) is directed elsewhere. This can enhance the lower limit of detection for components being chromatographed and improve the peak capacity within a chromatographic assay, with the benefit that improved assay performance is delivered.

The ratio of the respective volumes of the different portions of mobile flow may be varied using the segmented inlet, thus the flow segmentation may be tunable. The optimum flow ratio is typically dependent upon the particular experiment being conducted. Furthermore, the amount of flow through a peripheral region containing little or no sample versus the amount of flow through a central region of the column containing the sample may be varied to take into consideration of the environmental burden of the process. This invention beneficially provides a tunable system that can balance economical as well as environmental benefits.

The ratio of flow using the segmented inlet may be varied by various means as described in more detail below. Preferably, one portion of mobile phase is 70% or less (by volume), or 50% or less, more preferably 30% or less of the total mobile phase. For example, the one portion may be 50% or less, 45% or less, 40% or less, 35% or less, 30% or less, 25% or less, 20% or less, 15% or less, 10% or less, or 5% or less of the total mobile phase. This one portion is preferably a portion which flows through a central radial region of the column.

The ratio of the respective volumes of the different portions of mobile phase flow through the segmented inlet may be varied by selecting the ratio of areas of different frit sections and/or by selecting the number and/or size of the inlet ports as herein described in more detail below.

The segmented inlet is preferably provided with an inlet frit, wherein the frit is located such that the mobile phase entering the column flows through the frit. Preferably, the inlet frit is located within the internal diameter of the column at the inlet.

The inlet frit preferably is in an inlet frit assembly configured to separate the flow of mobile phase as it enters the column into at least two separate portions. In order to split the flow, preferably the inlet frit assembly is a split frit assembly (also termed herein segmented frit assembly) which comprises at least two separate frit sections, that are separated from one another by one or more flow barriers, e.g. a non-porous body may provide a flow barrier, or a non-porous coating may provide a flow barrier, e.g. wherein such coating is provided on one or more surfaces of at least one of the separate frit sections, which one or more coated surfaces abut the other frit section or sections. Thus, the mobile phase flowing through one or more first frit sections may provide the first portion of mobile phase flow and the mobile phase flowing through one or more second frit sections may provide the second portion of mobile phase flow since the mobile phase flowing through the first frit section(s) is separate from the mobile phase flowing through the second frit section(s) by virtue of the fluid barrier in the form of the non-porous body. The flow barrier prevents lateral, i.e. radial, flow of mobile phase between the frit sections as the mobile phase passes through the frit assembly thereby enabling flow segregation into separate portions. Since the sections of the split frit occupy different regions, especially different radial regions, of the column, the split frit determines that at least two separate portions of mobile phase are introduced into different regions of the column, preferably different radial regions as described. On the other hand a conventional, single frit piece is less efficient because the flow of mobile phase through the frit is less ordered and therefore mobile phase may become mixed therein to an undesirable degree as it flows through the frit.

A preferred configuration of inlet split frit assembly comprises at least one centre frit section, a non-porous body surrounding the at least one centre frit section and at least one outer frit section surrounding the at least one centre frit section but being separated therefrom by the non-porous body. More preferably, the split frit comprises a radially central centre frit section, a non-porous body annularly surrounding the centre frit section and an outer frit section annularly surrounding the non-porous body. Most preferably, the radially central centre frit section is located substantially on the central axis running longitudinally through the column from the inlet to the outlet. Such split frit configurations permit the central frit section(s) to produce a portion of flow to a central radial region of the column and the outer frit section(s) to produce a portion of flow to a radial region located radially outward (peripherally) of the central radial region.

The centre frit section and outer frit section may be of various relative areas thereby splitting the mobile phase flow into portions from central and peripheral regions of different relative area. The ratio of the areas of the frit sections may thereby be a means to vary the ratio of the respective volumes of the portions of mobile phase flow. For example, the ratio of the area of the outer frit section to the area of the central frit section may vary, e.g. from 90%:10% to 50%:50%, more typically from 80%:20% to 50%:50% but ratios outside these ranges may also be used. A preferred ratio of the area of the outer frit section to the area of the central frit section is from about 6:1 to about 1:1, more preferably from about 3:1 to about 1:1, still more preferably from about 2.5:1 to about 1.5:1, and most preferably is about 2:1.

The frit sections may have the same or a different density. For example, the central frit section may have a different density to the outer frit section. In one type of embodiment, the central frit section may have a lower density than the outer frit section. Thus, mobile phase may be controlled to flow preferentially through a frit section of lower density relative to a frit section of higher density.

The inlet frit assembly typically comprises an outer non-porous fitting, preferably made of polymer, which e.g. fits to the inlet end of the column so that the frit assembly forms a frit cap. Such an outer fitting is preferred because for example a steel frit will not seal well against a steel column wall. The polymer fitting may be made of various polymers, e.g. PTFE, ETFE, PEEK or KEL-F® polymer, more preferably PEEK. In general, any non-porous parts of the frit assembly may be made of plastics or polymer, e.g. PTFE, ETFE, PEEK or KEL-F® polymer, more preferably PEEK, or may be made of metal, e.g. stainless steel.

The inlet frit assembly in some other embodiments may comprise a single piece of porous frit, i.e. rather than sections of frit. The single piece of porous frit may, as in the other described embodiments, be held in an outer non-porous, preferably polymer, fitting, which e.g. fits to the outlet of the column so that the frit assembly forms a frit cap.

The outer non-porous fitting may have apertures to allow separate introduction of the flow of mobile phase. For example, the outer non-porous fitting may have a radially central aperture to allow through flow of a portion of mobile phase through the frit to a radially central region of the column, and may have one or more peripheral apertures radially outward of the central aperture to allow through flow of a portion of mobile phase through the frit to a peripheral radial region of the column (surrounding the radially central region). The portion of mobile phase flow to the peripheral region of the column may be introduced from the outer sides of the frit, e.g. by having one or more peripheral apertures in the side walls of the outer non-porous fitting.

The inlet frit assembly is preferably of circular outer shape to fit a circular cross section column, although frit assemblies of other shapes may be used depending on the column shape for example.

The material of the inlet frit may be conventional frit material as used in LC, e.g. steel. Thus, the frit may simply be configured in the split manner described herein to split the eluate flow that flows through it. For example, the frit material, thickness (depth), and porosity may be conventional as used in LC systems. For example, a frit of typical thickness of 0.25 to 2 mm may be used. For example, a frit with 2 μm porosity may be used. The non-porous body of the split frit embodiments is preferably made of a plastics or polymer, e.g. PTFE, ETFE, PEEK or KEL-F® polymer, more preferably PEEK, or may be made of metal, e.g. stainless steel. Such non-porous materials may also be provided as a thin layer or coating on one or more surfaces of one or more frit sections that abut another frit section to provide a flow barrier. The non-porous flow barrier alternatively could be made of a metal. Such a metal barrier could be formed by sputtering as a thin layer or coating on one or more surfaces of one or more frit sections that abut another frit section. Such thin layer or coating flow barriers may have an advantage of low drag on the flow.

The width (i.e. measured in the radial direction) of the flow barrier or non-porous body is preferably small compared to the width of the frit sections, i.e. is preferably lower than the width of the frit sections. Thus, any possible drag on the flow of separated components that may be caused by the presence of the flow barrier in the flow, or any dead zone effects behind the flow barrier, may thereby be minimised. It will be appreciated, however, that the barrier should not be so thin that segregation of the flow into separate portions is not effectively achieved.

The segmented inlet in use preferably has an inlet flow distributor at its inlet end, e.g. to produce the curtain flow regime around a central flow. The inlet flow distributor is preferably similar in structure to the outlet flow distributor described above. The inlet flow distributor is preferably configured to convey in separate channels therein the at least first and second portions of the mobile phase flow, i.e. the first portion being conveyed in one or more separate channels from the second portion etc. The inlet flow distributor is thus effectively a distributor for the mobile phase flow. The inlet flow distributor may be provided as a column end fitting, i.e. a detachable end fitting which is releasably fitted to the column outlet end in use. Alternatively, the inlet flow distributor may be made integral with the inlet end of the column. A preferred arrangement is to have the inlet flow distributor as a separate end fitting part that is fitted to the end of the column in use. However, it will be appreciated that in other embodiments it is possible that the flow distributor be made integrally with the column with a plurality of separate channels to convey the at least first and second portions of the mobile phase flow. In such integral embodiments, the flow distributor is not a separate part. Herein, although the preferred embodiment of a separate end fitting will be primarily used to illustrate the inlet flow distributor, the features of such an end fitting generally also apply to the case where the flow distributor is made integrally with the column end.

The inlet flow distributor is configured to have a plurality of separate channels therein to separately convey the at least first and second portions of the mobile phase flow. The inlet flow distributor alone may be configured to introduce the mobile phase flow in the separate portions, e.g. where a standard (non-split) frit is used at the inlet. The inlet flow distributor thus has a plurality of separate channels for the at least first and second portions of the mobile phase to flow in. The separate portions of mobile phase may thereby be distributed to different regions of the column. As described above, the flow distributor is preferably provided as an end fitting, wherein the end fitting includes the plurality of separate channels.

The separate channels of the inlet flow distributor, e.g. end fitting, preferably are arranged to convey portions of mobile phase flow which are introduced to different regions of the column, more preferably different radial regions of the column as described. The separate channels of the flow distributor may comprise a first set of at least one channel (preferably one first channel) which is located in the distributor so that in use it lies in a first region, preferably first radial region, of the column. For example, in the case of an inlet flow distributor that is in the form of an end fitting, the first set of at least one channel of the end fitting is located in the fitting such that when it is fitted to the inlet end of the column the first set lies in a first region, preferably first radial region, of the column. The first radial region is preferably the central radial region of the column, more preferably located substantially on a central axis running longitudinally through the column, and a first set of at least one channel is herein termed a central inlet channel set in that case. The first or central channel set conveys a first portion of the mobile phase flow. The first set of at least one channel (e.g. central channel set) is preferably radially aligned with a central frit section of a split inlet frit assembly, where a split frit assembly is employed. The separate channels of the inlet flow distributor may comprise a second set of at least one channel (preferably a plurality of channels) which is located in the distributor so that in use it lies in a second region, preferably second radial region, of the column. For example, in the case of an flow distributor that is in the form of an end fitting, the second set of at least one channel (preferably a plurality of channels) of the end fitting is located in the fitting such that when it is fitted to the inlet end of the column the second set of at least one channel lies in a second region, preferably second radial region, of the column. The second radial region is preferably a radial region located radially outward or peripherally of the central radial region and a second set of at least one channel is herein termed an outer or peripheral inlet channel set in that case. The second or outer or peripheral channel set conveys a second portion of the mobile phase flow. The second set of at least one channel (e.g. outer or peripheral inlet channel set) is preferably radially aligned with an outer or peripheral frit section of a split inlet frit assembly, where a split frit assembly is employed. A third set and optionally further sets of channel(s) may be included in the flow distributor in other embodiments, e.g. where third and optionally further separate portions of mobile phase are introduced to the column. In preferred embodiments, the first channel set for introducing a first portion of the mobile phase comprises a radially central channel and the second set comprises a plurality of outer channels radially outward of the central channel. However, it will be appreciated that in embodiments the first set may comprise a plurality of central channels, i.e. in a central radial region, and a plurality of outer channels radially outward of the first set of channels. In other embodiments, there may be no central channel. The mobile phase flow through the plurality of central channels in such cases may be gathered together and ultimately processed as a first portion separately from the flow from the plurality of outer channels which may be gathered together and processed as a separate, second portion.

Preferably, the channels of the inlet flow distributor are substantially in the same radial positions as the channels of the outlet flow distributor.

Preferably, the inlet flow distributor is arranged very close to or, most preferably, in contact with the inlet frit assembly such that the portions of mobile phase which have passed through the respective sets of channels in the inlet flow distributor pass respectively through the frit assembly as first and second portions of mobile phase in different radial regions of the column. By arranging the flow distributor in direct contact with the frit assembly it is less likely to introduce voids. The inlet flow distributor in use may sit flush against the frit surface. The flow distributor in use may sit in contact with one or more of the non-porous parts of the frit assembly so that the one or more non-porous parts provide a seal between the frit (e.g. frit sections) and flow distributor thereby sealing adjacent portions of mobile phase flow from each other at the inlet. For example, the non-porous outer frit fitting and/or non-porous flow barrier (which separates the porous frit sections), may seal against the inlet flow distributor to thereby keep the portions of mobile phase separate as they pass through the inlet frit.

The channels through the inlet flow distributor, preferably end fitting, preferably each have an entrance or inlet port at their upstream end, to which can be connected entrance plumbing to carry mobile phase to the column. The number of channels may or may not equal the number of entrance ports, for example in some embodiments any two or more channels in the inlet flow distributor could share an entrance port. Preferably, however, the number of channels is equal to the number of entrance ports.

Preferably, the outer or peripheral channels and their ports in the inlet flow distributor are arranged symmetrically about the central axis of the column. For example, the outer or peripheral channels and their ports may be equally spaced apart and/or equidistant from the central axis/central channel and port. However, the outer or peripheral channels and their ports could be arranged un-symmetrically.

Preferably, the inlet flow distributor comprises one central channel and from 2 to 12 outer channels, i.e. 2, 3, 4, 5, 6, 7, 8, 9, 10, 11, or 12 outer channels, more preferably one central channel and from 3 to 6 outer channels. An inlet flow distributor having 3, 4, 5 or 6 outer channels is a good example. However, these numbers are not limiting on the invention.

The inlet flow distributor preferably has the same number of central channel(s) (especially one central channel) and the same number of outer channels as the outlet flow distributor described herein.

As preferred examples, in a first preferred embodiment, the inlet flow distributor, preferably end fitting, comprises one central channel and three outer channels (i.e. a four channel or port configuration). In a second preferred embodiment, the inlet flow distributor comprises one central channel and six outer channels (i.e. a seven channel or port configuration). The number of channels and the number of ports can be varied, e.g. four port, five port, six port, seven port, eight port, nine port, ten port, eleven port, or twelve port configurations may be used, or indeed configurations with even higher numbers of ports may be used.

With regard to the number of central entrance ports versus the number of peripheral entrance ports, the inlet flow distributor, preferably end fitting, in the above-mentioned first preferred embodiment may have one central entrance port at the centre and three peripheral entrance ports surrounding it but it should be understood that the present invention contemplates any number of peripheral entrance ports, e.g. one or more peripheral entrance ports. Preferred examples may have from 3 to 12, more preferably 3 to 10, peripheral entrance ports, particularly 3, 4, 5, 6, 7 or 8 peripheral entrance ports. An inlet flow distributor, preferably end fitting, with 3, 4, 5 or 6 peripheral exit ports is a good example. Furthermore, the present invention contemplates any number of central entrance ports (i.e. those ports which transmit a flow to a central radial region), e.g. one or more central entrance ports. Preferably, there is one central entrance port. The entrance ports in general may be located in the end or sides of the body of the flow distributor, preferably the end. The outer entrance port or ports may be located in the end or sides of the flow distributor. The central entrance port or ports may be located in the end or sides of the flow distributor but preferably the end.

Selecting the number and the size of the entrance port(s) channeling each portion of the mobile phase may be a means to vary the ratio of the respective volumes of the portions of mobile phase flow (i.e. the degree of inlet segmentation). The ratio of the respective volumes of the portions of mobile phase flow at the inlet (degree of segmentation) may alternatively or also be varied by adjusting the pressures in the inlet channels (i.e. the differential inlet pressure).

In use, one or more of the entrance ports may be closed, i.e. blocked off, so that mobile phase does not flow therethrough but instead is caused to flow through the remaining open ports.

The inlet end fitting may be of similar external dimensions to a conventional end fitting. The inlet end fitting may be either hand tightened or tightened with the aid of a tool if necessary to the end of the column at the column inlet. The end fitting is preferably fitted to the inlet end of the column by a screw connection, or may be push fitted, or may connect using another type of connection. As with many conventional types of end fittings for analytical columns, e.g. for HPLC, a typical connection for the end fitting on the column comprises an external screw thread on the inlet end of the column and an internal screw thread inside the end fitting. In such arrangements, the end fitting thus screws onto the end of the column and covers the inlet. In other embodiments, the end fitting may be fitted internally in the column end, e.g. with certain types of self-packed columns and axial or radial compression columns. In such embodiments, the end fitting may be push (friction) fitted into the column end and optionally may carry a sealing means, such as one or more sealing rings or o-rings, on its outer surface to seal against the internal surface of the column wall. The end fitting may be made of any suitable material. The end fitting may be made of metal, preferably stainless steel, especially where it is fitted to a metal column, e.g. stainless steel column, preferably by a screw thread or by using a SWAGELOK® type fitting. In other cases, e.g. where the column is glass, the end fitting may be made from other suitable materials, e.g. plastics, for instance PEEK.

Herein the term column means any tubular structure for performing chromatography on a sample. Accordingly, the column may be a straight column or a coiled column, preferably a straight column. Preferably, the column is a column that can be packed with a suitable media. It may be, for example, a large scale column used for industrial scale preparative chromatography, or a small scale column for preparative chromatography on small amounts of samples and/or in a laboratory environment. It may be a column for analytical chromatography. Typically the column is a column for liquid chromatography but may, for example, be a column for supercritical fluid (SCF) chromatography. The flow paths for the SCF throughout the apparatus are appropriately pressurised in that case. The column may be, for example, a column for high performance liquid chromatography (HPLC), ultra-high performance liquid chromatography (UHPLC), flash column chromatography, fast protein liquid chromatography (FPLC) and other forms of chromatography. The column may comprise a capillary (as used in capillary chromatography). Advantageously, the column in certain embodiments may be a standard, i.e. conventional, HPLC column, thereby allowing the invention to be employed by users on standard columns wherein only modifications at the column outlet and optionally the column inlet need be made, e.g. use of a modified frit assembly and/or flow distributor as herein described.

Suitable columns, as is known, may be made of a wide variety of materials including, for example, metal (preferably stainless steel), glass, ceramic, polymer etc. The column may be made as a microfabricated or integrated fluidic chip structure (integrated chip columns). The column may be any suitable length; preferably columns are of length in the range 5 mm to 1000 mm (possibly longer), e.g. 50 to 200 mm, e.g. about 100 mm, especially for analytical, e.g. HPLC, applications. The column may be of any suitable diameter; preferably the column internal diameter lies between 300 µm and 1000 mm, e.g. standard internal diameters such as 4.6 mm diameter for HPLC. The column is preferably of circular cross section (i.e. transverse cross-section), although other shape cross section columns may be used.

The chromatography which the invention is useful for, in different embodiments, may be analytical chromatography, e.g. high performance liquid chromatography (HPLC), ultra-high performance liquid chromatography (UHPLC), multi-dimensional or two dimensional high performance liquid chromatography (MDHPLC or 2DHPLC), flash column chromatography, fast protein liquid chromatography (FPLC), parallel detection chromatography, SCF chromatography and other chromatography, especially HPLC.

The chromatography which the invention is useful for, in embodiments, may be preparative chromatography, e.g. preparative-high performance liquid chromatography (PH-PLC), process chromatography, protein purification, enzyme purification, antibody purifications, small molecule purifications, pharmaceutical purifications, or natural product purifications.

The liquid chromatography which the invention is useful for, in embodiments, may be both analytical and preparative chromatography, e.g. where the eluate is both detected for analytical purposes and collected in purified fractions.

With regard to the type of mobile phase and stationary phase to be used, any suitable type of mobile phase and stationary phase, e.g. any suitable and/or known phases, may be used which are appropriate for the type of chromatography being performed, e.g. any known HPLC mobile phase and stationary phase when performing HPLC. With regard to the type of separation method that may be used, any suitable conventional methods may be used, for example, either isocratic or gradient elution, or displacement elution, either normal phase or reverse phase or hydrophilic or ion exchange or ion exclusion or affinity or chiral or size exclusion LC etc.

Where the chromatography is supercritical fluid chromatography, the mobile phase may be a conventional SCF such as carbon dioxide but is not limited thereto.

Apparatus utilizing the present invention and methods of the present invention may be used for a wide variety of applications, including, for example, purity analysis, component analysis, quality analysis, quantitative analysis, and isolation or purification on the analytical scale, the pilot scale or industrial scale. Market applications include, for example, drug discovery, clinical analysis, environmental analysis, and diagnostic marker research in the fields of proteins, glycoprotein, phosphoprotein, metabolites and nucleic acids, for example. The invention is thus applicable, for example, in the pharmaceutical, chemical, biotechnology, biopharmaceutical and manufacturing industries.

The invention is applicable to packed columns. Packed column herein means a column containing any suitable bed for the stationary phase. Any conventional bed media may be packed inside the column as the column bed, depending on the type of chromatography being performed. The bed media may comprise, for example, particles or porous monolithic material (e.g. polymeric or ceramic monolithic bed), preferably particles. The bed media alternatively may comprise a membrane bed or any other bed. The invention is especially useful for beds that are heterogeneously distributed. Particle sizes of the preferred particulate media may range, for example, between 1 μm and 150 μm, but no lower or upper limits on particle size limit the invention. A wide range of pore diameters may be used with porous media utilized in the invention depending on the type of chromatography; preferably pore sizes range between 30 Å and 3000 Å (3 and 300 nm). Porosities of a wide range may be used; preferably porosities lie in the range from 0% to 80%. Packing media may include various chemistries depending on the type of chromatography, for example alkyl bonded phases, typical polar bonded phases and chiral stationary phases. Integrated chip columns may use particles or porous monolithic beds.

The type of detectors which may be used in the processing means may comprise any conventional detector for column chromatography, e.g. ultraviolet or visible (UV/Vis), mass spectrometric (MS), fluorescence (FL), chemiluminescence (CL), refractive index (RI), conductivity (CD), evaporative light scattering (ELSD) detectors etc. Moreover, any non-conventional detector for column chromatography may be used in the processing means, e.g. nuclear magnetic resonance (NMR) or infrared (IR) or antioxidant detectors, or any other bio-type detector. In some cases, in-column detection may be used, wherein a detector is positioned in the column bed so that, for example, the detector detects only the mobile phase from a particular radial region, especially the central region. Such detectors may comprise conductivity detectors.

Preferably, a first portion of the flow of eluate is directed to a first processing means and a second portion of the flow of eluate is directed to a second processing means. The portions are processed separately from each other, i.e. the first and second processing means are separate. In this way, for example, a first portion having a relatively higher resolution of separation can be separately detected from a second portion having a relatively lower resolution of separation. However, even the portion having a relatively lower resolution of separation may exhibit better resolved peaks than a conventional arrangement, which detects eluate gathered from across the whole width of the column via a single central outlet port, or otherwise collectively processes eluate gathered from across the whole width of the column. The invention can thereby provide, e.g., a chromatogram from the first portion and/or a chromatogram from the second portion, each with a higher resolution of peaks than if the portions were detected together. In another example, a first portion having a higher resolution of separation can be separately collected in fractions from a second portion having a lower resolution of separation. This can thereby provide collected fractions from the first portion having a higher purity than if fractions were collected from the portions together.

It will be apparent, therefore, that the invention further provides, in yet another aspect, an apparatus for performing multiplexed chromatography, comprising: a chromatography column, the column having an inlet and an outlet, wherein the outlet is configured to split a flow of eluate as it leaves the column through the outlet into at least two separate portions, wherein the apparatus is configured to separately process the portions. Similarly, the present invention also provides a method of multiplexed chromatography comprising: providing a mobile phase comprising a sample to be separated into components; flowing the mobile phase longitudinally through a chromatography column from an inlet of the column to an outlet of the column, the mobile phase leaving the column through the outlet as an eluate; splitting the flow of eluate as it leaves the column through the outlet into at least two separate portions; and processing the at least two separate portions separately. The separate portions have each undergone chromatographic separation of components in the column. The separate processing may comprise separately detecting the portions, e.g. each portion with a different detector. In this way, different detectors, each with its own unique detecting advantages, can be used to analyze portions of the same eluate in parallel. The advantage of multiplexing may lie in increasing sample throughput. The preferred features of the apparatus and method for performing multiplexed liquid chromatography are described herein in conjunction with the other aspects of the invention.

In the embodiments with segmented inlet, the sample is preferably substantially all contained in the first portion of the mobile phase introduced into the column to thereby provide a sample flow portion and the second portion of the mobile phase introduced into the column is substantially free of sample (i.e. consists only of mobile phase solvent) to thereby provide a curtain flow portion free of sample. In this way, for example, the first or sample flow portion having a sample which has been separated into components along the column can be separately detected from the second or curtain flow portion substantially without sample therein. The first or sample flow portion is preferably the portion which has flowed through the central region of the column, wherein separation efficiency is highest. The curtain flow functions to constrain the transverse migration or diffusion of the sample and/or to flatten the flow velocity profile in a transverse cross section. The curtain flow being substantially without sample therein may be processed as one portion of the eluate leaving the column by re-using it in a further round of chromatography. In this way, a cost-saving on solvent consumption is achieved with accompanying environmental benefits. Accordingly, in such embodiments, the apparatus preferably is configured to re-use the portion of eluate which emanates from a peripheral radial region or curtain flow in further chromatography.

Preferably, the second processing means is a different type of processing means to the first processing means. However, in some embodiments, it will be appreciated the first and second processing means may be the same type of processing means (e.g. they may each comprise the same type of detector), one means processing a first portion and the other means processing the second portion, as long as the portions are processed separately. However, preferably, the second processing means is a different type to the first processing means since the portions typically have different degrees of separation and it will be desirable to process them in different ways. As examples, the first and second processing means (and optionally further processing means where the eluate is separated into third or further portions) may each independently comprise one or more of: a detector, a waste reservoir, a fraction receiver or collector, and a column inlet. Thus, the processing for each portion is preferably (independently) one or more of: detecting, collecting fractions, sending to waste, and sending to a column inlet. Preferably, in some embodiments, the processing of one portion, e.g. the first portion, comprises detecting the portion separately from the other portion(s), e.g. for analytical chromatography. Preferably, in some embodiments, the processing of one portion, e.g. the first portion, comprises collecting fractions from the portion separately from the other portion(s), e.g. for preparative chromatography or for multidimensional HPLC, either in a comprehensive analysis, or in a heart cutting analysis. Preferably, in some embodiments, the processing of one portion, e.g. the second portion, comprises sending the portion to a column inlet separately from the other portion(s). In some embodiments, portions may be sent to multiple separate columns for the purpose of providing different selectivity in separation and analysis. Preferably, in some embodiments, the processing of one portion, e.g. the second portion, comprises sending the portion to waste separately from the other portion(s).

Preferably, a first portion (e.g. typically a portion having a relatively higher resolution of separation) is separately detected from a second portion (e.g. typically a portion having a relatively lower resolution of separation). More preferably, the first portion in such embodiments is a portion emanating from a central radial region of the column.

In some embodiments, it may be desirable to detect both a portion emanating from the central radial region, and also a portion from the outer radial region as both regions may exhibit better resolved peaks than a conventional arrangement with a single central outlet port, i.e. both streams of eluate may be utilised for analytical and/or preparative purposes when segmenting the flow. Without being in any way limiting on the scope of the invention, this is believed to be due to the fact that a portion of eluate taken from a restricted radial region has a smaller axial spread of sample than eluate taken from across the full width of the column.

Preferably, the first processing means comprises a first detector. As an example, the first processing means may comprise a detector, for detecting a sample present in the eluate, and the second processing means may comprise a waste receiver, typically which is reached without passing the detector of the first processing means. As another example, the first processing means may comprise a detector as described before and the second processing means may comprise the inlet of the same or another chromatography column so that the second portion is subjected to at least a further round of chromatography, e.g. involving recycling of the mobile phase. The second processing means may comprise a valve which can be controlled by a control system and which is switchable between a first position that allows flow of the second portion to the inlet of the same or another chromatography column and a second position that allows flow of the second portion elsewhere, e.g. to a detector, a fraction collector, another column or waste. As yet another example, the first processing means may comprise a detector as before (a first detector) and the second processing means may comprise a detector (a second detector), optionally where the second detector may provide a measurement that may be used (e.g. by the control system) to determine whether to flow the second portion to the inlet of the same or another chromatography column so that the second portion is subjected to at least a further round of chromatography. The control system is preferably provided which preferably receives the signals from the one or more detectors comprised in the first and/or second processing means. The control system may, for one or more of the processing means, control the operation of one or more valves, based on a signal from a detector in the processing means, so as to direct a portion of eluate after it has passed the detector to a desired destination, e.g. to waste or a column inlet. Thus, the apparatus may execute a form of data-dependent processing.

Where a processing means comprises the inlet of a chromatography column, the processing means may further comprise a vessel or flow loop in which eluate to be further chromatographed is gathered and preferably re-concentrated before the further chromatography.

In these various ways, for example, the invention provides a column with an outlet configured to selectively direct a portion of the eluate flow to a first processing means, e.g. a detector, while it directs another portion to another processing means different to the first processing means. Preferably, for analytical purposes, the first processing means comprises a detector arranged so that the first portion is detected separately from the second portion. Preferably, for preparative purposes, the first processing means comprises a fraction receiver arranged so that fractions of the first portion are received separately from the second portion (where the first processing means comprises a fraction receiver, it may also comprise a detector).

It will be appreciated that many other processing means, and combinations thereof, could be employed and some of these are discussed in more detail herein below. Herein, the processing means includes the route taken by a portion of eluate after it leaves the column, so that the portions may, for example, in certain embodiments be directed to the same detector but by different routes so that the portions are detected (processed) separately, e.g. not at the same time in that case. In most cases, it is preferred, however, that the separate portions follow completely separate routes after being split at the column outlet.

In some embodiments, the different portions of eluate split at the outlet could be recombined downstream of the outlet. The portions may be recombined after the portions have undergone separate processing. For example, the portions may be recombined after one portion, preferably the central portion, has been detected separately from the other portion(s). The recombined portions, for example, may then be subjected to one or more further chromatographic separations, optionally after re-concentration of the portions.

A plurality of apparatus according to the invention may be linked together, that is one (or more) of the portions of eluate separated at the outlet of the column may be fed into the inlet of a further column, i.e. of a further apparatus according to the invention. Thus, a cascade of columns in accordance with the present invention may be linked together. Alternatively, the further column may be a conventional column or another column which is not a column in accordance with the present invention. In general therefore, the invention may comprise directing the flow of one (or more) of the portions of eluate to a further column for further chromatographic separation. In this way, a portion (or more than one portion) of eluate in which components of a sample have not been adequately separated, i.e. resolved, may be fed into a further column and subjected to chromatography therein in order to further separate the components. The number of columns which may be connected in this cascading way is not particularly limited. For example, two, three, four, or more columns may be connected together in such series. The eluate may be re-concentrated before injection into each further column or columns. The portion of eluate that is directed to further chromatographic separation is preferably the portion that emanates from the outer or peripheral radial region of the column, as components therein are typically less well separated than they are in the portion that emanates from the central region, but the portion of eluate that emanates from the central portion could optionally be directed for further chromatographic separation, as would be the case in multidimensional or two dimensional HPLC.

As a further variation on the foregoing embodiments, the eluate may be recycled, e.g. via conduits, i.e. directed back to the inlet of the same column for one or more further passes through the same column (i.e. one or more rounds of chromatography). In particular, one (or more) of the portions of eluate separated at the outlet of the column may be fed back into the inlet of the column. In this way, a portion (or more than one portion) of eluate in which components of a sample have not been adequately separated, i.e. resolved, may be fed into the column again and subjected to further chromatography therein in order to further separate the components. The eluate is preferably concentrated before re-injection back into the column for the one or more further passes thorough the column. The portion of eluate that is recycled in this way is preferably the portion that emanates from the outer or peripheral radial region of the column, as components therein are typically less well separated than they are in the portion that emanates from the central region. In cases where the eluate portion is substantially free of sample (i.e. is solvent only), e.g. where a solvent-only curtain flow portion has been flowed through the column and is split from the other portion at the outlet, the solvent only portion may be re-used as mobile phase in further chromatography, thereby reducing the overall mobile phase consumption of the apparatus.

The invention may comprise further known components of a chromatography apparatus in various embodiments. For example, the invention may further comprise at least one mobile phase reservoir to supply mobile phase to the inlet of the column. The invention may further comprise at least one pump to pump the mobile phase from the at least one mobile phase reservoir through the column. In some embodiments, for example in which two or more separate portions of mobile phase are introduced through a multiport inlet, two or more pumps may be used (e.g. one for each portion). However, it may be possible to use a single pump even for the cases of multiple mobile phase portions being introduced at the inlet by using flow regulation, such as an arrangement having a single pump but with pressure restrictions in the lines which carry the mobile phase to vary the degree of flow restriction independently in each line. The invention may further comprise at least one sample injector, e.g. an injection valve, to inject a sample into the mobile phase upstream of the column inlet. The invention may further comprise one or more pressure regulators or flow restrictors to balance the flow from the numerous exit ports at desired levels, the one or more pressure regulators preferably being located downstream of the column outlet. The apparatus is preferably under the control of a Control and Data Collection System, which e.g. comprises a computer and control electronics. The Control and Data Collection System preferably is for controlling (in each case where the component is present) the one or more pumps for pumping of mobile phase through the column, the sample injector for sample injection and the one or more pressure regulators to balance the flow through the exit ports. The Control and Data Collection System preferably is for receiving, and optionally processing, data from one or more detectors of the processing means. The Control and Data Collection System may also provide an output of the data, e.g. with or without processing thereof, as required. The Control and Data Collection System may additionally control other components of the apparatus.

DESCRIPTION OF THE DRAWINGS

FIG. 5A shows a perspective view of a preferred embodiment of a frit assembly in accordance with the invention; FIG. 5B shows the underside view of the embodiment looking in direction of arrow A; and FIG. 5C shows a side cross section view of the embodiment taken on line B-B.

FIG. 5D shows a perspective view of another preferred embodiment of a frit assembly in accordance with the invention; and FIG. 5E shows the underside view of the embodiment.

FIGS. 5F and 5G schematically show respective further embodiments of frit assemblies in accordance with the invention.

FIGS. 5H and 5I schematically show embodiments of exit capillary arrangements at the column outlet in accordance with the invention.

DETAILED DESCRIPTION OF THE INVENTION

In order to further understand the invention, but without limiting the scope thereof, various exemplary embodiments and experiments are now described with reference to the accompanying drawings.

Figure 1:
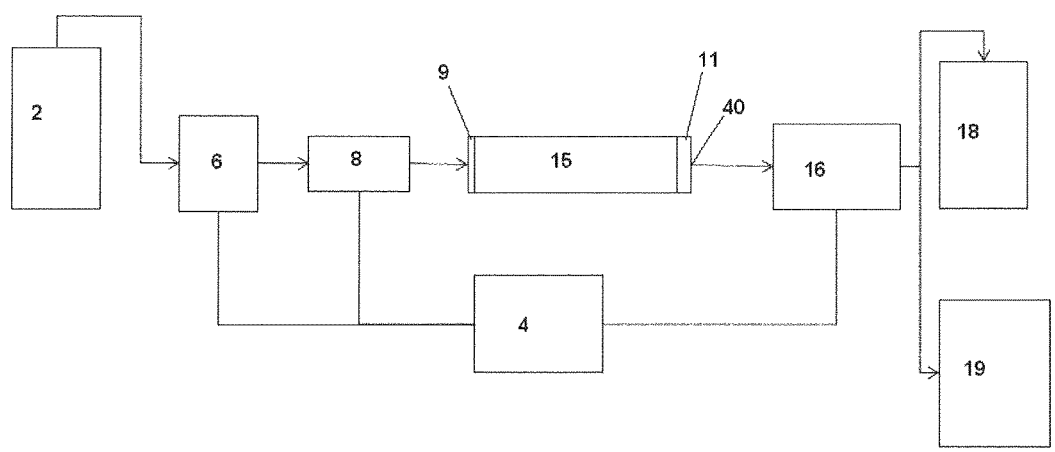
FIG. 1 shows schematically in flow-chart form a conventional configuration of an HPLC system.

In a conventional configuration of an HPLC system (as shown schematically in FIG. 1 in the form of a flow chart), one or more bottles of mobile phase solvent(s) 2 are delivered via tubing to a solvent delivery system 6 that employs a pump pumping at high or low pressures, or are delivered via tubing by force of gravity (low pressure only). The solvent delivery system 6 delivers desired mobile phase solvent or mixtures thereof (herein simply termed solvent) through a sample-injection port or valve 8 where a sample is introduced into the solvent flow and then into a chromatographic column 15 packed with a stationary phase or bed or provided with a monolithic stationary phase. The column is typically a circular cross section cylindrical column. The flow through the column 15 is radially dispersed over the full width of the cross-section of the column bed by a head or inlet frit 9 as well as by the column bed itself and subsequent chromatographic separation then occurs as the sample is carried by the mobile phase solvent down the length of the column. At the exit or outlet of a conventional HPLC column, the out flowing mobile phase or eluate is gathered by a second or outlet frit 11 typically held in place by an end fitting fitted to the outlet end of the column so that the entire cross section of the flow is delivered to a small exit port 40 located at the centre of the cross section of the column. That is, material from outer radial regions of the column near the wall is forced radially inwards to pass, together with material that has passed through the central radial region of the column, through the single central exit port 40. Separated components of sample are then carried by the eluate flow stream through suitable connective tubing into a detector 16, which generates a chromatographic trace. In analytical chromatography, the separated components are either sent to waste 18 after detection, or destroyed during detection. In preparative chromatography, a portion of the eluate flow is detected and that is used as the basis for collecting desired components from the flow stream using a reservoir or fraction collection device 19. The system is under the control of a Control and Data Collection System 4, e.g. a computer and associated control electronics, which in particular controls the solvent delivery system 6 and injector 8 and controls and receives data from the detector 16, as well as controlling other components. The Control and Data Collection System 4 may also process the data for output, e.g. as a chromatogram.

Figure 2:
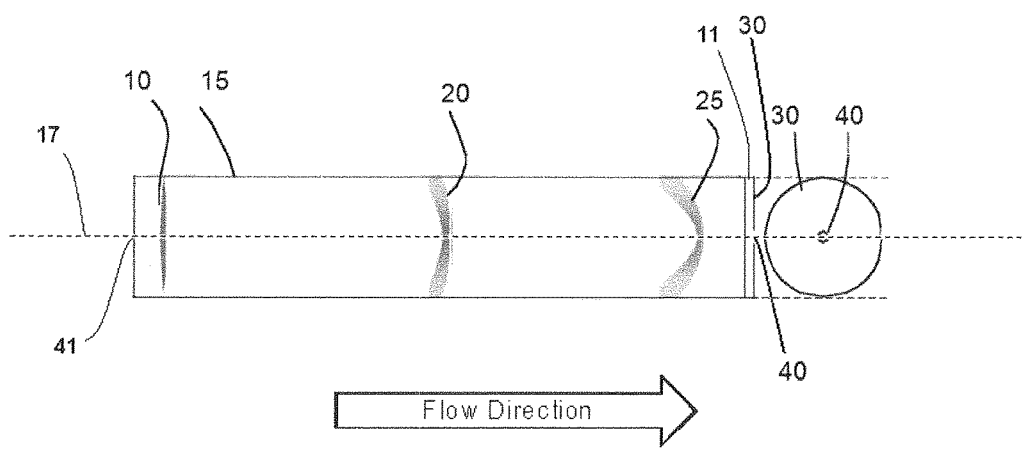
FIG. 2 shows schematically an axial cross-section side view through a conventional packed chromatography column with a single sample component eluting.

As illustrated in FIG. 2, which schematically shows an axial or longitudinal cross-section side view through a conventional packed chromatography column 15, a sample component applied to the head of the column from the injector via a single centre inlet port 41 accumulates there in the shape of a relatively thin, flat band 10. In three dimensions, the band 10 resembles a thin, flat disc that is bounded by the inner diameter of the column casing or wall. During separation on the column, and as the band 10 of sample is carried down the column by the mobile phase, the band begins to change shape as shown by the band at 20 and as described in more detail in the introduction above. Briefly, the centre of the band located on and around the central or longitudinal axis 17 of the column, moves faster than the perimeter of the band nearer the wall, drawing the band of material into a sort of bowl or cup shape as shown clearly by the band at 25. Furthermore, the sample near the column wall begins to spread out (broaden) and become more dilute. This phenomenon is progressive, such that it is most pronounced as the fluid leaves the column at the exit end or outlet of the column. At the end of the column 30, the "bowl" of material, begins to exit the centre exit hole or port 40 located on the central axis 17 after passing through a thin frit layer 11 with minimal impedance of lateral flow. To the right hand side in FIG. 2 is shown the end-on view of the end 30 of the column with the centre port 40 in the middle. The goal of the conventional arrangement is to gather the full cross section of the sample "band" to the centre port 40, and direct it to the detector in as sharp a peak as possible.

Figure 3:
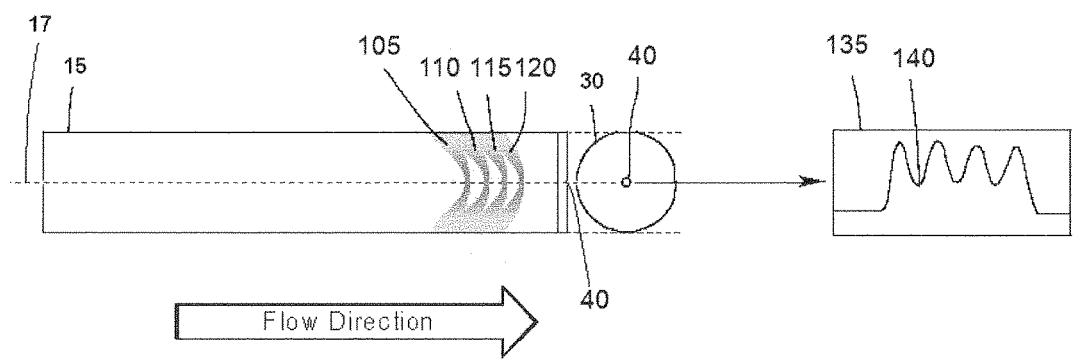
FIG. 3 shows the view of FIG. 2 with four different sample components eluting.

When multiple components are applied to a packed column, their different chemical affinities for mobile and stationary phases in the column cause them to move at different rates through the column than each other. That is the basis of separation in an LC column. FIG. 3, which is analogous to FIG. 2 shows four different sample components 105, 110, 115, 120 that have been partially resolved (i.e. separated) from one another over the length of the column 15. It should be appreciated in the schematic example shown in FIG. 2B that, in the centre of the column, i.e. on the central axis 17, peaks are completely resolved, but the broadening and dilution at the perimeter, nearer the column walls, causes the components to overlap and not be resolved. As this set of components 105, 110, 115, 120 exits the single central hole or port 40 at the centre of the chromatography column outlet, with liquid from across the full width being forced through the port, the peaks in the resulting chromatogram 135 display partial or incomplete resolution. That is, there are distinguishable peaks but they are not completely separated from each other at the early and late part of each peak, e.g. in the inter-peak region 140.

In contrast to the conventional arrangement described, in preferred embodiments of the present invention, the outlet of the column is configured with a plurality of exit ports in contrast to the single exit port 40 of the conventional arrangement. As described in more detail hereinafter, preferred embodiments may use an end or exit fitting (also termed end cap) on the outlet end of the column that has been modified to be unlike a conventional LC end fitting. A preferred modification is that the outlet frit and/or end fitting are designed to drain the mobile phase from the column through multiple channels that are positioned at different points in the transverse (radial) cross section of the column when the frit and/or fitting are positioned at the outlet. In this way, the mobile phase being drained through the multiple channels emanates from different regions of the column, more particularly different radial regions of the column. This allows segregation of the different fluidic components across the diameter of the column. The flow from the multiple channels can be treated as separate portions and processed differently. In preferred embodiments, mobile phase from more advantageous regions of the column such as the central radial region can be processed separately from the less advantageous mobile phase in order to improve the resolution of a resultant chromatogram or the purity of collected fractions for example. By restricting the portions of eluate to limited radial regions of the column, each portion may show improvements in separation efficiency compared to the conventional case where eluate from across the whole column is gathered together and detected as one stream.

Various exemplary embodiments of the invention are now described. There are three main preferred aspects to the embodiments. A first main preferred aspect is that the frit at the outlet is modified to separate and segregate mobile phase arriving from the centre of the column cross section from mobile phase arriving from the region surrounding the centre (i.e. from the perimeter region). Thus, the flow of eluate is split by the frit into a portion which has travelled through the centre of the column and a portion which has travelled through the perimeter region. A second main preferred aspect is that the centre and perimeter flows are then taken off into different exit channels and ports in a flow distributor (e.g. steel end fitting or cap) that is typically fitted (e.g. screwed) to the end of the column. It is possible in some embodiments to use such a distributor without the split-frit which splits the eluate since the flow distributor with multiple ports may alone perform splitting of the eluate flow into the different portions, e.g. where the surface of the flow distributor which faces the frit lies close to the surface of the frit, preferably contacting the surface of the frit. A third main preferred aspect is to use a segmented flow fitting at the column inlet and thereby performing a segmented flow injection to produce curtain flow through the column to further improve efficiency.

Figure 4:
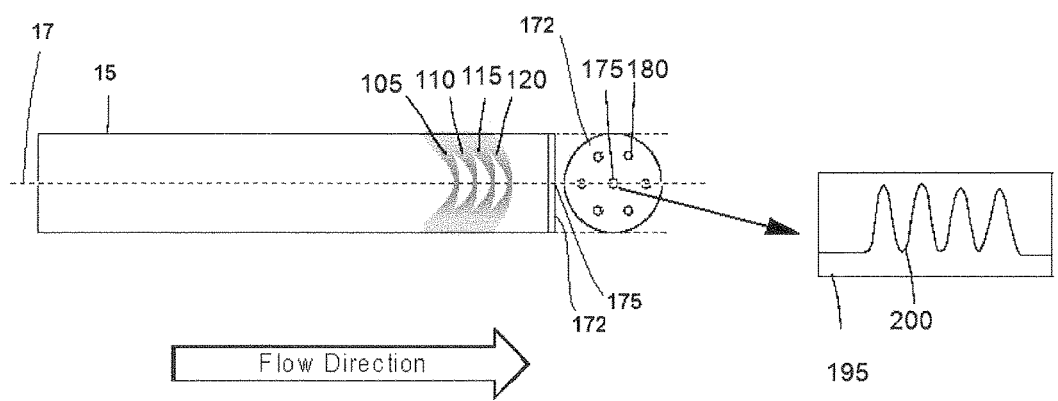
FIG. 4 shows schematically an axial cross-section side view through a packed chromatography column in accordance with the invention showing the principle of a flow distributor at the outlet.

FIG. 4 illustrates schematically the principle of a flow distributor at the outlet of the column 15, which is a packed column, e.g. for HPLC. FIG. 4 shows a schematic longitudinal cross sectional side view of the column similar to FIGS. 2 and 3. To the right hand side of the longitudinal cross section side view is shown an end-on view of the column outlet (i.e. an end-on view of the flow distributor 172 on the end of the column). The flow distributor comprises a centre outlet port 175, positioned similarly to the single centre port 40 of the conventional arrangement, that receives and transmits eluate flowing from the central radial region of the cross section of the column (i.e. a region located on the central axis 17 of the column) which contains the more concentrated and resolved components. The flow distributor further comprises six peripheral ports 180 located equally and symmetrically spaced around the central port 175 that receive and transmit eluate that is flowing in the perimeter region, closer to the inside wall of the column, which contains the more dilute, later-running and typically less well resolved components of the sample.

The eluate leaving the centre of the column represents the most desirable material because it is the most concentrated in components of the sample and has the most sharply resolved components. Thus, the separate use of the central port 175 allows this most desirable portion of the eluate to be selectively directed to a detector and/or fraction collector (not shown). The right hand side of FIG. 4 illustrates the better resolved peaks in a resultant chromatogram (trace 195) which arises from detection of only the eluate from the central port 175. The chromatogram 195 shows an improvement in resolving power compared to the chromatogram 135 obtained using the conventional column arrangement as shown in FIG. 3 where all the eluate from across the full cross section of the column is gathered together and detected. The eluate from the six peripheral ports 180 is gathered together and collectively forms one portion of eluate which is not processed with the eluate from the central port 175. For example, in one embodiment in which eluate from the central port 175 is detected using a detector, the eluate from the peripheral ports 180 may instead be either detected using another, separate detector or separately collected or could be sent to waste or it could be sent to the inlet of the same or another column for a further chromatographic separation in order to better resolve the components, optionally after being re-concentrated before such further chromatographic separation. The peripheral eluate is typically less desirable then the central eluate because it is more dilute and less resolved. It has regions of less homogeneous flow which results in an overall dilution of the solute, since the solute is spread over a larger volume relative to the central flow regime. The invention in preferred embodiments thus separates the central, more concentrated, i.e. more tightly axially contained, solute, which elutes earliest, from the peripheral, less concentrated, i.e. more axially diffuse, solute, which elutes later. Nevertheless, the peripheral eluate may still exhibit better resolved peaks than in a conventional arrangement as shown in FIG. 3. Without being in any way limiting on the scope of the invention, this is believed to be due to the fact that a portion of eluate taken from a restricted radial region has a smaller axial spread of sample than eluate taken from across the full width of the column.

There are different possible ways to design an outlet frit 11 suitable for the purpose of segregating flows of mobile phase from the outlet of the column. FIG. 5A shows a perspective view of one preferred embodiment of a frit assembly 220, with FIG. 5B showing an underside view of the embodiment looking in direction of arrow A and FIG. 5C showing a side cross section view taken on line B-B. In the embodiment shown, the frit assembly is assembled from sections of frit, i.e. a central, circular frit disc 235 and surrounding concentric frit ring 245 both made of porous material conventionally used as frit material, e.g. steel, which are separated from each other by a solid, non-porous flow barrier in the form of concentric ring 240, e.g. made of polymer such as PEEK. The non-porous intervening ring 240 prevents lateral flow of eluate between the two frit sections 235 and 245, thus keeping the central and peripheral eluate flows separate. The width of the non-porous ring 240 is lower than the width of the frit sections in this case, thereby to reduce drag on separated components in the eluate flow. The disc and rings 235, 240, 245 are fixed together and held inside a ring shaped, profiled outer fitting 250 also made of solid, non-porous material, e.g. PEEK, which acts as a fitting to the end of the column as described below. The aforesaid parts 235, 240, 245, 250 are thus assembled so that they fit together to form the assembly 220 which acts as a frit cap, wherein the outer ring 250 is dimensioned and profiled with an extended peripheral edge 224 which fits over the end of the column so that the under-side 222 of the frit cap is push-fitted (i.e. friction fitted) over the end of the column. The over-side of the frit cap 225 in use is in contact with the steel end fitting (described in more detail hereafter) once the end fitting is screwed onto the end of the column. Frit assemblies for use with the invention, like the assembly 220, typically may be push-fitted as shown or screwed onto the column end, but are preferably applied by push or friction fit. FIGS. 5D and 5E show views of a similar frit assembly construction to that shown in FIGS. 5A, B and C except that the frit disc 235' and rings 240' and 245' are of different relative areas thereby splitting the eluate flow into portions from central and peripheral regions of different relative transverse area. As examples, the ratio of the area of the outer frit section 245 (245') to the area of the central frit disc 235 (235') may vary, e.g. from 90%:10% to 50%:50% but typically from 80%:20% to 50%:50% with ratios outside this range also possible. As examples the aforesaid ratio may be about 70%:30% or 75%:25%. Preferably, the said ratio is about 2:1. The ratio of the areas of the frit sections may be a means to vary the ratio of the respective volumes of the split portions of eluate flow. In some embodiments, it may be possible to use a central frit disc 235 (235') that has a different, e.g. lower, density compared to the frit sections 245 (245').

FIGS. 5F and 5G show further frit designs which could be used in the present invention to split the eluate flow at the column outlet, in which a central porous frit disc 535 is surrounded by a plurality of porous frit discs 550, each of the frit discs 535 and 550 being located in a non-porous body 540, which thereby prevents lateral flow of eluate between the two frit sections 535 and 550. Other arrangements similar to those in FIGS. 5F and 5G could have more or less than the six peripheral frit discs 550 shown. The relative areas of the central and peripheral frit discs 535 and 550 may be varied, with examples of different relative areas being shown in FIGS. 5F and 5G.

In certain other embodiments, as shown in FIGS. 5H and 5I, the column outlet 580 may be provided with a plurality of exit capillaries 585, 590 to channel the eluate flow in separate portions out of the end of the column, wherein a radially central capillary 585 is arranged to channel the first portion of the flow from the central region of the column and ten capillaries 590 peripherally arranged around the central capillary 585 are provided to direct the second portion of the flow. Thus, the first and second portions are channeled in separate capillaries and thus are split from each other. Preferably, in such embodiments, frits 592 are provided in the ends of the capillaries as shown in FIG. 5I. The total number of capillaries may be varied, e.g. 5, 6, 7, 8, 9, 10, 11, or 12 or more capillaries.

Figure 6A:
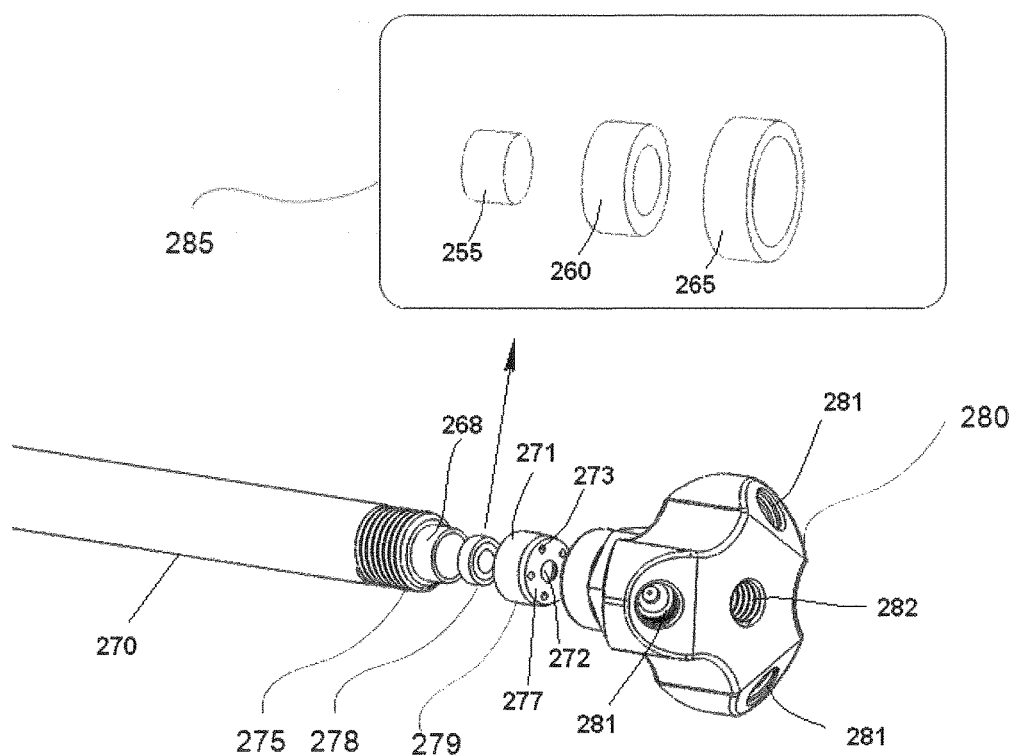
FIG. 6A shows, in exploded view, an embodiment of the invention having a split section frit and four port end fitting.

FIG. 6 shows, in exploded view, an embodiment of the invention, which could be used, for example, with a standard analytical HPLC steel column 270 of 4.6 mm internal diameter. The embodiment in FIG. 6A uses a split frit assembly, 278, 279, and a flow distributor in the form of an end fitting 280 having multiple flow channels therein with corresponding outlet ports 281, 282. The parts (inset 285) of the split section frit 278 (corresponding to parts 235, 240 and 245 in FIGS. 5A-E) are assembled and placed at the column outlet. The frit parts 285 comprise a central frit disc section 255 held in a non-porous intermediate PEEK ring 260, with ring 260 in turn held in an outer peripheral ring frit section 265. Over the frit parts 285, there is a fitting 279, i.e. an outer cap made of PEEK, which acts as a flow adapter and serves to align the respective separated flow paths through the split frit 278 with respective exit ports 281, 282 of a steel end fitting 280 as described later. The fitting 279 comprises a main body 271 which closely fits over the end 268 of the column (by friction fit) and encloses the frit parts 285 of the split section frit 278 at the column end. In an alternative arrangement, instead of friction fit, the fitting 279 could fit to the end of the column by a screw connection (i.e. an internal thread inside the main body 271 of the fitting 279 could screw onto an external thread on the end 268 of the column). The fitting 279 has a radially central aperture 272 which is aligned with the central frit section 255 of the split frit to thereby allow passage through the aperture 272 of eluate emanating from the central radial region of the column which has passed through the central frit section. The fitting 279 also has a plurality of, preferably equally spaced, peripheral apertures 273 (in this case 5 apertures) which are positioned peripherally around the central aperture 272 and lie in an annular recess in the end face 277 of the adapter. It will be appreciated that the apertures 273 could be circular or they could be slits or of some other shape. The peripheral apertures 273 in this case are radially aligned with the peripheral frit section 265 of the split frit. The apertures 273 thereby allow passage through of eluate emanating from the peripheral radial region of the column that has passed through the peripheral frit section 265. The peripheral eluate collected through apertures 273 in this way is communicated into the annular recess in which the apertures 273 lie in the end face 277 of the fitting 279.

The steel end-fitting or end-cap 280 is screwed, either hand tightened or tightened with the aid of a tool if necessary, onto the external screw thread 275 on the outside of the column end. The end-fitting 280 provides one or more exit ports, in this case three exit ports, 281, for mobile phase exiting the column from the peripheral radial regions of the column (i.e. via peripheral frit section 265 and peripheral apertures 273) and a central exit port 282 for mobile phase exiting the column from the central radial region of the column (i.e. via central frit section 255 and aperture 272).

When assembled, the underside of the tightened end fitting 280 (not visible in the figure) contacts the end face of fitting 279. The annular peripheral recess described in the end of fitting 279 containing apertures 273 is aligned with and in fluid communication with the peripheral ports 281 so that the peripheral flow of eluate through the peripheral apertures 273 is thereby communicated through the peripheral ports 281 in the end fitting 280. The annular nature of the recess means that rotational alignment of the peripheral ports 281 with the peripheral apertures 273 is not required. Eluate received from peripheral ports 281 emanates from the same peripheral radial region and thus is preferably gathered and processed together as one portion of eluate, e.g. detected, or directed to waste or sent to the inlet of a chromatography column for further chromatographic separation. Most typically, the flow from the peripheral ports 281 will be combined together and processed as one portion. However, it will be appreciated that flow from one or more peripheral ports could be processed separately. Indeed, the flow from each peripheral port could be processed separately.

The central aperture 272 in the fitting 279 on the other hand is in fluid communication with the central port 282 of the end fitting. The eluate from central port 282 of the end fitting thus emanates from the central radial region of the column and is processed differently to the eluate from the peripheral ports. The eluate from central port 282 comprises the portion of mobile phase in which the components of the sample have been better resolved and may thus be detected with increased resolution in the case of analytical chromatography or collected in purer fractions in the case of preparative chromatography. The exit ports 281, 282 have internally threaded surfaces (female threads) to accept a screw fitting for exit plumbing as described below. Alternatively, it is possible to arrange the exit ports to have a male thread, e.g. male thread on a protruding portion, onto which is screwed a fitting for exit plumbing.

Figure 6B:
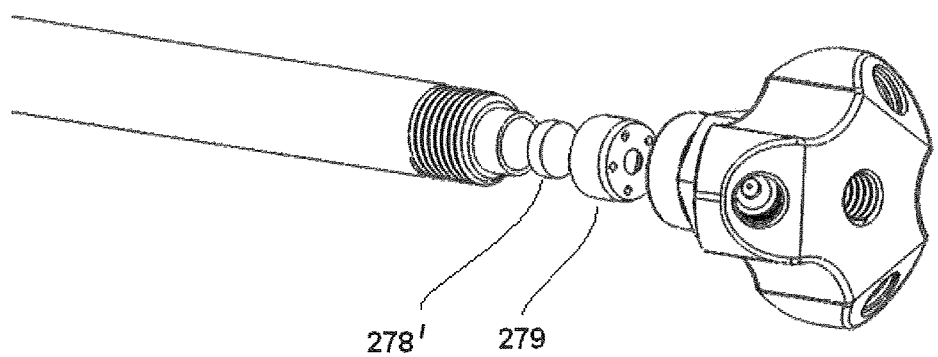
FIG. 6B shows a similar embodiment to FIG. 6A but having a single piece frit.

The embodiment in FIG. 6B is largely the same as shown in FIG. 6A but instead of the split section frit 278 it uses a frit assembly that has a single frit piece 278' inside the fitting 279, wherein the fitting 279 divides the flow at the downstream side of the frit piece by means of its apertures 272 and 273.

Figure 7:
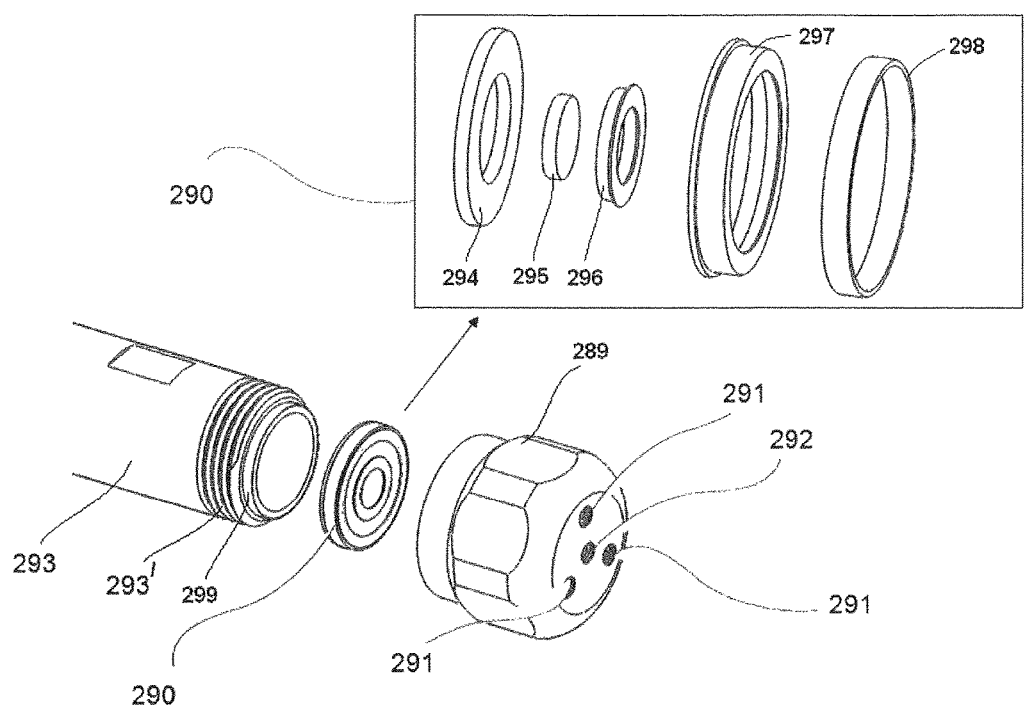
FIG. 7 shows, in exploded view, a further embodiment of the invention having a split section frit and four port end fitting.

FIG. 7 illustrates an exploded view of an example of a column 293, having at its outlet an externally threaded end portion 293', on which is screwed end fitting 289, which has an internal threaded surface for this connection. A split frit assembly 290, having frit parts as shown (see exploded view inset), is push-fitted over a portion 299 of the column end having a smaller external diameter than the threaded portion 293'. The split frit assembly 290 is held in placed once the end fitting 289 is screwed on the end of the column. The split frit assembly 290 in this embodiment comprises a central frit disc 295 and peripheral frit ring 294 which are separated from each other by non-porous PEEK ring 296 as a flow barrier. The split frit sections are held in outer PEEK ring fitting 297 which functions as a push fitting cap to fit over the end 299 of the column. The fitting 297 is further secured to the column end with annular steel band 298 which grips the circumference of the PEEK fitting 297. In the FIG. 7 embodiment, the fitting 297 is different to the fitting 279 acting as flow adapter in FIG. 6. In this example, the underside of end fitting 289 seals against the non-porous parts (i.e. parts 296, 297) of the frit assembly 290 to thereby keep fluidly separate the portions of eluate flowing from the frit sections 295 and 294. The end fitting 289 has one central exit port 292 at its centre and three peripheral exit ports 291 surrounding it, although it should be understood that the present invention contemplates any number of peripheral exit ports 291, e.g. one or more peripheral exit ports 291. Preferred examples may have from 3 to 10 peripheral exit ports, particularly 3, 4, 5, 6, 7 or 8 peripheral exit ports. End fittings with 3 and 6 peripheral exit ports are good examples. Furthermore, the present invention contemplates any number of central exit ports (i.e. those ports that transmit a flow of eluate from a central radial region), e.g. one or more central exit ports. Preferably, however, there is one central exit port as in the embodiment shown. The end fitting central exit port 292 lies radially in the central region of the column and is radially aligned with the central frit section 295 and thereby transmits the portion of eluate flow through the central frit section. The three peripheral exit ports 291 lie radially in the peripheral region of the column and are radially aligned with the peripheral frit ring 294 and thereby transmit the portion of eluate flowing through the peripheral frit ring. The exit ports 291, 292 have internally threaded surfaces to accept a screw fitting for exit plumbing as described below.

Figure 8A:
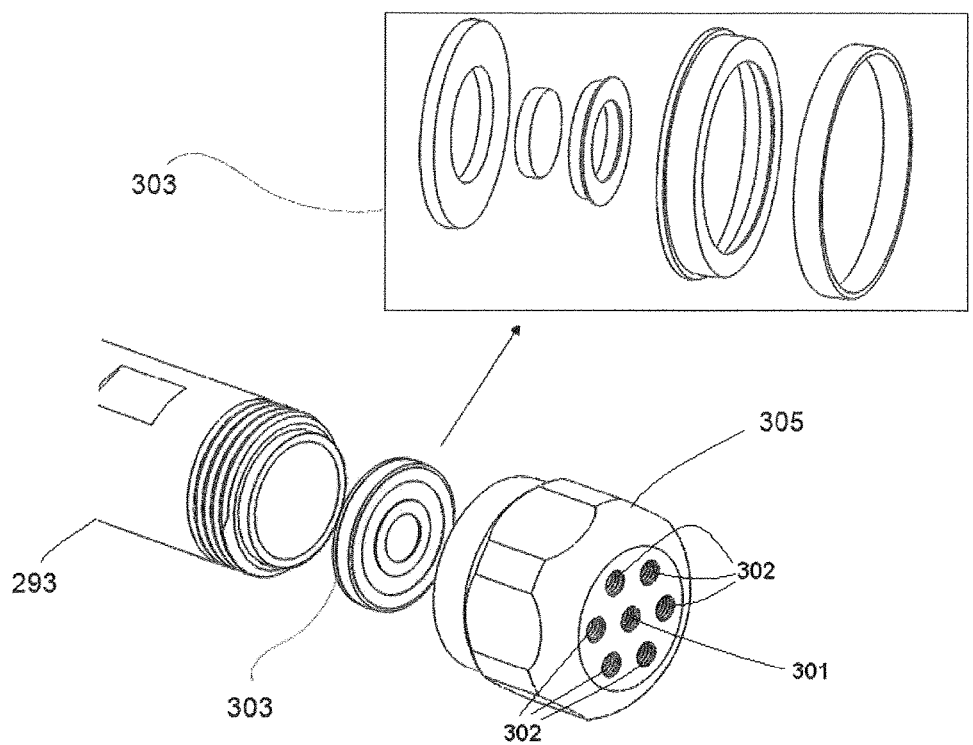
FIG. 8A shows, in exploded view, a still further embodiment of the invention having a split section frit and seven port end fitting.
Figure 8B:
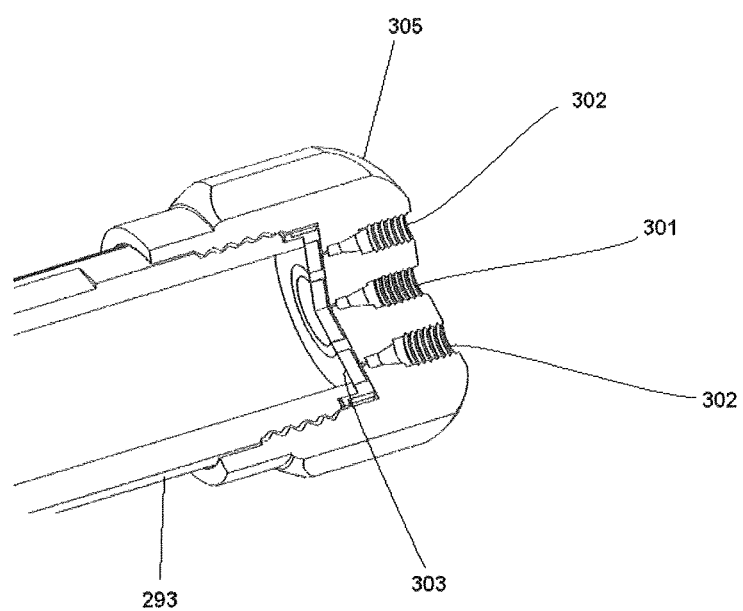
FIG. 8B shows the assembled embodiment of FIG. 8A in a cut-away view.

FIG. 8A illustrates an exploded view of an alternative frit assembly 303 and end-fitting 305 generally similar to that shown in FIG. 7. In this example though, the end-fitting 305 has six peripheral outlet ports 302 around one central outlet port 301. The assembled frit assembly 303 and end-fitting 305 are shown in FIG. 8B, which has been cut away to show the relationship of the assembled parts inside.

Figure 9:
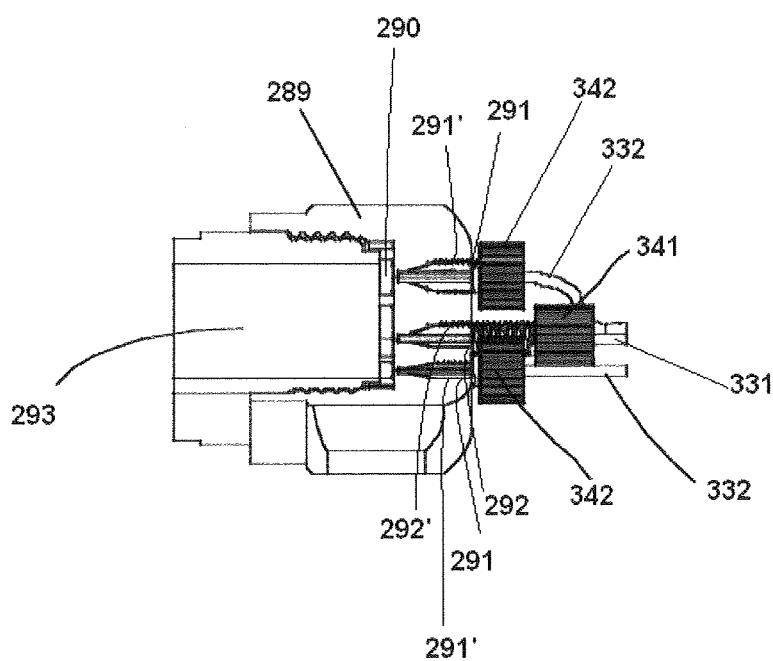
FIG. 9 shows a cut-away side view of the embodiment shown in FIG. 7, shown in assembled form and with exit plumbing attached.

FIG. 9 illustrates a cut-away side view of the same four-port end fitting shown in FIG. 7, but shown assembled on the column 293 together with exit plumbing attached. It can be seen more clearly from this view that the exit ports 291 and 292 are at the exit of respective channels 291' and 292' running through the end fitting 289 from its inner surface which is in fluid communication with the frit assembly 290 to its outer surface where the exit ports 291, 292 lie.

An exit plumbing tube 331, of standard type for HPLC, is fitted to the centre exit port 292 by means of male screw fitting 341. Exit plumbing tubes 332, again of standard type, are fitted to the peripheral exit ports 291 by screw fittings 342 of the same type as screw fitting 341. The screw fittings 341 and 342 are screwed into the channels 292' and 291' for the ports 292 and 291 respectively, which channels carry an internal (female) screw thread for this purpose, and the plumbing tubes 331, 332 are thereby compression fitted. It will be appreciated that in other designs the exit plumbing could be fitted to the exit ports by means of a female screw fitting which fits to a male exit port on the end fitting. The end fitting 289 is tightly screw fitted on the end of the column 310 so that inner surface or underside of the end fitting 289 contacts the end face of the frit assembly 290 and thereby the respective central and peripheral portions of eluate passing through the frit are passed into the respective central and peripheral channels 292' and 291' of the end fitting. The underside of end fitting 289 seals against the non-porous parts (i.e. parts 296, 297) of the frit assembly 290 to thereby keep fluidly separate the portions of eluate flowing from the frit sections 295 and 294.

It will be appreciated that many further embodiments of the present invention may be devised to provide a segmented flow at the column outlet.

It can be seen from the foregoing description that the present invention has the great advantage that it can be practiced using existing conventional packed chromatography columns by segmenting the eluate flow, e.g. by providing an end fitting having multiple ports, so that eluate from different regions of the column is processed differently. Advantageously, the segmentation of the eluate flow is performed on-column, i.e. not post-column. The present invention may therefore, for example, be practiced using a conventional HPLC system wherein one portion of the eluate flow is directed to the detector and the other portion is sent to waste or recycled or processed in another way.

Figure 10:
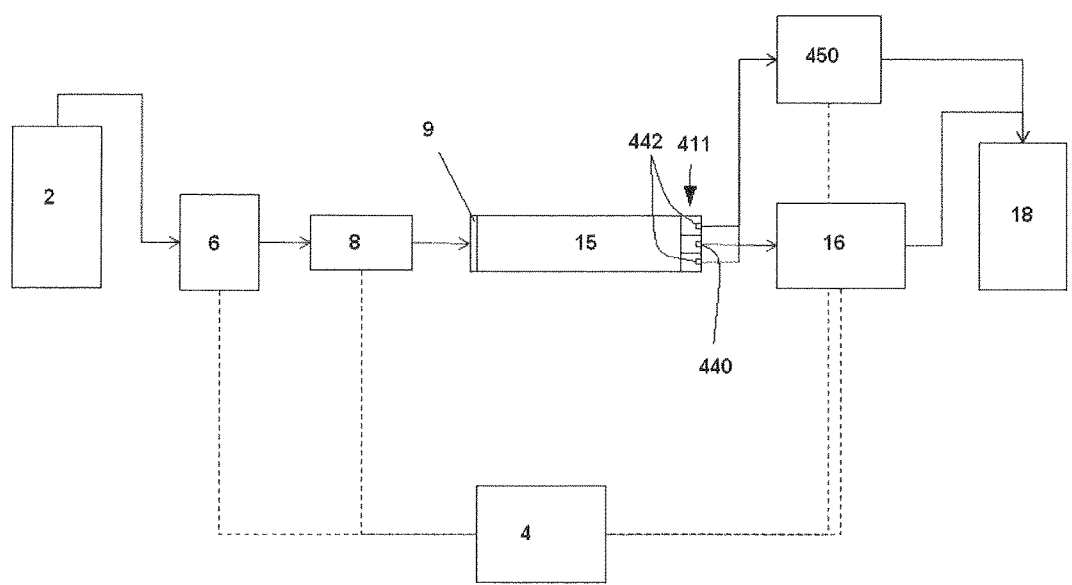
FIG. 10 shows schematically in the form of a flow chart an embodiment of an analytical LC system according to the invention.

In FIG. 10 is shown schematically in the form of a flow chart one embodiment of an analytical LC system according to the invention. The system is largely similar to the conventional system shown in FIG. 1 and like reference numerals are therefore used to denote like components. The main difference is at the outlet of the column where a split frit assembly and multi-port end fitting, collectively indicated by reference 411, is fitted so that the out flowing eluate is split into at least two portions as described above. A small central exit port 440 located at the centre of the cross section of the column flows eluate emanating from the central region of the column to the detector 16. Separated components of sample having an improved degree of separation are thereby carried by the central eluate flow stream into a detector 16, which generates an improved chromatographic trace. In analytical chromatography, the separated components are sent to waste receiver 18 after detection, or may be destroyed during detection. A plurality of small peripheral exit ports 442 in the end fitting 411 flow eluate emanating from the peripheral region of the column to waste receiver 18. However, in other embodiments, the eluate emanating from the peripheral region via peripheral exit ports 442 may itself be used for analytical purposes and thus may also be detected, e.g. by a separate detector. The peripheral eluate also has greater analytical value by virtue of having higher peak resolution than eluate gathered from across the whole width of the column. It will be appreciated that a similar improved resolution system to that shown in FIG. 10 may be used for preparative chromatography, wherein the sample from central port 440 is collected in fractions, preferably after detecting at least a portion of it, similarly to the collection system of FIG. 1. It is preferable in the improved system shown in FIG. 10 to connect a means to control and or balance mobile phase pressures between the centre exit port 440 and the peripheral exit ports 442 in order to keep the greatest amount of concentrated material traveling down the centre region of the column. For this purpose a flow or pressure regulator 450 therefore may be connected on the exit line(s) from the peripheral ports 442 and/or central port 440, preferably on the exit line from the peripheral ports 442 as shown. The Control and Data Collection System 4, which in particular controls the solvent delivery system 6 and injection port or valve 8 and controls and receives data from the detector 16, also controls the flow or pressure regulator 450, e.g. in response to signal feedback from the detector and/or flow sensors. By actively managing the resistance in the flow lines it is possible to drive more or less fluid through the central or peripheral channels.

Figure 11A:
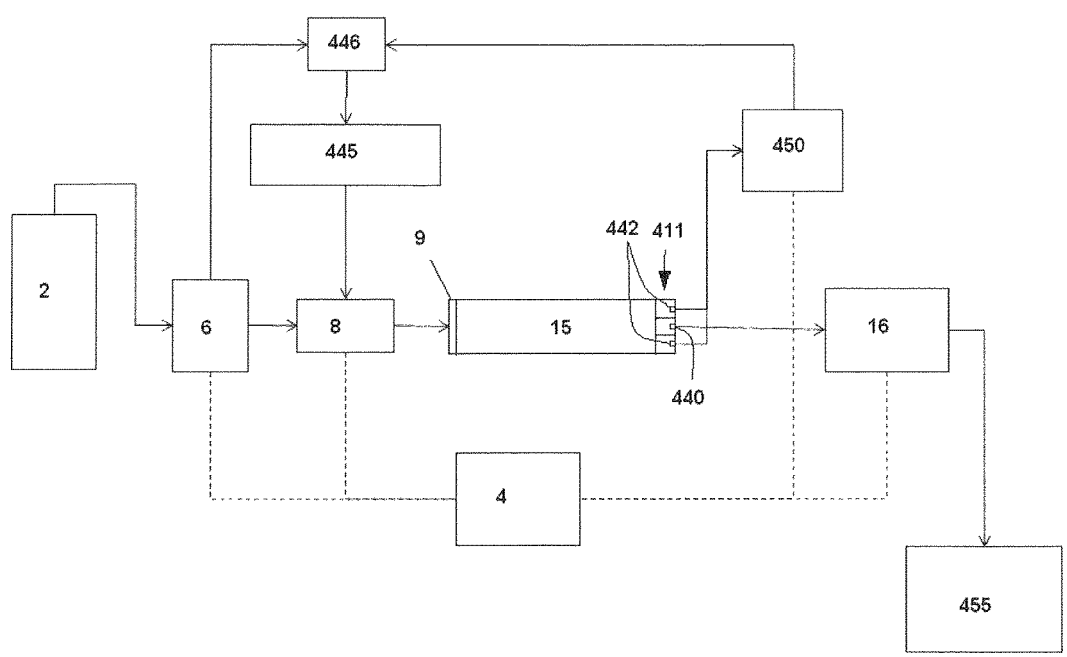
FIG. 11A shows schematically in the form of a flow chart a further embodiment of an LC system according to the invention employing recycling of a portion of the eluate.

The present invention may also enable alternative LC systems in preparative applications. In one embodiment as shown in schematic FIG. 11A, eluate gathered from the central exit port 440 is sent through a detector 16 to a fraction collection device 455. Eluate gathered from the peripheral exit ports 442, however, is not sent through a detector or to a fraction collection device 455, but via valve 446 is saved in one or more reservoirs 445 (which may be any suitable reservoir, for example a trap or additional column), which is or are in communication with the sample-injection valve 8 for the primary column 15 for re-cycling. Once the chromatographic cycle is complete for the primary column 15, the column may then be loaded again, this time with the peripherally eluted material from the previous run(s) collected in the reservoir 445, which is injected into the solvent stream through sample-injection valve 8. The central eluting eluate is once again detected and collected in the fraction collection device 455. Further cycles of chromatographic processing may be used until a sufficiently high and desired proportion of the total material in the original sample is purified and fractionated under the highest-level of chromatography available, by means of taking and collecting the material from the centre exit port 440 separately each time.

Figure 11B:
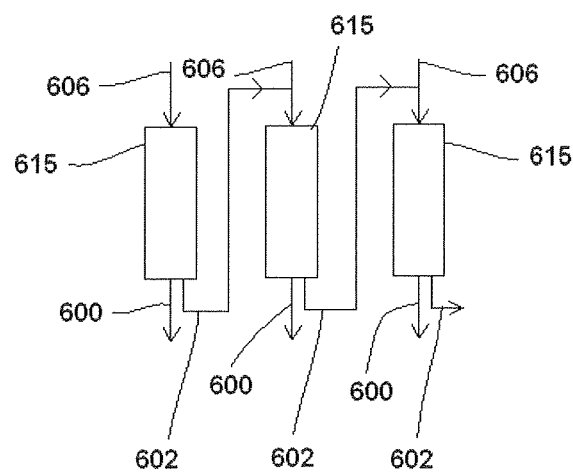
FIG. 11B shows schematically a system for cascading mobile phase from one apparatus according to the invention to another apparatus according to the invention.

FIG. 11B shows schematically a system for cascading mobile phase, in the direction shown by the arrows, from one apparatus according to the invention to another apparatus according to the invention and so on. In the embodiment shown, three LC columns 615, each with their own fresh supply of mobile phase 606 at their inlet, are connected in series. It will be appreciated that the number of LC columns may be more or less than three in other embodiments. Each column 615 has a flow distributor at its outlet to split the flow of eluate leaving the column into two portions: a central flow portion 600 and a peripheral flow portion 602. In the embodiment shown, the central flow portion 600 is detected and/or collected in fractions at the outlet of each column. The peripheral flow portion 602 on the other hand is fed to the inlet of the next column downstream, except that the final column can either send its peripheral flow portion 602 to waste, or recycle it back to the first column in the series, or send it elsewhere.

Examples (1)

Details of various experiments and results are given below to further illustrate the invention by way of additional examples.

Both HPLC and FPLC experimental columns were studied.

For the HPLC separations, a standard stainless steel chromatography column (100×20 mm) was used as supplied by Thermo Scientific. In this case, a reverse phase pentafluorophenyl phase was employed. However, it will be appreciated that in other cases, any type of stationary phase could be employed (e.g. such as C18 or HILIC phases or silica without a bonded phase). A custom-made segmented flow multi-port end fitting for the column outlet as shown in FIG. 9 was made for the work by Thermo Scientific. The segmented flow end fitting thus had 4 ports (one central port and three outer ports). The end fitting was screwed tight onto the column end in place of a conventional fitting. For the comparative runs, a conventional end fitting with a single, central port was used in place of the multi-port end fitting. An annular PEEK encased outlet frit was employed.

For the fast protein liquid chromatography (FPLC) separations, a glass column (OMNI) of 70 mm length×17 mm diameter was employed. The stationary phase in this column was C18 silica. A segmented flow multi-port end fitting with five exit ports (one central port and four outer ports) was used at the column outlet. The end fitting in this case was internally fitted in the column as it was an axial compression column. For the comparative runs, a conventional end fitting with a single, central port was used in place of the multi-port end fitting. For this column, an annular PEEK encased outlet frit was employed.

All mobile phases were prepared from HPLC-grade solvents purchased from MERCK® (Kilsyth, Victoria, Australia). Toluene, ethylbenzene, propylbenzene and butylbenzene used as test solutes were purchased from Sigma Aldrich (Castle Hill, New South Wales). MILLI-Q® water (18.2 MΩ) was prepared in-house and filtered through a 0.2 μm filter.

For the HPLC column, a standard solution of toluene, propylbenzene and butylbenzene was prepared in mobile phase at concentrations of approximately 4 mmol. The standard solution used for the FPLC column contained approximately 2 mmol of toluene, ethylbenzene, propylbenzene and butylbenzene in mobile phase.

All chromatographic experiments using the stainless steel HPLC column were conducted using a Waters 600E Multi Solvent Delivery LC System equipped with Waters 717 plus auto injector, a Waters 600E pump, two Waters 2487 series UV/VIS detectors and two Waters 600E system controllers. Separations were performed under isocratic conditions using a mobile phase of either 80/20 or 70/30 methanol/water, at flow rates of 18 mL/min. The injection volumes were 200 μL. The outlet flow segmentation was varied by adjusting the differential outlet pressure by employing various lengths of PEEK tubing. UV-absorbance detection (254 nm) was undertaken on both segmented flow streams, i.e., on the portion of flow exiting the column from the central region of the packed bed and on the separate portion of flow exiting the column from the wall region of the bed.

Chromatographic separations on the glass FPLC column were made using a SHIMADZU® LC-10APvp system, which included a SHIMADZU® LC-10APvp pump, SHIMADZU®SIL-10ADvp auto injector, SHIMADZU®SPD-10Avp UV detector and a Phenomenex Degassex model DG-440 inline degassing unit. Separations were performed using a mobile phase of 80/20 methanol/water at a flow rate of 2 mL/min using isocratic conditions. The injection volume was 250 μL. Flow segmentation was achieved using the purpose-built segmented flow outlet end fitting, however, in this case, only the eluate from the central region of the column was monitored by UV detection at 254 nm.

An illustration of the parabolic nature of the plug flow through a chromatographic bed is shown in FIG. 2 and has been described above. In the experiments described here, the outlet end fitting was designed so as to separate the region of flow near the column wall from that of the flow in the central section of the packed bed. The design of this head fitting for the HPLC experiments is illustrated in FIGS. 7 and 9. In this end fitting, the eluate flow from the wall region is passed to waste, via a UV detector, while the central region is analysed alone in a conventional manner using a separate UV detector.

Figure 12:
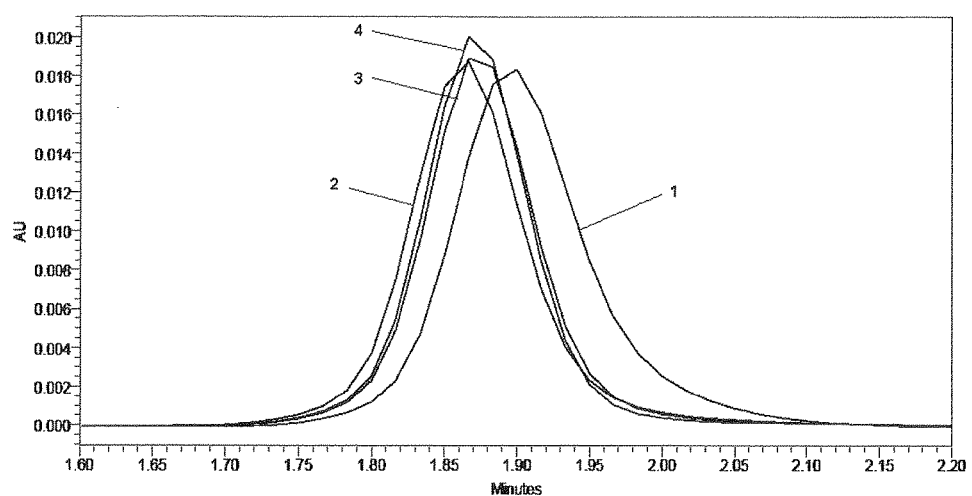
FIG. 12 shows a comparison of a single butylbenzene eluting peak arriving in an HPLC system under different conditions of eluate segmentation.

FIG. 12 shows a comparison of a single butylbenzene eluting peak arriving in the HPLC system (standard steel column (100 mm length×20 mm diameter)) under different eluate segmentation ratios. The difference in chromatographic performance between sample exiting the centre of the column to that of sample exiting the peripheral region of the column was thus compared. FIG. 12 illustrates the peak shape of butyl benzene eluting at various flow segmentation ratios: peak 1 (no segmentation, 100% detected via a central exit), peak 2 (central 53% detected, peripheral 47% to waste), peak 3 (central 42% detected, peripheral 58% to waste) and peak 4 (central 27% detected, peripheral 73% to waste). The elution profiles were recorded for the sample that exited the column via the central exit port. An increase in efficiency (N values) compared to the non-segmented case was as high as 43% when a flow portion of over 70% was sent to the peripheral exits. The plate counts (N) were: peak 1 (2047); peak 2 (2487); peak 3 (2799); and peak 4 (2905). Peak widths were: peak 1 (43 secs); peak 2 (41 secs); peak 3 (37 secs); and peak 4 (35 secs).

Figure 13:
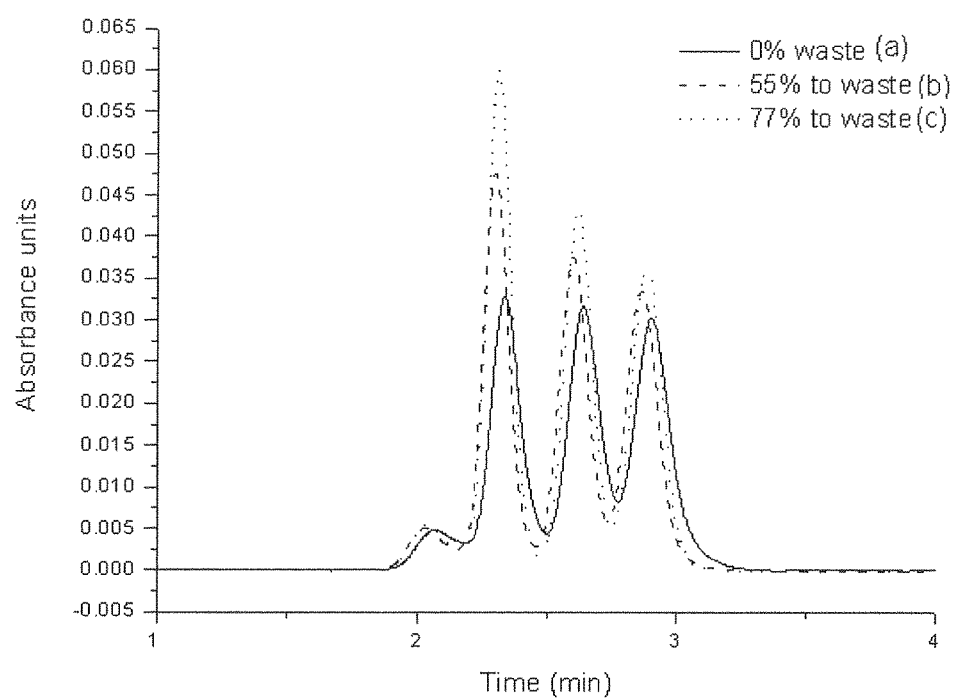
FIG. 13 shows the elution profiles of three test solutes, toluene, propylbenzene and butylbenzene, in an HPLC system under different conditions of eluate segmentation.

Further information about the improvement in efficiency can be seen from the elution profile of all three test solutes. FIG. 13—curve a (solid line) shows the elution profiles of the three test solutes from the HPLC column in an 80/20 methanol/water mobile phase when a conventional end fitting (single exit port) was employed for the separation (i.e. no segmented flow was utilised). In comparison, the chromatogram illustrated in FIG. 13—curve b (dashed line) shows the elution profiles of the same sample, but achieved following flow segmentation with the multi-port end fitting with 55% (volume %) of the eluate flow, i.e. the flow from the surrounding ports, being diverted to waste and the remaining 45% of the flow, i.e. the flow from the central port, being detected and used to produce the chromatogram. Likewise, in FIG. 13—curve c (dotted line) the same separation is shown again, but this time with 77% of the sample, i.e. the flow from the surrounding ports, being diverted to waste and only the remaining 23%, i.e. from the central port, being detected for the chromatogram.

Figure 14:
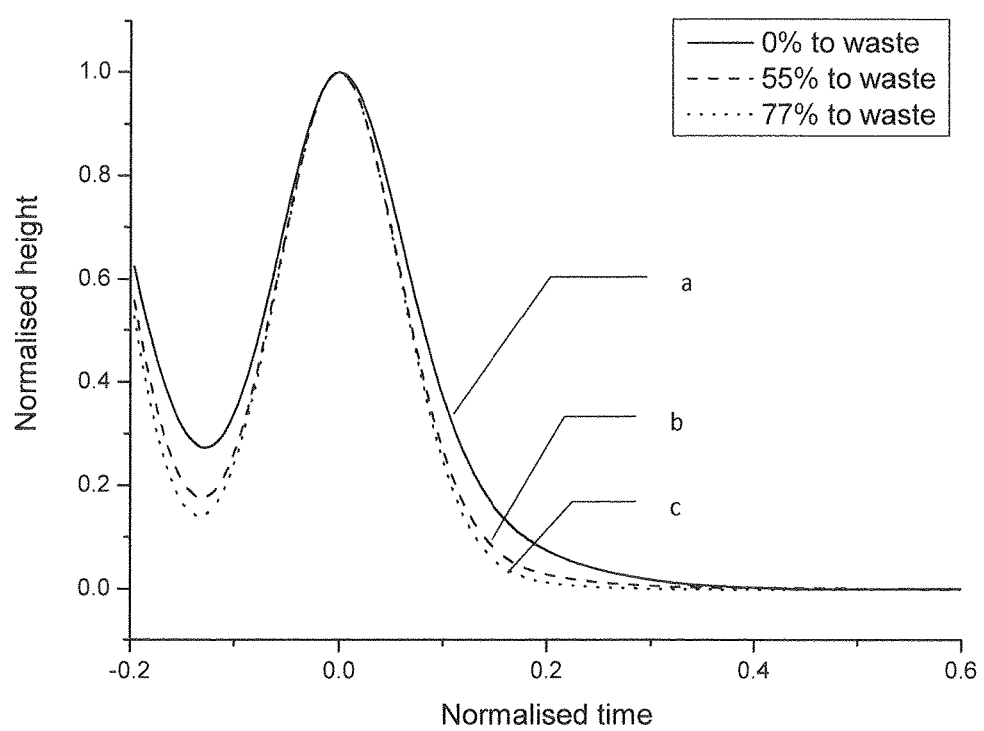
FIG. 14 shows overlaid and height normalised butylbenzene peaks from FIG. 13.

The improvement in separation quality and detection efficiency using the segmented flow arrangement is immediately evident from FIG. 13 in the form of less overlap between neighbouring peaks, narrower peak widths, lower peak tailing and more intense (greater height) peaks. This is further illustrated by examining more closely the normalised peak shapes of the butylbenzene peak and the overlapping regions. FIG. 14 shows overlaid and height normalised butylbenzene peaks from the chromatograms obtained from the separation of the toluene, propylbenzene and butylbenzene standard using the detected flow from the central port of the multi-port end fitting at the various ratios of segmented flow as shown in FIG. 13 curves a-c. The lower degree of peak overlap with the neighbouring peak, lower degree of tailing on the end of the peak and the decreased peak width are clearly shown. These factors greatly improve the resolving power of the separation. For ease of visual inspection, the elution times shown in FIG. 14 are normalised to their peak maxima in order to compensate for the reduction in flow velocity through the detector as a consequence of the difference in flow velocity through the additional post-column dead volume as the proportion of flow to waste increased. The peak heights were also normalised to compensate for the differential residence time in the detector flow cell, and the amount of sample lost to waste. Quite clearly, as the degree of flow segmentation increased (i.e. as proportion being sent to waste increased), separation efficiency in elution increased. However, no account has been taken to consider the apparent visual nature of the band broadening post-column for a sample eluting in the slower fluid flow stream. Had this also been factored into the analysis the improvements in peak shape following segmentation of the flow would have been even more substantial.

A further advantage of the segmented flow arrangement is that sensitivity is observed to be increased (as shown by increased peak intensity in the un-normalised FIG. 13) even as the amount of substance directed to waste is increased. This is believed to be a result of two factors, namely, an increased solute concentration in a less dilute region of the solute plug, and the decrease in flow rate following the flow segmentation; hence the solute residence time in the detection flow cell is increased. This is an additional advantage for detectors which are flow sensitive, e.g. such as UV detectors.

Quite clearly from FIGS. 13 and 14, the sample band profile that resulted from the central port elution in the segmented flow (curves b and c) was more efficient for separation than that of the bulk flow through the non-segmented head fitting (curve a). The resulting plate measurements for each of the three analytes in the HPLC system are given in Table 1, together with peak asymmetry values. The data in Table 1 was derived at a mobile phase composition of 70/30 methanol/water because under these conditions baseline resolution between all three components was achieved. This allowed an accurate measurement of the number of theoretical plates, N, to be made using the method of second variance. Under the segmented flow conditions used here the gain in efficiency (increase in N) was as high as 57%. The peak asymmetry was also greatly reduced under the segmented flow conditions.

Figure 15:
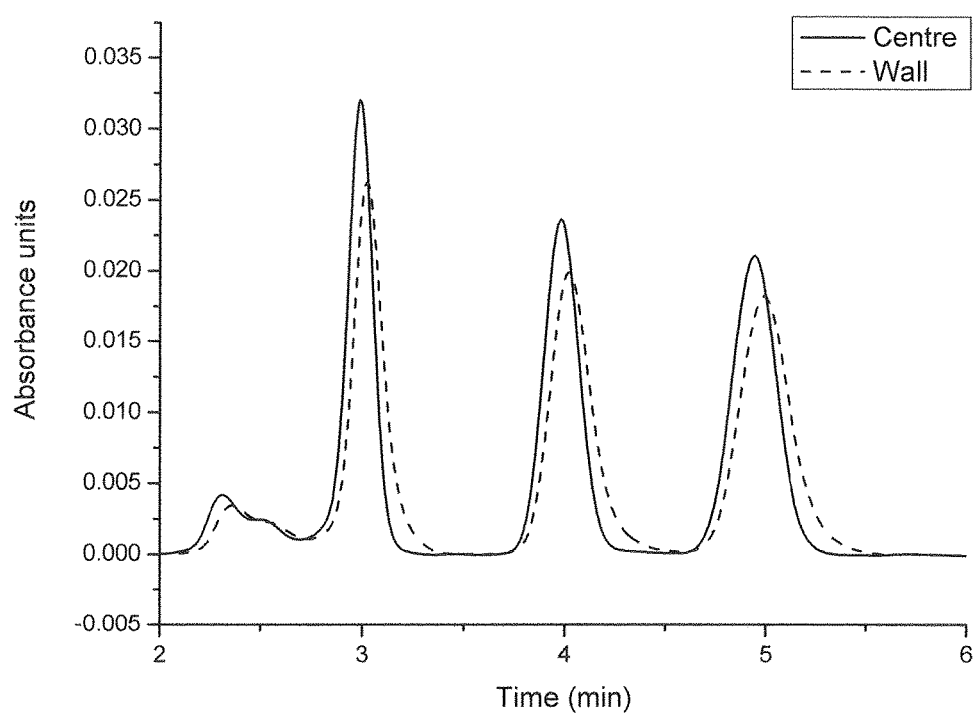
FIG. 15 shows the elution profiles in an HPLC system of the sample of toluene, propylbenzene and butylbenzene eluting from the central region of the column (solid trace), and the wall region (dotted trace).
Figure 16A:
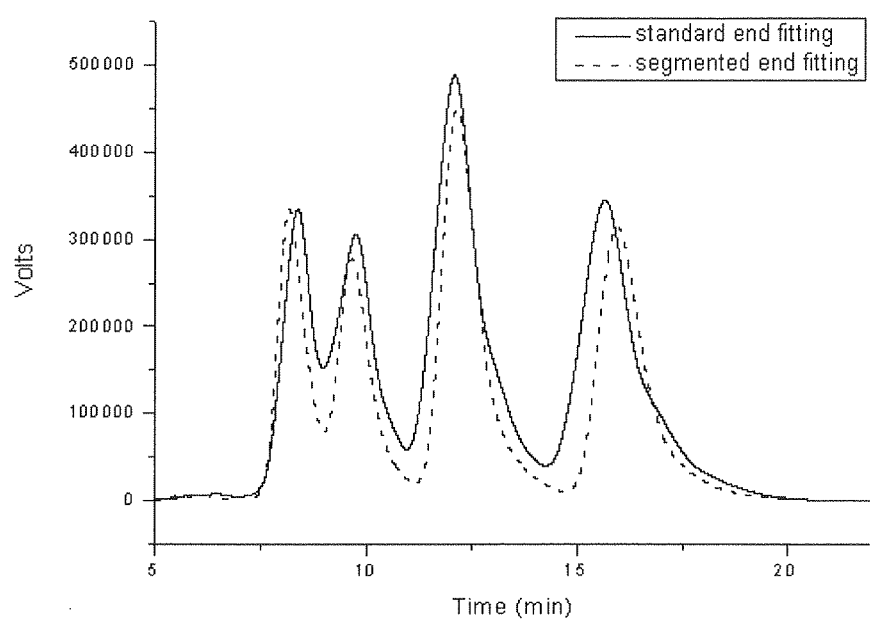
FIG. 16A shows the elution profiles in an FPLC system using a glass column of a sample of toluene, ethylbenzene, propylbenzene and butylbenzene with and without segmentation of the eluate.
Figure 16B:
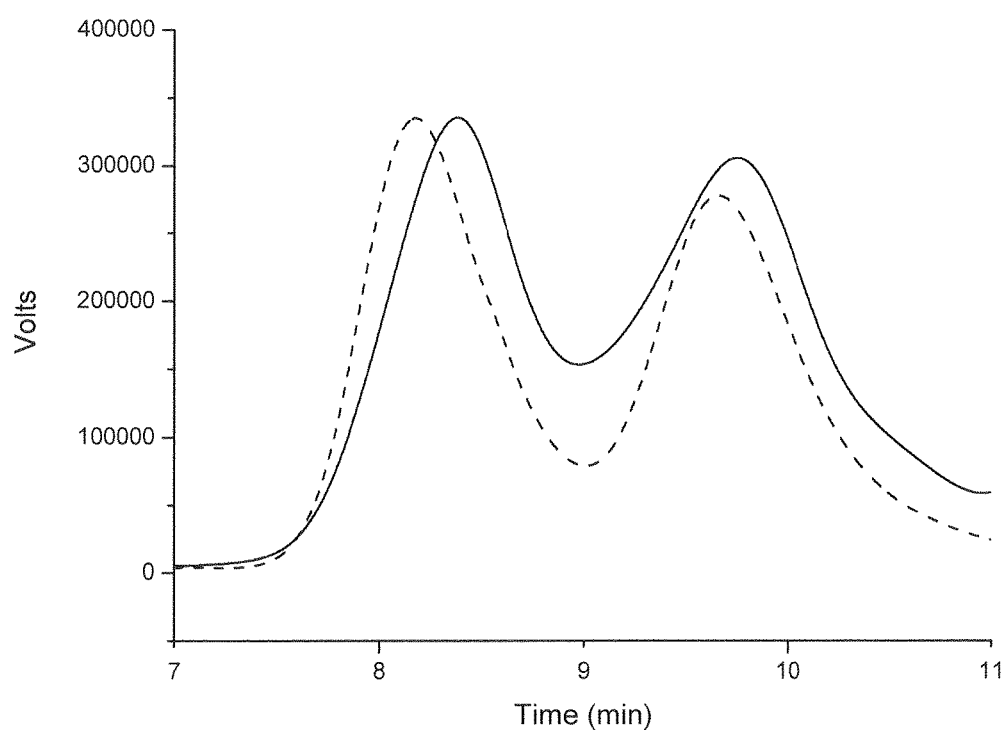
FIG. 16B shows a zoomed view of a region of the elution profiles shown in FIG. 16A.

The chromatograms in FIG. 15 illustrate the profile of the sample of standard solution of toluene, propylbenzene and butylbenzene eluting from the central section of the column (solid trace), in comparison to the sample eluting from the wall region (dotted trace), for the case where 70% of the total flow was directed through the peripheral waste ports to produce the dotted trace. Quite clearly from this illustration the detrimental effect of the wall can be seen. Band tailing was far more significant for the sample that eluted in the wall region, and these results for the wall region are also given in Table 1.

column fitted with a standard (one port) end fitting and conventional one-piece frit is shown in FIG. 16A (solid trace). When flow segmentation was introduced at the column outlet (dotted trace) so that flow exited through central and peripheral ports using the segmented outlet flow (multiport) end fitting, the number of theoretical plates increased by up to double when detecting the central portion separately, as detailed in Table 1. That is, efficiencies as measured by N increased by between 51 and 106% depending on each component (the measurement of N was affected by the degree of separation and the peak tailing in the non-segmented flow separation). Resolution was observed to increase on using flow segmentation from 0.81 to 1.03. FIG. 16B shows a zoomed view of a region of the chromatogram of FIG. 16A to more clearly illustrate the separation of two of the closely eluting components.

Another advantage of the flow segmentation end fitting is that poorly packed chromatography columns can be transformed into functional columns of good separation performance. For example, the separation of the simple four component mixture using a poorly packed chromatography

TABLE 1

| Column | Analyte | Segmentation to waste (%) (MP 70/30 MeOH/Water) | Centre Region | | Wall Region | | ΔN (%) |
|---|---|---|---|---|---|---|---|
| | | | N | Asymmetry factor | N | Asymmetry factor | |
| Stainless Steel | Toluene | 0 | 1643 | 1.32 | — | — | — |
| | | 30 | 1649 | 1.05 | 1170 | 1.43 | 0.4 |
| | | 50 | 2067 | 1.06 | 1350 | 1.37 | 26 |
| | | 70 | 2248 | 0.96 | 1476 | 1.28 | 37 |
| | Propyl benzene | 0 | 1500 | 1.28 | — | — | — |
| | | 30 | 1886 | 1.18 | 1256 | 1.42 | 26 |
| | | 50 | 2162 | 1.13 | 1494 | 1.37 | 44 |
| | | 70 | 2350 | 1.05 | 1428 | 1.35 | 57 |
| | Butyl benzene | 0 | 1622 | 1.24 | — | — | — |
| | | 30 | 1704 | 1.18 | 1286 | 1.39 | 5 |
| | | 50 | 1936 | 1.14 | 1383 | 1.35 | 19 |
| | | 70 | 2307 | 1.04 | 1506 | 1.30 | 42 |
| Glass FPLC | Toluene | Standard Endfitting (0% to waste) | 556 | N/A | — | — | — |
| | | Segmented flow fitting (50% to waste) | 838 | N/A | — | — | 51 |
| | Ethyl benzene | Standard endfitting | 401 | N/A | — | — | — |
| | | Segmented flow fitting | 825 | N/A | — | — | 106 |
| | Propyl benzene | Standard endfitting | 619 | N/A | — | — | — |
| | | Segmented flow fitting | 1012 | 1.64 | — | — | 63 |
| | Butyl benzene | Standard endfitting | 636 | 0.78 | — | — | — |
| | | Segmented flow fitting | 1138 | 1.65 | — | — | 79 |

Figure 17A:
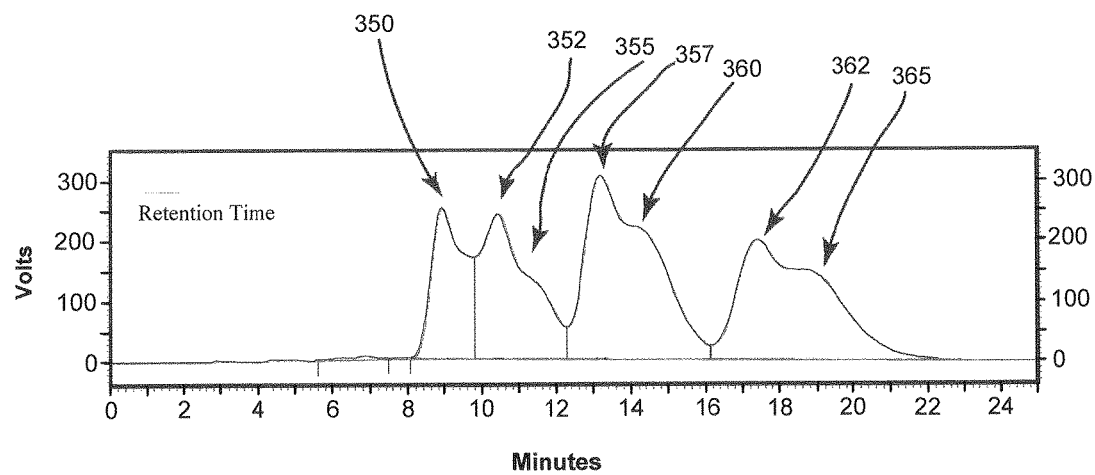
FIG. 17A shows the elution profile of a four component sample using a poorly packed chromatography column without flow segmentation.
Figure 17B:
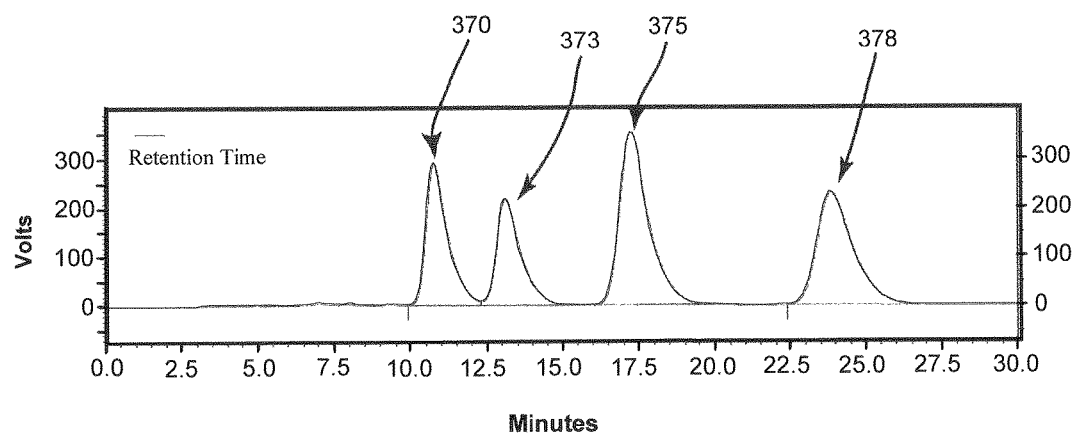
FIG. 17B shows the elution profile of the same sample using the same column with flow segmentation.

The improvements in elution efficiency described above as a result of using flow segmentation were observed on commercial quality, 100 mm HPLC columns. Even so, an improvement in efficiency up to 57% in the number of theoretical plates was observed. Further gains could be achieved with further refinement of the apparatus. Greater gains still were observed, however, when glass columns were utilised, similar to those that may be employed in FPLC systems. For example, the elution profile of the standard four component solution of toluene, ethylbenzene, propylbenzene and butylbenzene following separation on the 70 mm self packed (with C18 nucleosil silica) FPLC column is shown in FIG. 17. This column was deliberately damaged by disturbing the head of the column such that when the column was operated in a conventional manner it gave a lower column efficiency than would be expected for a well packed column. The chromatogram in FIG. 17A illustrates the elution profile of the four component mixture when 100% of the mobile phase exiting the column via a single exit port was taken to the detector, i.e. using a conventional end fitting with a single central exit port. In FIG. 17B, is shown the chromatographic separation when the same four components were separated in the same column using the same mobile phase as used for FIG. 17A, but using a multi-port end fitting with the peripheral exit ports open. Thus, liquid mobile phase exited the column from one centre port and four peripheral ports, but only the centre hole was connected to the detector that produced the chromatogram in FIG. 17B. The comparison of the separations shown in FIGS. 17A and 17B reveals important differences. In FIG. 17A, akin to a conventional outlet arrangement, a broad tail of material 355, 360, 365 is observed coming off the column after each of the main peaks that are relatively sharp 350, 352, 357, 362. Note that the broad tails cause some of the peaks to lack complete separation from their neighboring peaks. In contrast, in FIG. 17B, using segmented eluate flow, the peaks 370, 373, 375, and 378 arriving from the flow taken from the centre exit port of the column are narrow, have no tails, and are completely resolved. This data demonstrates that segmented-flow end-fittings not only improved column performance by improving the separation efficiency, but also significantly improved peak symmetry. On the well packed stainless columns, asymmetry values decreased from 1.32 to near perfectly symmetrical peaks with asymmetry factors of as low as 1.04. The improvement was more significant on the glass FPLC columns, whereby effectively split peaks were transformed into regular uniform peaks with only moderate tailing.

For certain applications, preferred embodiments of the present invention provide that the inlet as well as the outlet of the column is configured with a plurality of inlet ports in contrast to the single inlet port 41 of the conventional arrangement shown in FIGS. 2 and 3. As described in more detail hereinafter, preferred embodiments may use an end or inlet fitting (also termed end cap) on the inlet end of the column that has been modified to be unlike a conventional LC end fitting. A preferred modification is that the inlet frit and/or inlet end fitting are designed to introduce the mobile phase to the column through multiple channels that are positioned at different points in the transverse (radial) cross section of the column when the frit and/or fitting are positioned at the inlet. In this way, the mobile phase being introduced through the multiple channels arrives at different radial regions of the column. In preferred embodiments, a portion of mobile phase containing more sample is introduced to the more advantageous regions of the column such as the radially central region and another portion of mobile phase containing less or no sample is introduced to the less advantageous regions of the column such as the wall region. This inlet arrangement allows control of the flow speed and control of the sample concentration across the diameter of the column to produce more concentrated, better resolved and narrower component bands.

Figure 18:
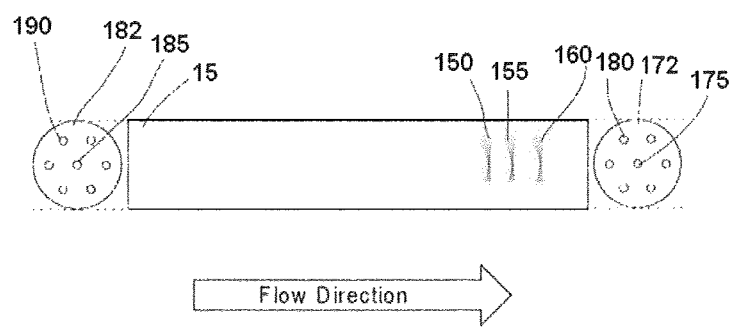
FIG. 18 shows schematically an axial cross-section side view through a packed chromatography column in accordance with the invention showing the principle of an inlet flow distributor and an outlet flow distributor.

FIG. 18 shows a schematic longitudinal cross sectional side view of the column similar to FIGS. 2, 3 and 4. FIG. 18 illustrates schematically the principle of an inlet flow distributor 182 at the inlet of the column 15, which is a packed column, e.g. for HPLC. To the left hand side of the longitudinal cross section side view is shown an end-on view of the column inlet (i.e. an end-on view of the flow distributor 182 on the inlet end of the column). The inlet flow distributor comprises a centre inlet port 185, positioned similarly to the single centre inlet port 41 of the conventional arrangement, that transmits mobile phase into the column (i.e. centre inlet port 185 is located on the central axis 17 of the column). Preferably, the centre inlet port 185 of the inlet flow distributor 182 transmits the mobile phase that is more concentrated with sample, and more preferably contains substantially all the sample. The inlet flow distributor 182 further comprises six peripheral inlet ports 190 located equally and symmetrically spaced around the central port 185 that transmit mobile phase to the perimeter region, closer to the inside wall of the column, which contains less or preferably no sample (i.e. it is solvent only where there is no sample). This perimeter flow of mobile phase provides a curtain flow annularly surrounding the central sample flow. It will be appreciated that in the case where all the sample is introduced via the centre port only a flow line feeding the centre inlet port need have a sample injection valve on it, i.e. the flow lines feeding the six peripheral inlet ports 190 need not have sample injection valves.

An outlet flow distributor 172 is provided at the outlet of the column 15. To the right hand side of the longitudinal cross section side view is shown an end-on view of the column outlet (i.e. an end-on view of the outlet flow distributor 172 on the end of the column). The outlet flow distributor comprises a centre outlet port 175, positioned similarly to the single centre port 40 of the conventional arrangement, that receives and transmits eluate flowing from the central radial region of the cross section of the column (i.e. a region located on the central axis 17 of the column) which contains the more concentrated and resolved components. The outlet flow distributor further comprises six peripheral ports 180 located equally spaced around the central port 175 that receive and transmit eluate that is flowing in the perimeter region, closer to the inside wall of the column, which contains the more dilute or no sample.

In contrast to the bowl-shaped, partially resolved bands 105, 110, 115, 120 produced by the conventional inlet arrangement in FIG. 3, the inlet arrangement of the invention shown in FIG. 4 provides flatter sample bands 150, 155 and 160, which may not touch the column walls at all where the sample is mostly or wholly contained in the central, sample flow at the inlet. The separately introduced curtain flow provided through the peripheral inlet ports 190 allows the flow speed of the mobile phase in the peripheral region of the column to more closely match the flow speed in the central region, thereby flattening the sample band. The respective portions of flow may be independently pumped for this purpose (e.g. pumped by separate pumps) or, alternatively, a single pump may drive both portions of flow and flow restrictors in the flow lines for each portion may control the respective flow velocities. The curtain flow also reduces the tendency of the sample in the central region to migrate or diffuse transversely, i.e. outwards towards the wall, thus concentrating the sample in the central region. Therefore, the sample bands 150, 155 and 160 reaching the outlet of the column are more concentrated, flatter and narrower leading to detected peaks which have higher S/N and are sharper and better resolved. The mobile phase portions may be of the same or different composition, e.g. the same or different solvents. One portion, e.g. a radially peripheral portion, may even be a non-solvent or at least a solvent having lower solubility for the sample to be separated (e.g. water), thereby further promoting the containment of sample in the other, e.g. radially central, portion.

This improvement in the sample band profile advancing through the column can be utilised most effectively by means of the outlet flow distributor 172. The eluate leaving the centre of the column represents the most desirable material because it is the most concentrated in components of the sample and has the most sharply resolved components. Thus, the separate use of the central port 175 of the outlet flow distributor 172 allows this most desirable portion of the eluate to be selectively directed to a detector and/or fraction collector (not shown). The eluate from the six peripheral ports 180 is gathered together and collectively forms one portion of eluate which is not processed with the eluate from the central port 175. For example, in one embodiment where the curtain flow contains some sample, in which eluate from the central port 175 is detected using a detector, the curtain flow eluate from the peripheral ports 180 may instead be either detected using another, separate detector or separately collected or could be sent to waste or it could be sent to the inlet of the same or another column for a further chromatographic separation in order to better resolve the components, optionally after being re-concentrated before such further chromatographic separation. The peripheral eluate is typically less desirable then the central eluate because it is more dilute and less resolved. Where the peripheral curtain flow eluate contains little or no sample, then it may be gathered from the peripheral exit ports 180 separately from the central sample flow and re-used as mobile phase in a subsequent round of chromatography, thereby saving on the consumption of mobile phase.

It will be appreciated that the inlet flow distributor may be the same design as any of the outlet flow distributors shown in the Figures and described above and where the outlet flow is referred to as being separated by the outlet flow distributor, such references may be substituted for references to separating the inlet flow of mobile phase. It will be appreciated that the inlet flow distributor may used with an inlet frit assembly, which likewise may be the same design as any of the outlet frit assemblies shown in the Figures and described above and where the outlet flow is referred to as being separated by the outlet frit assembly, such references may be substituted for references to separating the inlet flow of mobile phase.

It will be appreciated that the invention can provide significant improvements in the form of enhanced detection of samples and improved assay performance from a liquid chromatography column. In various embodiments the invention can enable, for example, a lower limit of detection for species being chromatographed due to improved detection sensitivity and/or improved peak capacity and peak resolution within a chromatographic assay. It will be appreciated that, as an alternative to improving peak resolution for a given column length, the invention may enable the use of shorter columns to attain a given peak resolution compared to an analogous conventional system. A shorter column will enable faster chromatographic separations to be performed. A further advantage, for example, is that the use of only a portion of the eluate for detection can mean that a reduced solvent load is introduced into the detector, which can be very beneficial for certain detectors such as mass spectrometers and other detectors operating in a vacuum environment. The invention may therefore better enable the use of conventional size columns with MS detection. With regard to preparative chromatography, the invention may enable the collection of purer fractions of samples due to the improved separation efficiency. The invention can conveniently be implemented from inexpensive materials, e.g. frit material and steel end fittings, and engineered in a simple manner, e.g. in the form of end fittings with multi-ports instead of a single port.

Figure 19:
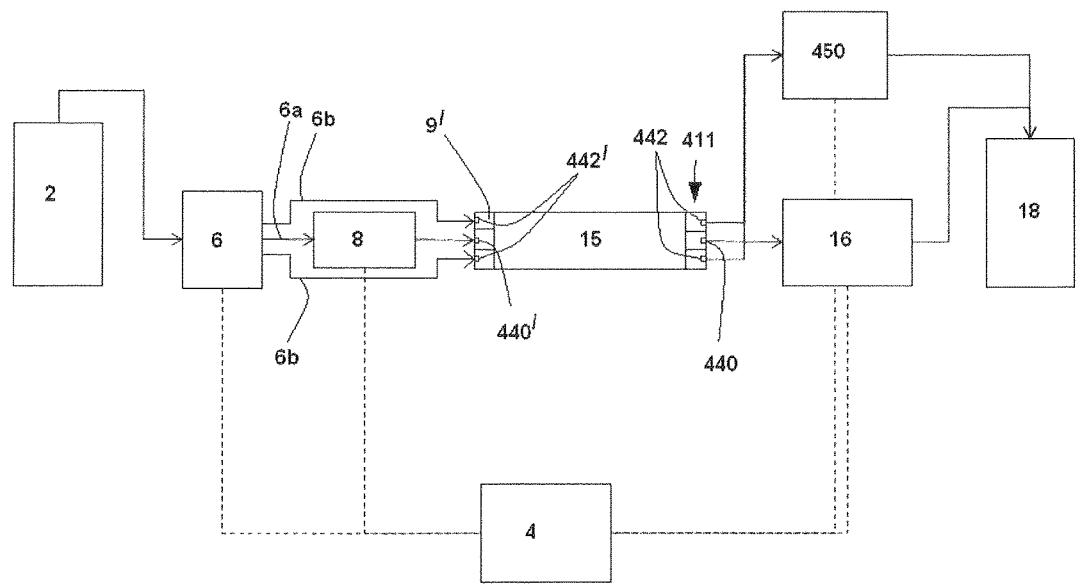
FIG. 19 shows schematically in the form of a flow chart another embodiment of an analytical LC system according to the invention having a segmented flow inlet.

In FIG. 19 is shown schematically in the form of a flow chart another embodiment of an analytical LC system according to the invention employing a segmented inlet system. The system is largely similar to the system shown in FIG. 10 and like reference numerals are therefore used to denote like components. At the inlet of the column the difference is that the solvent(s) 2 are delivered via tubing to a solvent delivery system 6 that employs, in this example, two pumps. The incoming solvent(s), if it is not already provided to the system 6 in the form of two separate portions, is divided into two portions. A first portion of the solvent is directed to and pumped by a first pump and a second portion of the solvent is directed to and pumped by a second pump within the system 6. The independent pumps enable the flow velocities of the portions to be independently controlled. The solvents are pumped to the column 15 via flow lines in the form of tubing 6a, 6b and 6c. The first portion of solvent is pumped through line 6a via a sample injection valve 8 where a sample is introduced into that portion solvent flow. The first portion of solvent loaded with sample is fed into the column 15 via centre inlet port 440' which lies on the central axis of the column. The second portion of solvent which does not contain sample is fed through lines 6b into the column 15 via outer or peripheral inlet ports 442' which annularly surround the centre inlet port 440'. The inlet also has a split frit assembly 9' such that the first portion of solvent flows through a central section of frit and the second portion of solvent flows through a peripheral section of frit annularly surrounding the central section. It will be appreciated that variations of the shown embodiment can be provided, for example the lines 6b could also have a sample injection valve 8 and thereby be supplied with an amount of sample if desired.

Figure 20:
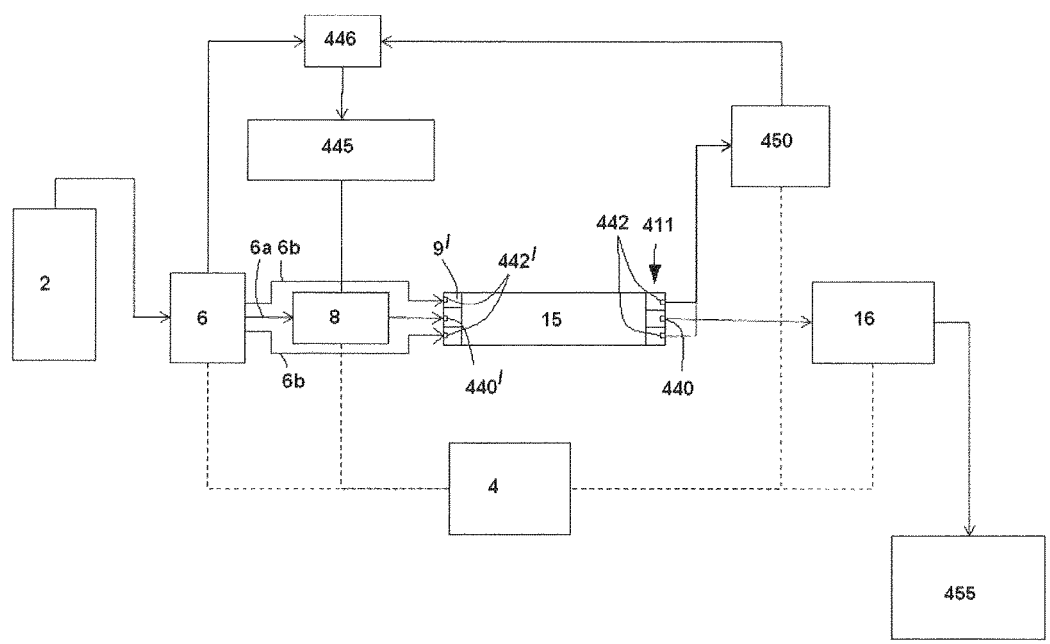
FIG. 20 shows schematically in the form of a flow chart another embodiment of an LC system according to the invention having a segmented flow inlet and employing recycling of a portion of the eluate.

In another embodiment as shown in schematic FIG. 20, eluate gathered from the central exit port 440 is sent through a detector 16 to a fraction collection device 455. Eluate gathered from the peripheral exit ports 442, however, is not sent through a detector or to a fraction collection device 455, but via valve 446 can be either sent to the solvent delivery system 6 for re-use of the solvent or saved in one or more reservoirs 445 (which may be any suitable reservoir, for example a trap or additional column), which is or are in communication with the sample-injection valve 8 for the primary column 15 for re-cycling. At an appropriate time the primary column 15 may then be loaded again, this time with the peripherally eluted material (in cases where sample is contained therein) from the previous run(s) collected in the reservoir 445, which is injected into the solvent stream through sample-injection valve 8. The central eluting eluate is once again detected and collected in the fraction collection device 455. Further cycles of chromatographic processing may be used until a sufficiently high and desired proportion of the total material in the original sample is purified and fractionated under the highest-level of chromatography available, by means of taking and collecting the material from the centre exit port 440 separately each time.

Examples (2)

Further experiments were conducted to demonstrate the effect of a segmented inlet.

The experiments were conducted on a 100×21 mm steel column packed with 12 μm pentafluorophenyl-silica stationary phase particles. Various experiments testing the different column hardware configurations were undertaken on the same column, with head fittings interchanged as appropriate. The experiments conducted used: (1) conventional column (single inlet port and single outlet port); (2) conventional column inlet fitting (single inlet port) with segmented flow outlet fitting (4 ports: 1 central port and 3 peripheral ports); and (3) curtain flow column inlet fitting (4 ports: 1 central port and 3 peripheral ports) with segmented flow outlet fitting (4 ports: 1 central port and 3 peripheral ports). Injection of toluene, propyl benzene and butyl benzene, in a 30/70 water/methanol mobile phase (250 μL) was used to test performance for these three modes of operation. The results are described below.

An illustration of the parabolic nature of the plug flow through a conventional column is shown in FIG. 2 and has been described above. In the experiments (2) and (3) described here, the outlet end fitting was designed so as to separate the region of flow near the column wall from that of the flow in the central section of the packed bed. The inlet end fitting was designed so as to introduce separate flows of mobile phase respectively into the region near the column wall and region in the central section of the packed bed. The design of the fittings used for the experiments is that illustrated in FIGS. 7 and 9. With this end fitting, the eluate flow from the wall region was passed to waste, via a UV detector, while the central region was analysed alone in a conventional manner using a separate UV detector.

Figure 21:
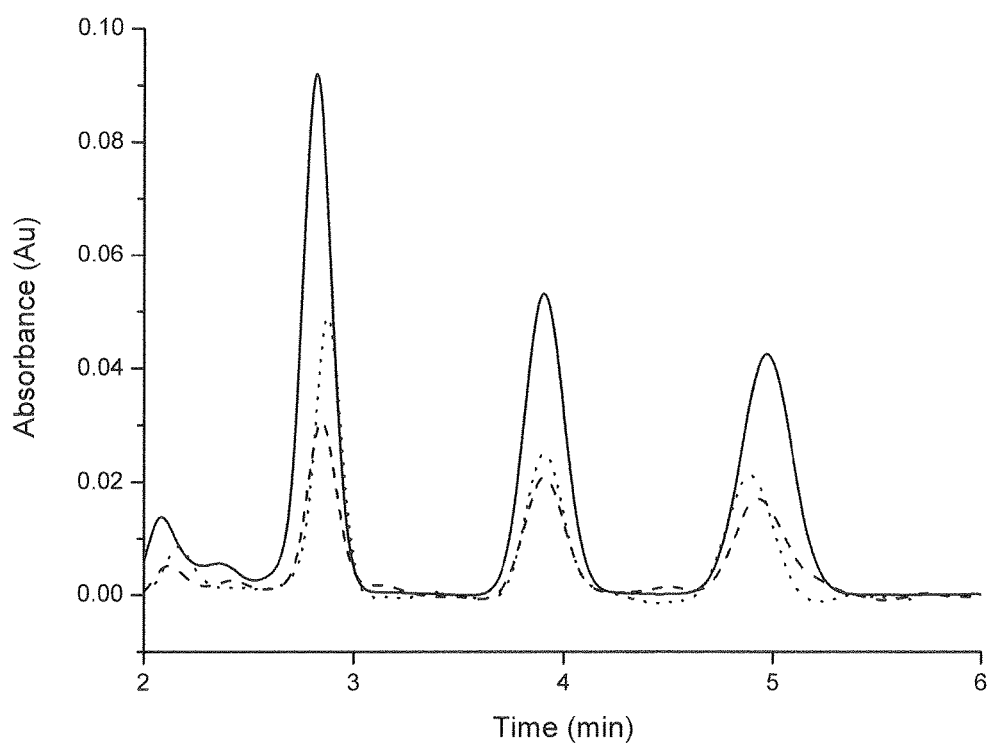
FIG. 21 shows a comparison of peaks form three solutes, toluene, propyl benzene and butyl benzene, arriving in an HPLC system under different conditions of mobile phase segmentation using an inlet flow distributor.

FIG. 21 illustrates the chromatographic separation of the three component mixture obtained for each mode of operation (1), (2) and (3). The elution order was toluene, propyl benzene and then butyl benzene. The conventional chromatography mode (1) is shown by the dashed line, the segmented outlet flow mode (2) is shown by the dotted line and the curtain flow mode (3) is shown by the solid line. The split ratio of the segmented outlet flow was 54% of mobile phase eluting to waste via the peripheral ports and the remainder via the centre port being detected or collected. Curtain flow ratio was 1:3.5 (central zone:curtain zone). All total flow rates at column inlet were 18 mL/min. Of primary significance in these separations was the 155% gain in sensitivity observed for the curtain flow injection in experiment (3), detailed below in Table 2, compared to a normal mode of operation (1).

stantially narrower than both the normal mode of operation (1), and the curtain flow mode of operation (3). Plate counts (N) and other figures of merit that describe the efficiency are also included in Table 2. There was a 16% increase in efficiency for the segmented mode of operation, but no change in the separation efficiency for the curtain flow mode, compared to the normal mode, of operation. It should be noted, however, that these measures of N are not the best measure for the specific designs used, as discussed further (see later text). Separation in the curtain flow mode (3), however, yielded a peak that was perfectly symmetrical, as opposed to the slight tailing observed in the normal mode of operation (1). Also of note from the data in Table 2, was that the sample that eluted in the waste stream via the peripheral ports using the segmented outlet mode of operation (2) was approximately 12.5% more efficient than a normal mode of operation.

The measurement of plate counts, N, requires isocratic, steady state conditions. One key aspect of the described experiments that limits the comparison of performance between the different modes of operation is that the flow rate through the detector differs between the normal mode of operation and any other mode of operation that involves segmented outlet flow through a detector. In all modes of operation—normal (1), segmented outlet (2), or curtain flow with segmented outlet (3), the volumetric flow through the bed remained constant, however, flow stream splitting at the column outlet resulted in only 46% of the solvent passing through the detector for the segmented modes of operation. Hence, the apparent peak width for modes (2) and (3) was in essence broadened twice as much as for the normal mode of operation (1). This artificially reduces the apparent measure of the number of theoretical plates. A better reflection,

TABLE 2

| | Centre | | | | Wall | | |
|---|---|---|---|---|---|---|---|
| Flow mode | Height (μV) | N | Asymmetry factor | % ΔN relative to normal mode | Height (μV) | N | Asymmetry factor |
| (1) Normal | 16380 | 2111 | 1.10 | — | — | — | — |
| (2) Segmented flow outlet | 20988 | 2457 | 0.97 | 16 | 17403 | 2374 | 0.99 |
| (3) Curtain flow point injection | 41786 | 2100 | 1.00 | 0 | — | — | — |

This gain in sensitivity is thought to be a result of a two-fold effect:

(i) All sample in the curtain flow mode (3) was loaded directly to the column central zone via the central inlet port and subsequently the sample (100% thereof) eluted through the central port of the segmented outlet fitting with no sample component observed to elute in the waste stream via the peripheral outlet ports at the limit of detection. Hence the sample eluted with the same mass load as a normal mode of operation (1), but in a substantially smaller elution volume as detailed further below.

(ii) The volume flow through the detector was lower since only 46% of the solvent was sent through the detector. That is, the flow rate through the detector in mode of operation (3) was 8.3 mL/min, compared to 18 mL/min in the normal mode of operation (1). Hence the increase in detector residence time yielded greater sensitivity.

Figure 22:
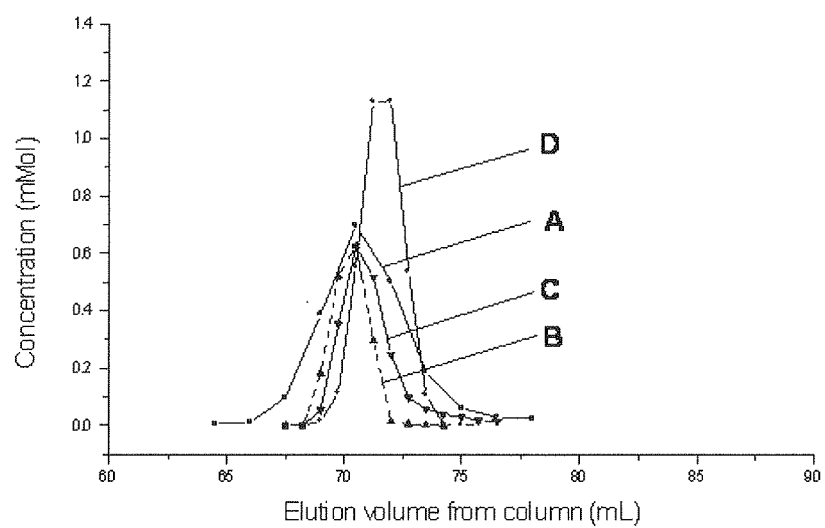
FIG. 22 shows the elution profiles compared by elution volume of the propyl benzene peak in the HPLC system under different conditions of mobile phase segmentation using an inlet flow distributor.

Also apparent in FIG. 21 is that the segmented outlet mode (2) yielded chromatographic profiles that were subtherefore of the separation performance in segmented modes of operation can be obtained by measuring the amount of solute eluting in the collection volume of sample (i.e. concentration of the solute). To measure this, a further study was therefore conducted in which sample bands were fractionated across their elution volume at five second intervals. Each fraction was then analysed to determine the amount of solute that eluted. The amount of solute collected was then plotted as a function of the elution volume from the column, results of which are shown in FIG. 22. Trace A was obtained from the conventional mode (1), Trace B was obtained from the segmented flow mode (2) using sample eluting from the centre port, Trace C was obtained from the segmented flow mode (2) using sample eluting from the wall region (peripheral ports) and Trace D was obtained from the curtain flow mode (3).

FIG. 22 illustrates the comparison in separation performance (gauged on the elution of the propyl benzene band) between the normal mode of operation (1) and each of the segmented flow mode of operation (2) and the curtain flow injection mode (3) for this fractionation study. Clearly these separations illustrate an advanced level of separation performance for each of the segmented flow modes of operation and curtain flow. The sample collection volume for the segmented flow mode of operation (2), for sample collected from the central flow stream (Trace B) was approximately 4 mL and 7 mL from the wall region (Trace C). The sample collection volume for the curtain flow injection (Trace D) with segmented outlet flow was approximately 5.5 mL. In the conventional mode of operation the sample collection volume was 11 mL. Therefore, the most efficient mode of sample component extraction, at least with respect to peak volume, was the segmented flow mode of operation with sample collected through the central outlet section. However, in this mode of operation approximately 50% of the sample was sent to the waste stream, albeit the sample was then subsequently contained in around 7 mL of solvent. Since in the curtain flow mode of operation 100% of the sample elutes via the central flow stream, this mode of operation yielded the most efficient extraction process, being 100% more efficient than the conventional mode of operation, at least with respect to the sample collection concentration (and thus detection sensitivity), as well as exhibiting improved separation efficiency with respect to peak volume. Further cost effectiveness could be attained in regard to solvent recycling, since no sample was observed to elute from the wall region of the column with the curtain flow regime. This solvent could thus be recycled without any energy requirement, which in the described mode of operation would account for 54% of the entire solvent consumption.

As used herein, including in the claims, unless the context indicates otherwise, singular forms of the terms herein are to be construed as including the plural form and vice versa. For instance, unless the context indicates otherwise, a singular reference, such as "a" or "an" means "one or more".

Throughout the description and claims of this specification, the words "comprise", "including", "having" and "contain" and variations of the words, for example "comprising" and "comprises" etc, mean "including but not limited to", and are not intended to (and do not) exclude other components.

It will be appreciated that variations to the foregoing embodiments of the invention can be made while still falling within the scope of the invention. Each feature disclosed in this specification, unless stated otherwise, may be replaced by alternative features serving the same, equivalent or similar purpose. Thus, unless stated otherwise, each feature disclosed is one example only of a generic series of equivalent or similar features.

The use of any and all examples, or exemplary language ("for instance", "such as", "for example", "e.g." and like language) provided herein, is intended merely to better illustrate the invention and does not indicate a limitation on the scope of the invention unless otherwise claimed. No language in the specification should be construed as indicating any non-claimed element as essential to the practice of the invention.

Any steps described in this specification may be performed in any order or simultaneously unless stated or the context requires otherwise.

All of the features disclosed in this specification may be combined in any combination, except combinations where at least some of such features and/or steps are mutually exclusive. In particular, the preferred features of the invention are applicable to all aspects of the invention and may be used in any combination. Likewise, features described in non-essential combinations may be used separately (not in combination).

The invention claimed is:

1. An apparatus for column chromatography comprising a chromatography column, the chromatography column having an inlet and an outlet, wherein the outlet is provided with a frit assembly comprising:
   a) a central porous frit;
   b) at least one concentric radially outer porous frit annularly surrounding the central porous frit;
   c) an intervening non-porous flow barrier annularly surrounding the central porous frit, in which the intervening non-porous flow barrier separates the central porous frit and the at least one concentric radially outer porous frit,
   in which the frit assembly is configured to split a flow of eluate as it leaves the chromatography column through the outlet into at least a first eluate portion and a second eluate portion, in which the first eluate portion is separate from the second eluate portion, in which the intervening non-porous flow barrier prevents a lateral flow of eluate between the central porous frit and the at least one concentric radially outer porous frit, wherein the apparatus is configured to separately process the first eluate portion and the second eluate portion.

2. The apparatus of claim 1, wherein the outlet is configured to direct the first eluate portion to a first processing means and the second eluate portion to a second processing means separate from the first processing means.

3. The apparatus of claim 1, wherein the first eluate portion and the second eluate portion emanate from different radial regions of the chromatography column.

4. The apparatus of claim 1, wherein the outlet is arranged to split the flow of eluate as it leaves the chromatography column into three or more separate eluate portions.

5. The apparatus of claim 1, wherein the first eluate portion is 50% or less of a total volume of the eluate.

6. The apparatus of claim 1, wherein a ratio of an area of the concentric radially outer porous frit to an area of the central porous frit is from about 2.5:1 to about 1.5:1.

7. The apparatus of claim 1, wherein a width in a radial direction of the intervening non-porous flow barrier is lower than a width in a radial direction of each of the central porous frit and the at least one concentric radially outer porous frit.

8. The apparatus of claim 1, wherein the frit assembly comprises an outer fitting, the outer fitting having at least two apertures to separate the flow of eluate into at least the first eluate portion and the second eluate portion.

9. The apparatus of claim 1, wherein the chromatography column has a flow distributor at the outlet to convey at least the first eluate portion and the second eluate portion in separate channels therein.

10. The apparatus of claim 9, wherein the flow distributor is a separate part which is fitted to an end of the chromatography column in use.

11. The apparatus of claim 9, wherein the flow distributor comprises a first set of at least one channel arranged such that in use the first set lies in a first radial region of the chromatography column to convey the first eluate portion and a second set of at least one channel arranged such that in use the second set lies in a second radial region of the chromatography column to convey the second eluate portion.

12. The apparatus of claim 11, wherein the first radial region of the chromatography column is a central radial region and the second radial region of the chromatography column is a region located radially outward of the central radial region.

13. The apparatus of claim 11, wherein the flow distributor comprises one central channel in the first set and from three to ten outer channels in the second set.

14. The apparatus of claim 10, wherein the flow distributor in use is in contact with the non-porous intervening flow barrier of the frit assembly so that the non-porous intervening flow barrier of the frit assembly provides a seal between the frit assembly and the flow distributor thereby sealing adjacent portions of eluate flow from each other.

15. The apparatus of claim 1, wherein the apparatus comprises a detector arranged to detect at least one eluate portion separately from another eluate portion or eluate portions.

16. The apparatus of claim 1, wherein the apparatus comprises a fraction collector arranged to collect fractions of at least the first eluate portion separately from the second eluate portion.

17. The apparatus of claim 15, wherein the detector is arranged to separately detect the first eluate portion which has emanated from a central radial region of the column.

18. The apparatus of claim 16, wherein the fraction collector is arranged to separately collect fractions of the first eluate portion-which has emanated from a central radial region of the chromatography column.

19. The apparatus of claim 1, wherein the apparatus is configured to send one or more eluate portions of at least the first eluate portion and the second eluate portion to a waste receiver or to the inlet of the chromatography column.

20. The apparatus of claim 1, wherein the apparatus comprises at least first and second processing means for separately processing at least the first eluate portion and the second eluate portion, wherein the first and second processing means each independently comprise one or more of: a detector, a waste reservoir, a fraction collector and the inlet of the chromatography column.

21. The apparatus of claim 1, wherein the chromatography column is a column for analytical chromatography selected from: high performance liquid chromatography (HPLC), ultra-high performance liquid chromatography (UHPLC), multi-dimensional or two dimensional high performance liquid chromatography (MDHPLC or 2DHPLC), flash column chromatography, fast protein liquid chromatography (FPLC) and supercritical fluid (SCF) chromatography.

22. The apparatus of claim 1, wherein the chromatography column is a column for preparative chromatography.

23. The apparatus of claim 1, wherein the inlet is configured to introduce a flow of mobile phase into the chromatography column in at least two separate portions which are independently controllable, and to introduce the portions into different radial regions of the chromatography column, such that the portions flow longitudinally through the chromatography column in different radial regions.

24. The apparatus of claim 23, wherein a first portion of mobile phase is introduced into a central radial region of the chromatography column and a second portion of mobile phase is introduced into a peripheral radial region located radially outwards of the central radial region.

25. The apparatus of claim 24, wherein a sample to be separated is contained in the first portion of mobile phase in a higher concentration than in the second portion.

26. The apparatus of claim 23, wherein the mobile phase portions are controllable to have substantially the same flow velocity.

27. The apparatus of claim 23, wherein the inlet is provided with an inlet frit assembly configured to segment the mobile phase into at least two separate portions.

28. The apparatus of claim 23, wherein the chromatography column has an inlet flow distributor at the inlet to convey the at least two separate portions of the mobile phase in separate channels therein.

29. The apparatus of claim 1, wherein the at least one concentric radially outer porous frit has a shape of a concentric porous frit ring.

30. An apparatus for column chromatography comprising a chromatography column, the chromatography column having an inlet and an outlet, wherein the outlet is provided with a frit assembly comprising:
   a) a central porous frit;
   b) at least one concentric radially outer porous frit annularly surrounding the central porous frit;
   c) an intervening non-porous flow barrier annularly surrounding the central porous frit, in which the intervening non-porous flow barrier separates the central porous frit and the at least one concentric radially outer porous frit,
   in which the frit assembly is configured to direct one portion of a flow of eluate as it leaves the chromatography column to be processed separately from a remainder of the eluate, wherein the one portion emanates from a central radial region of the chromatography column, the central radial region has a radius less than a full width of the column, in which the intervening non-porous flow barrier prevents a lateral flow of eluate between the central porous frit and the at least one concentric radially outer porous frit.

* * * * *